US011788096B2

(12) United States Patent
Nuccio et al.

(10) Patent No.: US 11,788,096 B2
(45) Date of Patent: *Oct. 17, 2023

(54) EXCISABLE INHT31 TRANSGENIC SOYBEAN GLYPHOSATE TOLERANCE LOCUS

(71) Applicant: INARI AGRICULTURE TECHNOLOGY, INC., Cambridge, MA (US)

(72) Inventors: Michael Lee Nuccio, Salem, NH (US); Michael Andreas Kock, Rheinfelden (DE); Joshua L. Price, Cambridge, MA (US); Daniel Rodriguez Leal, Belmont, MA (US)

(73) Assignee: INARI AGRICULTURE TECHNOLOGY, INC., Cambridge, MA (US)

( * ) Notice: Subject to any disclaimer, the term of this patent is extended or adjusted under 35 U.S.C. 154(b) by 52 days.

This patent is subject to a terminal disclaimer.

(21) Appl. No.: 17/650,031

(22) Filed: Feb. 4, 2022

(65) Prior Publication Data

US 2022/0154194 A1 May 19, 2022

Related U.S. Application Data

(63) Continuation of application No. 17/302,121, filed on Apr. 23, 2021, now Pat. No. 11,242,534.

(60) Provisional application No. 63/201,029, filed on Apr. 9, 2021, provisional application No. 63/199,930, filed on Feb. 3, 2021, provisional application No. 63/059,916, filed on Jul. 31, 2020, provisional application No. 63/059,963, filed on Jul. 31, 2020, provisional application No. 63/059,813, filed on Jul. 31, 2020, provisional application No. 63/059,860, filed on Jul. 31, 2020.

(51) Int. Cl.
C12N 15/82 (2006.01)

(52) U.S. Cl.
CPC .................. C12N 15/8213 (2013.01)

(58) Field of Classification Search
None
See application file for complete search history.

(56) References Cited

U.S. PATENT DOCUMENTS

| 7,632,985 | B2* | 12/2009 | Malven .............. C12N 15/8286 800/300 |
| 8,232,456 | B2 | 7/2012 | Long et al. |
| 8,450,561 | B2 | 5/2013 | Beazley et al. |
| 8,455,720 | B2 | 6/2013 | Long et al. |
| 8,575,434 | B2 | 11/2013 | Diehn et al. |
| 9,540,655 | B2 | 1/2017 | Cui et al. |
| 9,944,945 | B2 | 4/2018 | Malven et al. |
| 11,041,172 | B2 | 6/2021 | Cermak |
| 11,214,811 | B1 | 1/2022 | Nuccio et al. |
| 11,242,534 | B1 | 2/2022 | Nuccio et al. |
| 11,359,210 | B2 | 6/2022 | Price et al. |
| 2006/0282911 | A1 | 12/2006 | Bull et al. |
| 2010/0162428 | A1 | 6/2010 | Brown et al. |
| 2011/0191899 | A1 | 8/2011 | Ainley et al. |
| 2015/0059010 | A1 | 2/2015 | Cigan et al. |
| 2015/0082478 | A1 | 3/2015 | Cigan et al. |
| 2017/0166912 | A1 | 6/2017 | Brower-Toland et al. |
| 2018/0163218 | A1 | 6/2018 | Corbin et al. |
| 2019/0112614 | A1 | 4/2019 | Russell et al. |
| 2019/0136249 | A1 | 5/2019 | Sakai et al. |
| 2019/0352655 | A1 | 11/2019 | Niu et al. |
| 2020/0157554 | A1 | 5/2020 | Cigan et al. |
| 2022/0030806 | A1 | 2/2022 | Price et al. |
| 2022/0030822 | A1 | 2/2022 | Nuccio et al. |
| 2022/0033836 | A1 | 2/2022 | Price et al. |
| 2022/0098602 | A1 | 3/2022 | Nuccio et al. |
| 2022/0251584 | A1 | 8/2022 | Nuccio et al. |
| 2022/0364105 | A1 | 11/2022 | Price et al. |
| 2023/0077473 | A1 | 3/2023 | Price et al. |
| 2023/0078387 | A1 | 3/2023 | Kock et al. |
| 2023/0083144 | A1 | 3/2023 | Nuccio et al. |
| 2023/0087222 | A1 | 3/2023 | Kock et al. |
| 2023/0147013 | A1 | 5/2023 | Nuccio et al. |

FOREIGN PATENT DOCUMENTS

| WO | 2022026375 A1 | 2/2022 |
| WO | 2022026379 A1 | 2/2022 |
| WO | 2022026390 A1 | 2/2022 |
| WO | 2022026395 A2 | 2/2022 |
| WO | 2022026403 A2 | 2/2022 |

(Continued)

OTHER PUBLICATIONS

International Searching Authority in connection with PCT/US21/43897 filed Jul. 30, 2021, "Invitation to Pay Additional Fees And, Where Applicable, Protest Fee", 3 pages, dated Oct. 27, 2021

International Searching Authority in connection with PCT/US21/43945 filed Jul. 30, 2021, "Invitation to Pay Additional Fees And, Where Applicable, Protest Fee", 4 pages, dated Oct. 27, 2021.

International Searching Authority in connection with PCT/US21/43935 filed Jul. 30, 2021, "Invitation to Pay Additional Fees And, Where Applicable, Protest Fee", 3 pages, dated Oct. 26, 2021.

Baliga et al., "Investigation of direct repeats, spacers and proteins associated with clustered regularly interspaced short palindromic repeat (CRISPR) system of Vibrio parahaemolyticus", Molecular Genetics and Genomics, vol. 294, pp. 253-262, 2019.

(Continued)

*Primary Examiner* — Weihua Fan
*Assistant Examiner* — Brian James Sullivan
(74) *Attorney, Agent, or Firm* — McKee, Voorhees & Sease, PLC

(57) ABSTRACT

Transgenic INHT31 soybean plants comprising modifications of the MON89788 soybean locus which provide for facile excision of the modified MON89788 transgenic locus or portions thereof, methods of making such plants, and use of such plants to facilitate breeding are disclosed.

7 Claims, 8 Drawing Sheets

Figure 3:
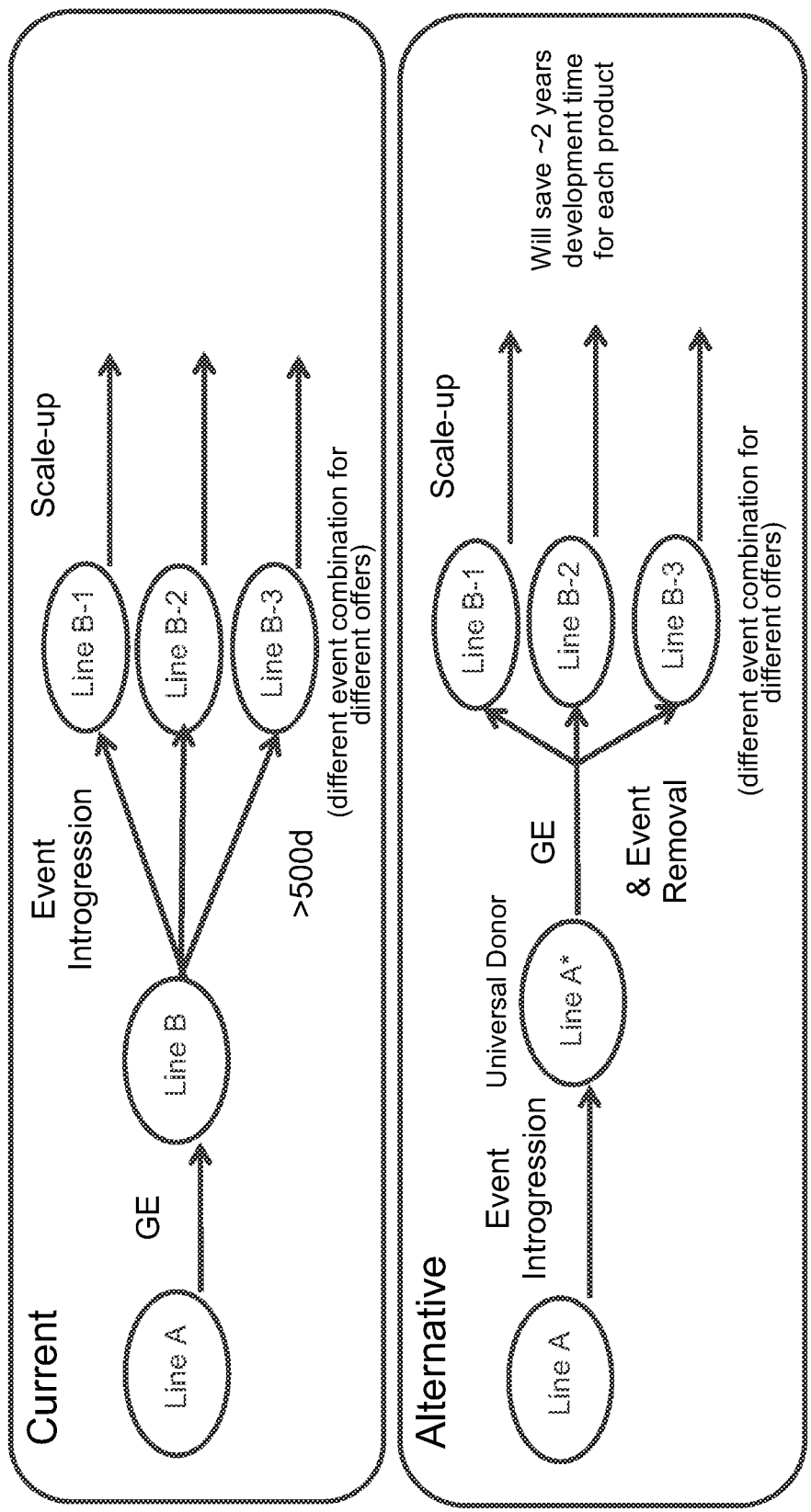

Specification includes a Sequence Listing.

(56) References Cited

FOREIGN PATENT DOCUMENTS

WO      2022026801 A1     2/2022

OTHER PUBLICATIONS

Bortesi et al., "The CRISPR/Cas9 system for plant genome editing and beyond", Biotechnology Advances, vol. 33, pp. 41-52, Dec. 16, 2014.

Cho et al., "Nonallelic homologous recombination events responsible for copy number variation within an RNA silencing locus", Plant Direct, vol. 3, 16 pages, Aug. 5, 2019.

Biopesticides Registration Action Document, "Bacillus thuringiensis Vip3Aa20 Insecticidal Protein and the Genetic Material Necessary for Its Production (via Elements of Vector pNOV1300) in Event MIR162 Maize (OECD Unique Identifier: SYN-IR162-4)", PC Code: 006599, Vip3Aa20 Maize, pp. 1-175, Mar. 2009.

Du et al., "Construction of Marker-Free Genetically Modified Maize Using a Heat-Inducible Auto-Excision Vector", Genes, vol. 10, No. 374, pp. 1-17, 2019.

Du et al., "Infection of Embryonic Callus with Agrobacterium Enables High-Speed Transformation of Maize", International Journal of Molecular Sciences, vol. 20,. No. 279, pp. 1-15, doi:10.3390/ijms20020279, 2019.

Finnigan et al., "mCAL: A New Approach for Versatile Multiplex Action of Cas9 Using One sgRNA and Loci Flanked by a Programmed Target Sequence", G3, vol. 6, pp. 2147-2156, Jul. 2016.

Kim et al., "CRISPR/Cpf1-mediated DNA-free plant genome editing", Nature Communications, vol. 8, Article No. 14406, 7 pages, Feb. 16, 2017.

Li et al., "Expanding the Scope of CRISPR/Cpf1-Mediated Genome Editing in Rice", Molecular Plant, vol. 11, No. 7, pp. 1-14, 2018.

Luo et al., "Improperly Terminated, Unpolyadenylated mRNA of Sense Transgenes is Targeted by RDR6-Mediated RNA Silencing in *Arabidopsis*", The Plant Cell, vol. 19, pp. 943-958, Mar. 2007.

Malzahn et al., "Application of CRISPR-Cas12a temperature sensitivity for improved genome editing in rice, maize, and *Arabidopsis*", BMC Biology, vol. 17, No. 9, https://doi.org/10.1186/s12915-019-0629-5, pp. 1-14, 2019.

United States Patent and Trademark Office in connection with U.S. Appl. No. 17/248,936, filed Feb. 12, 2021, "Non-Final Office Action" 30 pages, dated Mar. 25, 2021.

United States Patent and Trademark Office in connection with U.S. Appl. No. 17/249,640, filed Mar. 8, 2021, "Non-Final Office Action", 19 pages, dated Jun. 29, 2021.

United States Patent and Trademark Office in connection with U.S. Appl. No. 17/302,739, filed May 11, 2021, "Non-Final Office Action", 29 pages, dated Aug. 3, 2021.

United States Patent and Trademark Office in connection with application No. 17/302,110 filed Apr. 23, 2021, "Non-Final Office Action", 22 pages, dated Jun. 29, 2021.

Que et al., "Maize transformation technology development for commercial event generation", Frontiers in Plant Science, vol. 5, Article 379, pp. 1-19, 2014.

Srivastava, et al., "Dual-targeting by CRISPR/Cas9 for precise excision of transgenes from rice genome", Plant Cell Tissue and Organ Culture, vol. 129, pp. 153-160, 2017.

Srivastava et al., "Gene Stacking by recombinases", Plant Biotechnology Journal, vol. 14, pp. 471-482, 2016.

Ward et al., "Petition for Determination of Nonregulated Status for Insect-Resistant MIR162 Maize", Syngenta, pp. 1-271, 2007.

Xing et al., "Revealing frequent alternative polyadenylation and widespread low-level transcription read-through of novel plant transcription terminators", Plant Biotechnology Journal, vol. 8, pp. 772-782, 2010.

Young et al., "CRISPR-Cas9 Editing in Maize: Systematic Evaluation of Off-target Activity and Its Relevance in Crop Improvement", Scientific Reports, vol. 9, 11 pages, Apr. 15, 2019.

Begemann et al., "Precise insertion and guided editing of higher plant genomes using Cpf1 CRISP nucleases," Scientific Reports, Sep. 14, 2017, vol. 7, No. 11606, pp. 1-6.

Begemann et al., Supplementary Data—Precise insertion and guided editing of higher plant genomes using Cpf1 CRISPR nucleases, Scientific Reports, Sep. 14, 2017, vol. 7, No. 11606, 18 pages.

Danilo et al., "The DFR locus: A smart landing pad for targeted transgene insertion in tomato," PLoS One, Dec. 6, 2018, vol. 13, No. 12, pp. 1-14.

Gleditzsch et al., "PAM identification by CRISPR-Cas effector complexes: diversified mechanisms and structures," RNA Biology, 2019, vol. 16, No. 4, pp. 504-517.

Gurusaran et al., "RepEX: Repeat extractor for biological sequences," Genomics, Jul. 31, 2013, vol. 102, pp. 403-408.

International Search Report in PCT/US2021/043161, dated Jan. 5, 2022, 6 pages.

International Search Report in PCT/US2021/043170, dated Jan. 5, 2022, 6 pages.

International Search Report in PCT/US2021/043187, dated Jan. 6, 2022, 6 pages.

International Search Report in PCT/US2021/043192, dated Jan. 27, 2022, 7 pages.

International Search Report in PCT/US2021/043207, dated Jan. 27, 2022, 6 pages.

International Search Report in PCT/US2021/043440, dated Dec. 2, 2021, 3 pages.

International Search Report in PCT/US2021/043468, dated Nov. 26, 2021, 4 pages.

International Search Report in PCT/US2021/043479, dated Nov. 23, 2021, 3 pages.

International Search Report in PCT/US2021/043483, dated Dec. 16, 2021, 3 pages.

International Search Report in PCT/US2021/043496, dated Dec. 1, 2021, 4 pages.

International Search Report in PCT/US2021/043851, dated Dec. 30, 2021, 6 pages.

International Search Report in PCT/US2021/043919, dated Jan. 20, 2022, 8 pages.

International Search Report in PCT/US2021/043933, dated Dec. 30, 2021, 6 pages.

International Search Report in PCT/US2021/044198, dated Jan. 19, 2022, 6 pages.

Non-Final Office Action in U.S. Appl. No. 17/302,110, dated Mar. 15, 2022, 23 pages.

Non-Final Office Action in U.S. Appl. No. 17/302,121, dated Jul. 8, 2021, 10 pages.

Non-Final Office Action in U.S. Appl. No. 17/680,647, dated Jun. 23, 2022, 11 pages.

Non-Final Office Action in U.S. Appl. No. 18/057,860, dated Jun. 1, 2023, 49 pages.

Non-Final Office Action in U.S. Appl. No. 18/057,867, dated Jun. 7, 2023, 17 pages.

Non-Final Office Action in U.S. Appl. No. 18/058,081, dated Apr. 11, 2023, 19 pages.

Non-Final Office Action in U.S. Appl. No. 18/058,144, dated Jun. 7, 2023, 49 pages.

Non-Final Office Action in U.S. Appl. No. 18/058,156, dated May 19, 2023, 24 pages.

Non-Final Office Action in U.S. Appl. No. 18/058,161, dated Apr. 11, 2023, 15 pages.

Non-Final Office Action in U.S. Appl. No. 18/162,134, dated Jun. 21, 2023, 28 pages.

Notice of Allowance in U.S. Appl. No. 17/248,936, dated Mar. 10, 2022, 7 pages.

Notice of Allowance in U.S. Appl. No. 17/249,640, dated Sep. 22, 2021, 7 pages.

Notice of Allowance in U.S. Appl. No. 17/302,121, dated Nov. 15, 2021, 7 pages.

Notice of Allowance in U.S. Appl. No. 17/302,739, dated Mar. 30, 2022, 7 pages.

Notice of Allowance in U.S. Appl. No. 17/680,647, dated Apr. 27, 2023, 7 pages.

Rudgers et al., "EXZACTTM Precision Technology: Scientific and Regulatory Advancements in Plant-Genome Editing with ZFNs," NABC, 2014, pp. 113-124.

(56) References Cited

OTHER PUBLICATIONS

Shi et al., "ARGOS8 variants generated by CRISPR-Cas9 improve maize grain yield under field drought stress conditions," Plant Biotechnology Journal, 2017, vol. 15, pp. 207-216.
Yau et al., "Less is more: strategies to remove marker genes from transgenic plants," BMC Biotechnology, 2013, vol. 13, No. 36, pp. 1-23.
Zhang et al., "Off-target Effects in CRISPR/Cas9-mediated Genome Engineering," Molecular Therapy—Nucleic Acids, Nov. 17, 2015, vol. 4, pp. 1-8.
Zhong et al., "Plant Genome Editing Using FnCpf1 and LbCpf1 Nucleases at Redefined and Altered PAM Sites," Molecular Plant, Jul. 2018, vol. 11, No. 7, pp. 999-1002.
Zhong et al., "Supplementary Data—Plant Genome Editing Using FnCpf1 and LbCpf1 Nucleases at Redefined and Altered PAM Sites," Molecular Plant, Jul. 2018, vol. 11, No. 7, 36 pages.

\* cited by examiner

TGGGGGCTGCCTGTACTTCCCAAAACTTCGCTTCCCTGACCCATCATATCCAGGACTGGACGATTGGCTTGATTGAT
ACCAGATGGGTGAGTCGAGTCCACCTCGGTAGCGGCATTTATGGCAACGATTGCAGCCACGTTGACCTCCATCATT
TTTTCTCATGCTCATCATGGCCTCCATCATGGTGGTCATTTGGTCTTTCATGGCCTCCATGTCGGCCTTCATCTGCTC
TTGAACTTCATCTATCTCACTCATG ATTCTAGCCTTGGCACGTGTTTGGTAAGGGTACCGTAAAGCGCGTTCGTTCT
TTTTTATTACTATGATTACATTTTGACGATGATGATGATTGTAGGAAAGAATGAAATGAGTAATGAAACAACTAAA
TAAACGTGAATGCATGACAATGATAAGTTGCTGAAGTATTATAAATTTACATAGGACATTCAGTGGAACGTAGGGT
CGAATCAAATCCTATTTCATTAAAAACAATATTGTTCATCTTGACAGAGCCA AAGCATAACTAGAAATACAACATGG
ACACATCAGCGATTCCTAATTATGTGGGTCATTAGTTCGACCATGTGTTGGCAGTAACTTGAAAGACTATGAACTTC
ATCGGGAGCAGAGTATGTGTCAGTCACCGCCTTGGCTCTGGCTAACAACCTTGGGATCTCTTGGCTCTCATTTAGA
GTAAGAGCAAATTTGTCCATCCATTTCATGGCTTCTTTATGCAATAACTCTATCACCCCTTCTCTTGCTTCCCTTTCA A
CCTGCAAGGTCGACACTTTTGCCTGTTCGTCTTCTAGCCTTCGCCCATGACTAGCAGCTAGGTTCACCTTCTCTTCAT
ATTGGTCAATGATTATCAACATATTTTCTTTTGTTTTGCTCAACTGTTCTCTCAAACTTCTCTTCGATCTCTGACAACT
CTTTAACTTATCCTCTAACATCAGGTTTTCCATACTTGA *TTTGTCCCTCTTGGCTTTTCTAAGTTT*GAGCTCGTT*ACTG
CTGCCCCACAAAGCCCCTCGAAA*CTTGTTCCTGCTCCACTCTTCCTTTTGGGCTTTTTTGTTTCCCGCTCTAGCGCTTC
AATCGTGGTTATCAAGCTCcaaacactgatagt ttaaactgaaggcgggaaacgacaatctgatccccatcaagctctagctagagcggccg
cgttatcaagcttctgcaggtcctgctcgagtggaagctaattctcagtccaaagcctcaacaaggtcagggtacagagtctccaaaccattagccaa
aagctacaggagatcaatgaagaatcttcaatcaaagtaaactactgttccagcacatgcatcatggtcagtaagtttcagaaaaagacatccaccg
aagacttaaagttagtgggcatctttgaaagtaatcttgtcaacatcgagcagctggcttgtggggaccagacaaaaaaggaatggtgcagaattgtt
aggcgcacctaccaaaagcatctttgcctttattgcaaagataaagcagattcctctagtacaagtg gggaacaaaataacgtggaaaagagctgtc
ctgacagcccactcactaatgcgtatgacgaacgcagtgacgaccacaaaagaattagcttgagctcaggatttagcagcattccagattgggttcaa
tcaacaaggtacgagccatatcactttattcaaattggtatcgccaaaaccaagaaggaactcccatcctcaaaggtttgtaaggaagaattcgatat
caagcttgatatcggaagtttctctcttga gggaggttgctcgtggaatgggacacatatggttgttataataaaccatttccattgtcatgagattttga
ggttaatatatactttacttgttcattattttatttggtgtttgaataaatgatataaatggctcttgataatctgcattcattgagatatcaaatatttactc
tagagaagagtgtcatatagattgatggtccacaatcaatgaaattttttgggagacgaacatgtataaccatttgcttgaa taaccttaattaaaaggt
gtgattaaatgatgtttgtaacatgtagtactaaacattcataaaacacaaccaacccaagaggtattgagtattcacggctaaacaggggcataatg
gtaatttaaagaatgatatattttatgttaaaccctaacattggtttcggattcaacgctataaataaaaccactctcgttgctgattccatttatcgttct
tattgaccctagccgctacacacttttctgcgatatc tctgaggtaagcgttaacgtacccttagatcgttcttttctttttcgtctgctgatcgttgctcat
attatttcgatgattgttggattcgatgctctttgttgattgatcgttctgaaaattctgatctgttgtttagattttatcgattgttaatatcaacgtttcact
gcttctaaacgataaatttattcatgaaactattttcccattctgatcgatcttgttttgagattttaatttgttcgattgattg ttggttggtggatctatatac
gagtgaacttgttgatttgcgtatttaagatgtatgtcgatttgaattgtgattgggtaattctggagtagcataacaaatccagtgttcccttttctaag
ggtaattctcggattgtttgctttatatctcttgaaattgccgatttgattgaatttagctcgcttagctcagatgatagagcaccacaattttttgtggtaga
aatcggtttgactccgatagcggctttta ctatgattgttttgtgttaaagatgattttcataatggttatatatgtctactgttttattgattcaatatttg
attgttcttttttttgcagatttgttgaccagagatctaccatggcgcaagttagcagaatctgcaatggtgtgcagaacccatctcttatctccaatctct
cgaaatccagtcaacgcaaatctcccttatcggtttctctgaagacgcagcagcatccacgagcttatccgatttcgtc gtcgtggggattgaagaaga
gtgggatgacgttaattggctctgagcttcgtcctcttaaggtcatgtcttctgtttccacggcgtgcatgcttcacggtgcaagcagccgtccagcaact
gctcgtaagtcctctggtctttctggaaccgtccgtattccaggtgacaagtctatctcccacaggtccttcatgtttggaggtctcgctagcggtgaaac
tcgtatcaccggtcttttggaaggtgaagatgtt atcaacactggtaaggctatgcaagctatgggtgccagaatccgtaaggaaggtgatacttggat
cattgatggtgttggtaacggtggactccttgctcctgaggctcctctcgatttcggtaacgctgcaactggttgccgtttgactatgggtcttgttggtgtt
tacgatttcgatagcactttcattggtgacgcttctctcactaagcgtccaatgggtcgtgtgttgaacccacttcgcgaaatgggtg tgcaggtgaagtc
tgaagacggtgatcgtcttccagttaccttgcgtggaccaaagactccaacgccaatcacctacagggtacctatggcttccgctcaagtgaagtccgc
tgttctgcttgctggtctcaacaccccaggtatcaccactgttatcgagccaatcatgactcgtgaccacactgaaaagatgcttcaaggttttggtgcta
accttaccgttgagactgatgctgacggtgtgcgtaccatccg tcttgaaggtcgtggtaagctcaccggtcaagtgattgatgttccaggtgatccatc
ctctactgctttcccattggttgctgccttgcttgttccaggttccgacgtcaccatccttaacgttttgatgaacccaacccgtactggtctcatcttgact
ctgcaggaaatgggtgccgacatcgaagtgatcaacccacgtcttgctggtggagaagacgtggctgacttgcgtgttcgttcttctactttgaag ggt

*FIG. 1A* gttactgttccagaagaccgtgctccttctatgatcgacgagtatccaattctcgctgttgcagctgcattcgctgaaggtgctaccgttatgaacggttt
ggaagaactccgtgttaaggaaagcgaccgtctttctgctgtcgcaaacggtctcaagctcaacggtgttgattgcgatgaaggtgagacttctctcgt
cgtgcgtggtcgtcctgacggtaagggtctcggtaacgcttctggagcagctg tcgctacccacctcgatcaccgtatcgctatgagcttcctcgttatg
ggtctcgtttctgaaaaccctgttactgttgatgatgctactatgatcgctactagcttcccagagttcatggatttgatggctggtcttggagctaagatc
gaactctccgacactaaggctgcttgatgagctcaagaattcgagctcggtaccggatcctctagctagagctttcgttcgtatcatcggtttcgacaac
gttcgtcaagttcaatgcatcagtttcattgcgcacacaccagaatcctactgagtttgagtattatggcattgggaaaactgtttttcttgtaccatttgt
tgtgcttgtaatttactgtgttttttattcggttttcgctatcgaactgtgaaatggaaatggatggagaagagttaatgaatgatatggtccttttgttcat
tctcaaattaatattatttgtttttctcttatttgttgtgtgttgaatttgaaatta taagagatatgcaaacattttgttttgagtaaaaatgtgtcaaatc
gtggcctctaatgaccgaagttaatatgaggagtaaaacacttgtagttgtaccattatgcttattcactaggcaacaaatatattttcagacctagaaa
agctgcaaatgttactgaatacaagtatgtcctcttgtgttttagacatttatgaactttcctttatgtaattttccagaatccttgtcagattctaatcattg
ctttataattatagttatactcatggatttgtagttgagtatgaaaatattttttaatgcattttatgacttgccaattgattgacaacatgcatcaatcgac
ctgcagccactcgaagcggccgcatcgatcgtgaagtttctcatctaagcccccatttggacgtgaatgtagacacgtcgaaataaagatttccgaatt
agaataatttgtttattgctttcgcctataaatacga *cggatcgtaatttgtcgttttat caga*atgtac*tttcatttta taataacgctCAGACTC*TA
GTGACTACCACCTTCACTCTCCTCAAGCATTTCAGCCTCTTCCCCGCTCAGACTCCTTAGCTTTGGGAGCCAAATTAT
CCCTTACGTTCTCGACTTCAACCATATGTGATAGCTGCCTATGATACCATGGCTACTTCCCCTTAGTTCTTTATCTTTC
CTTTCCGCTTTATTCCATGCCTTACCGATCCTCTGAAGTGTCTTTGCATTAGCTTCATTG AAACCTCACGCGATGAAA
GGTGTGATGGTCTCCTCCGATGGCGCACTTCTCATAGGGTAACCTAATTGTCTTACGACCAACATAGGATTATAATT
AATACAACCCCTCGTCCCTATAAAAGGGACATTTGGAAATCCTTCACATAAGCATAACACTCCTACCCCTCTTTCTTT
CCACTGTGGGAACCAACTAATGGACGCTCCTATCATGCCTGCCAAGAGTTCTTCCCAATTTGCCTCGTCCTTTCCTG
AGCACATGCGATGACCTTGTATGGGGTAGACAGATCTACTTTCATGATTGAAGACGTGGGATACCAACCACACATA
AAGAGCAGGCGCACAACAGAAAATCCTCGTAGTGCTCTTCTTGCATCTTAAGTCAAATGTATCATACACTTATGCTA
AAACAACAATGATCGGGCTTTCCTTGCTATGGTGATAAGCAAGAAAAGCATCGATTGCTACTAGATCCACCAACTC
GTCTACATTCGAAAATAGTACTATCCCAAACAC TAGCAGTGCTAATACGTCGATGAATGATGCCCACTCTCCTTGGC
TGGCCAGAGTTTCCGCCTTCTCCTCCAATCACTTCCTTGGTATTCCCCCTACCCTATTCCTACTTTGCTTCACTCAGTC
TAATTCTCATTTCGAGATCTTGACAACTCCTGCTATTCTCGCCATAGAAGGATAGTACCCAGAAAAAAGGTATGGCT
TCCTTCCTCCTATCGGGCATCCTAAGATCCCTTCGAACTCCTCTATGGTTGGTGCT AACTGAAAGTCCCCAAAAGTG
AAGCATCTGAGTGATTGGTCATAGTATTGGGTGAGAGATGCGATG

FIG. 1B

TGGGGGCTGCCTGTACTTCCCAAAACTTCGCTTCCCTGACCCATCATATCCAGGACTGGACGATTGGCTTGATTGAT
ACCAGATGGGTGAGTCGAGTCCACCTCGGTAGCGGCATTTATGGCAACGATTGCAGCCACGTTGACCTCCATCATT
TTTTCTCATGCTCATCAT GGCCTCCATCATGGTGGTCATTTGGTCTTTCATGGCCTCCATGTCGGCCTTCATCTGCTC
TTGAACTTCATCTATCTCACTCATGATTCTAGCCTTGGCACGTGTTTGGTAAGGGTACCGTAAAGCGCGTTCGTTCT
TTTTTATTACTATGATTACATTTTGACGATGATGATGATTGTAGGAAAGAATGAAATGAGTAATGAAACAACTAAA
TAAACGTGAATGCATGACAATGATAAGTTGCTGAAGTATTATA AATTTACATAGGACATTCAGTGGAACGTAGGGT
CGAATCAAATCCTATTTCATTAAAAACAATATTGTTCATCTTGACAGAGCCAAAGCATAACTAGAAATACAACATGG
ACACATCAGCGATTCCTAATTATGTGGGTCATTAGTTCGACCATGTGTTGGCAGTAACTTGAAAGACTATGAACTTC
ATCGGGAGCAGAGTATGTGTCAGTCACCGCCTTGGCTCTGGCTAACAACCTTGGGATCTCTTGGCTCTC ATTTAGA
GTAAGAGCAAATTTGTCCATCCATTTCATGGCTTCTTTATGCAATAACTCTATCACCCCTTCTCTTGCTTCCCTTTCAA
CCTGCAAGGTCGACACTTTTGCCTGTTCGTCTTCTAGCCTTCGCCCATGACTAGCAGCTAGGTTCACCTTCTCTTCAT
ATTGGTCAATGATTATCAACATATTTTCTTTTGTTTTGCTCAACTGTTCTCTCAAACTTCTCTTCGATCTCTGACAACT
CTTTAACTTATCCTCTAACATCAGGTTTTCCATACTTGATTTGTCCCTCTTGGCTTTTCTAAGTTTGAGCTCGTT ACTG
CTGCCCCACAAAGCCCCTCGAAACTTGTTCCTGCTCCACTCTTCCTTTTGGGCTTTTTTGTTTCCCGCTCTAGCGCTTC
AATCGTGGTTATCAAGCTCcaaacactga tagtttaaactgaaggcgggaaacgacaatctgatccccatcaagctctagctagagcggccg
cgttatcaagcttctgcag gtcctgctcgagtggaagctaattctcagtccaaagcctcaacaaggtcagggtacagagtctccaaaccattagccaa
aagctacaggagatcaatgaagaatcttcaatcaaagtaaactactgttccagcacatgcatcatggtcagtaagtttcagaaaaagacatccaccg
aagacttaaagttagtgggcatctttgaaagtaatcttgtcaacatcgagcagctggcttgtggggaccagacaaaaaag gaatggtgcagaattgtt
aggcgcacctaccaaaagcatctttgcctttattgcaaagataaagcagattcctctagtacaagtggggaacaaaataacgtggaaaagagctgtc
ctgacagcccactcactaatgcgtatgacgaacgcagtgacgaccacaaaagaattagcttgagctcaggatttagcagcattccagattgggttcaa
tcaacaaggtacgagccatatcactttattcaaattggtatcg ccaaaaccaagaaggaactcccatcctcaaaggtttgtaaggaagaattcgatat
caagcttgatatcggaagtttctctcttgagggaggttgctcgtggaatgggacacatatggttgttataataaaccatttccattgtcatgagattttga
ggttaatatatactttacttgttcattatttttatttggtgtttgaataaatgatataaatggctcttgataatctgcattcattgagatatcaaatattt actc
tagagaagagtgtcatatagattgatggtccacaatcaatgaaattttttgggagacgaacatgtataaccatttgcttgaataaccttaattaaaaggt
gtgattaaatgatgtttgtaacatgtagtactaaacattcataaaacacaaccaacccaagaggtattgagtattcacggctaaacaggggcataatg
gtaatttaaagaatgatatattttatgttaaaccctaacattggtttcggattc aacgctataaataaaaccactctcgttgctgattccatttatcgttct
tattgaccctagccgctacacacttttctgcgatatctctgaggtaagcgttaacgtacccttagatcgttctttttcttttcgtctgctgatcgttgctcat
attatttcgatgattgttggattcgatgctctttgttgattgatcgttctgaaaattctgatctgttgtttagattttatcgattgttaatatcaacgtttcac t
gcttctaaacgataatttattcatgaaactattttcccattctgatcgatcttgttttgagattttaatttgttcgattgattgttggttggtggatctatatac
gagtgaacttgttgatttgcgtatttaagatgtatgtcgatttgaattgtgattgggtaattctggagtagcataacaaatccagtgttccctttttctaag
ggtaattctcggattgtttgctttatatctcttgaaattgccgatttg attgaatttagctcgcttagctcagatgatagagcaccacaatttttgtggtaga
aatcggtttgactccgatagcggcttttactatgattgttttgtgttaaagatgattttcataatggttatatatgtctactgttttttattgattcaatatttg
attgttctttttttttgcagatttgttgaccagagatctaccatggcgcaagttagcagaatctgcaatggtgtgcagaacccatctcttatctcca atctct
cgaaatccagtcaacgcaaatctcccttatcggtttctctgaagacgcagcagcatccacgagcttatccgatttcgtcgtcgtggggattgaagaaga
gtgggatgacgttaattggctctgagcttcgtcctcttaaggtcatgtcttctgtttccacggcgtgcatgcttcacggtgcaagcagccgtccagcaact
gctcgtaagtcctctggtctttctggaaccgtccgtattccaggtgacaa gtctatctcccacaggtccttcatgtttggaggtctcgctagcggtgaaac
tcgtatcaccggtcttttggaaggtgaagatgttatcaacactggtaaggctatgcaagctatgggtgccagaatccgtaaggaaggtgatacttggat
cattgatggtgttggtaacggtggactccttgctcctgaggctcctctcgatttcggtaacgctgcaactggttgccgtttgactatgggtcttgttggtgtt
tacgatttcgatagcactttcattggtgacgcttctctcactaagcgtccaatgggtcgtgtgttgaacccacttcgcgaaatgggtgtgcaggtgaagtc
tgaagacggtgatcgtcttccagttaccttgcgtggaccaaagactccaacgccaatcacctacagggtacctatggcttccgctcaagtgaagtccgc
tgttctgcttgctggtctcaacaccccaggtatcaccactgttatcgagccaatcatga ctcgtgaccacactgaaaagatgcttcaaggttttggtgcta
accttaccgttgagactgatgctgacggtgtgcgtaccatccgtcttgaaggtcgtggtaagctcaccggtcaagtgattgatgttccaggtgatccatc
ctctactgctttcccattggttgctgccttgcttgttccaggttccgacgtcaccatccttaacgttttgatgaacccaacccgtactggtctcatcttgact

FIG. 2A ctgcaggaaatgggtgccgacatcgaagtgatcaacccacgtcttgctggtggagaagacgtggctgacttgcgtgttcgttcttctactttgaagggt
gttactgttccagaagaccgtgctccttctatgatcgacgagtatccaattctcgctgttgcagctgcattcgctgaaggtgctaccgttatgaacggttt
ggaagaactccgtgttaaggaaagcgaccgtctttctgctgtcgcaaacggtctcaagctcaacggt gttgattgcgatgaaggtgagacttctctcgt
cgtgcgtggtcgtcctgacggtaagggtctcggtaacgcttctggagcagctgtcgctacccacctcgatcaccgtatcgctatgagcttcctcgttatg
ggtctcgtttctgaaaaccctgttactgttgatgatgctactatgatcgctactagcttcccagagttcatggatttgatggctggtcttggagctaagatc
gaactctccgacactaaggctgcttgatgagctcaagaattcgagctcggtaccggatcctctagctagagctttcgttcgtatcatcggtttcgacaac
gttcgtcaagttcaatgcatcagtttcattgcgcacacaccagaatcctactgagtttgagtattatggcattgggaaaactgttttcttgtaccatttgt
tgtgcttgtaatttactgtgttttttattcggttttcgctatcgaactgtgaaatggaaatggatggagaagagtt aatgaatgatatggtccttttgttcat
tctcaaattaatattatttgtttttctcttatttgttgtgtgttgaatttgaaattataagagatatgcaaacattttgttttgagtaaaaatgtgtcaaatc
gtggcctctaatgaccgaagttaatatgaggagtaaaacacttgtagttgtaccattatgcttattcactaggcaacaaatatattttcagacctagaaa
agctgcaaatgttactgaatacaagtatgtcctcttgtgttttagacatttatgaactttcctttatgtaattttccagaatccttgtcagattctaatcattg
ctttataattatagttatactcatggatttgtagttgagtatgaaaatattttttaatgcattttatgacttgccaattgattgacaacatgcatcaatcgac
ctgcagccactcgaagcggccgcatcgatcgtgaagtttctcatctaagcccccatttggacgtgaatgtagac acgtcgaaataaagatttccgaatt
agaataatttgtttattgctttcgcctataaatacgacggatcgtaatttgtcgttttatcaaaatgtactttcatttta taataacgctCAGACTCTA
TTTAACTTATCCTCTAACATCAGGTTTGTGACTACCACCTTCACTCTCCTCAAGCATTTCAGCCTCTTCCCCGCTCAG
ACTCCTTAGCTTTGGGAGCCAAATTATCCCTTACGTTCTGACTTCAACCATA TGTGATAGCTGCCTATGATACCAT
GGCTACTTCCCCTTAGTTCTTTATCTTTCCTTTCCGCTTTATTCCATGCCTTACCGATCCTCTGAAGTGTCTTTGCATTA
GCTTCATTGAAACCTCACGCGATGAAAGGTGTGATGGTCTCCTCCGATGGCGCACTTCTCATAGGGTAACCTAATT
GTCTTACGACCAACATAGGATTATAATTAATACAACCCCTCGTCCCTATAAAAGGGACATTTGGAAATCCTTCACA T
AAGCATAACACTCCTACCCCTCTTTCTTTCCACTGTGGGAACCAACTAATGGACGCTCCTATCATGCCTGCCAAGAG
TTCTTCCCAATTTGCCTCGTCCTTTCCTGAGCACATGCGATGACCTTGTATGGGGTAGACAGATCTACTTTCATGATT
GAAGACGTGGGATACCAACCACACATAAAGAGCAGGCGCACAACAGAAAATCCTCGTAGTGCTCTTCTTGCATCTT
AAGTCAAATGTATCATACACTTAT GCTAAAACAACAATGATCGGGCTTTCCTTGCTATGGTGATAAGCAAGAAAAG
CATCGATTGCTACTAGATCCACCAACTCGTCTACATTCGAAAATAGTACTATCCCAAACACTAGCAGTGCTAATACG
TCGATGAATGATGCCCACTCTCCTTGGCTGGCCAGAGTTTCCGCCTTCTCCTCCAATCACTTCCTTGGTATTCCCCCT
ACCCTATTCCTACTTTGCTTCACTCAGTCTAATTCTCATTTCGAGATCT TGACAACTCCTGCTATTCTCGCCATAGAAG
GATAGTACCCAGAAAAAGGTATGGCTTCCTTCCTCCTATCGGGCATCCTAAGATCCCTTCGAACTCCTCTATGGTT
GGTGCTAACTGAAAGTCCCCAAAAGTGAAGCATCTGAGTGATTGGTCATAGTATTGGGTGAGAGATGCGATG

*FIG. 2B*

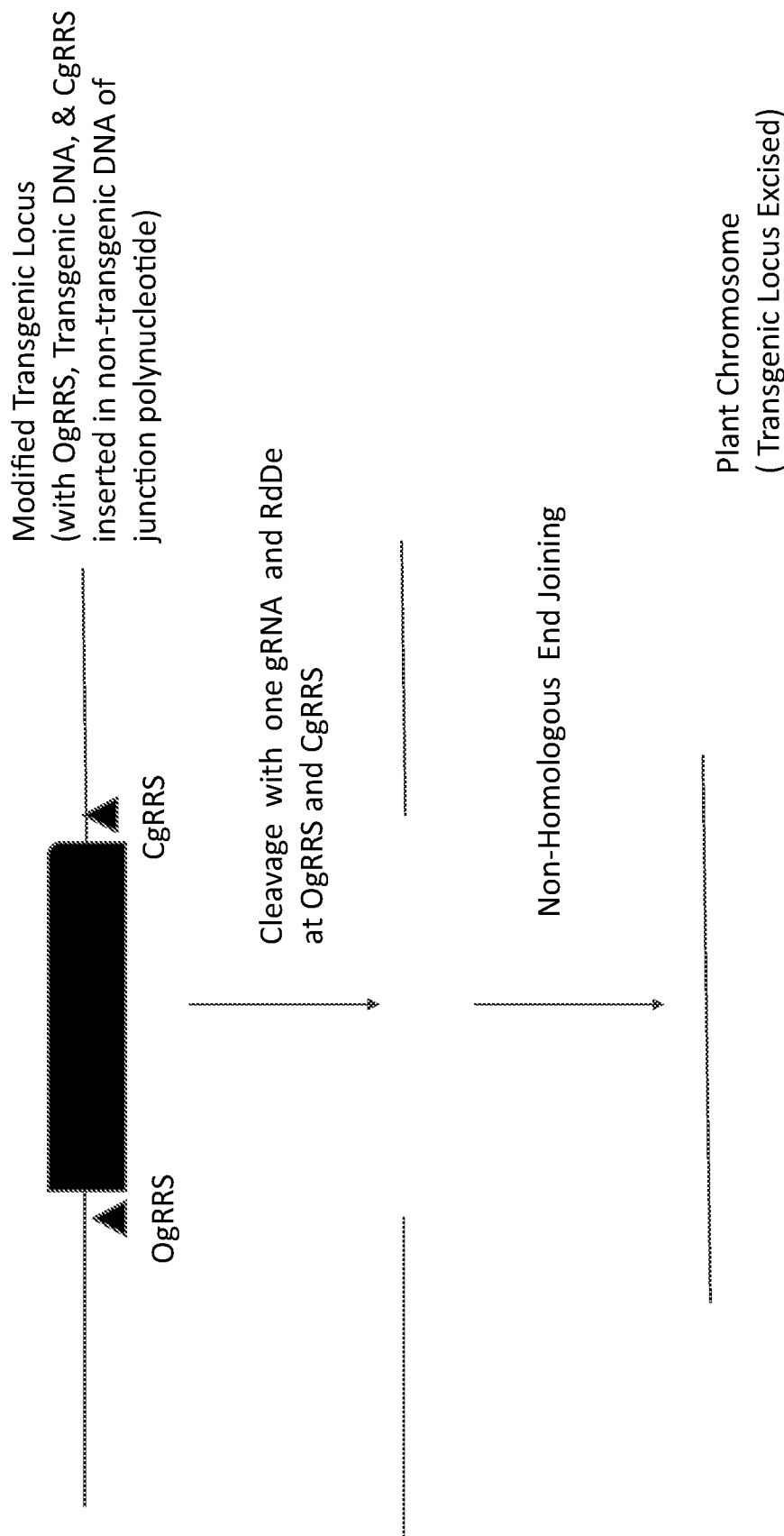

US 11,788,096 B2

EXCISABLE INHT31 TRANSGENIC SOYBEAN GLYPHOSATE TOLERANCE LOCUS

REFERENCE TO SEQUENCE LISTING SUBMITTED ELECTRONICALLY

The sequence listing contained in the file named "10088US1_ST25.txt", which is 30,515 bytes as measured in the Windows operating system, and which was created on Apr. 20, 2021 and electronically filed via EFS-Web on Apr. 23, 2021, is incorporated herein by reference in its entirety.

BACKGROUND

Transgenes which are placed into different positions in the plant genome through non-site specific integration can exhibit different levels of expression (Weising et al., 1988, Ann. Rev. Genet. 22:421-477). Such transgene insertion sites can also contain various undesirable rearrangements of the foreign DNA elements that include deletions and/or duplications. Furthermore, many transgene insertion sites can also comprise selectable or scoreable marker genes which in some instances are no longer required once a transgenic plant event containing the linked transgenes which confer desirable traits are selected.

Commercial transgenic plants typically comprise one or more independent insertions of transgenes at specific locations in the host plant genome that have been selected for features that include expression of the transgene(s) of interest and the transgene-conferred trait(s), absence or minimization of rearrangements, and normal Mendelian transmission of the trait(s) to progeny. An example of a selected transgenic soybean event which confers tolerance to glyphosate is the MON89788 transgenic soybean event disclosed in U.S. Pat. No. 9,944,945. MON89788 transgenic soybean plants express an *Agrobacterium* sp. strain CP4 EPSPS protein which can confer tolerance to glyphosate.

Methods for removing selectable marker genes and/or duplicated transgenes in transgene insertion sites in plant genomes involving use of site-specific recombinase systems (e.g., cre-lox) as well as for insertion of new genes into transgene insertion sites have been disclosed (Srivastava and Ow; Methods Mol Biol, 2015, 1287:95-103; Dale and Ow, 1991, *Proc. Natl Acad. Sci. USA* 88, 10558-10562; Srivastava and Thomson, Plant Biotechnol J, 2016; 14(2):471-82). Such methods typically require incorporation of the recombination site sequences recognized by the recombinase at particular locations within the transgene.

SUMMARY

Transgenic soybean plant cells comprising an INHT31 transgenic locus comprising an originator guide RNA recognition site (OgRRS) in a first DNA junction polynucleotide of a MON89788 transgenic locus and a cognate guide RNA recognition site (CgRRS) in a second DNA junction polynucleotide of the MON89788 transgenic locus are provided. Transgenic soybean plant cells comprising an INHT31 transgenic locus comprising an insertion and/or substitution in a DNA junction polynucleotide of a MON89788 transgenic locus of DNA comprising a cognate guide RNA recognition site (CgRRS) are provided. In certain embodiments, the MON89788 transgenic locus is set forth in SEQ ID NO:1, is present in seed deposited at the ATCC under accession No. PTA-6708 is present in progeny thereof, is present in allelic variants thereof, or is present in other variants thereof. INHT31 transgenic soybean plant cells, transgenic soybean plant seeds, and transgenic soybean plants all comprising a transgenic locus set forth in SEQ ID NO: 14 are provided. Transgenic soybean plant parts including seeds and transgenic soybean plants comprising the soybean plant cells are also provided.

Methods for obtaining a bulked population of inbred seed comprising selfing the aforementioned transgenic soybean plants and harvesting seed comprising the INHT31 transgenic locus from the selfed soybean plant are also provided.

Methods of obtaining hybrid soybean seed comprising crossing the aforementioned transgenic soybean plants to a second soybean plant which is genetically distinct from the first soybean plant and harvesting seed comprising the INHT31 transgenic locus from the cross are provided. Methods for obtaining a bulked population of seed comprising selfing a transgenic soybean plant of comprising SEQ ID NO: 14 and harvesting transgenic seed comprising the transgenic locus set forth in SEQ ID NO: 14 are provided.

A DNA molecule comprising SEQ ID NO: 14, 16, or 17 is provided. Processed transgenic soybean plant products and biological samples comprising the DNA molecules are provided. Nucleic acid molecules adapted for detection of genomic DNA comprising the DNA molecules, wherein said nucleic acid molecule optionally comprises a detectable label are provided. Methods of detecting a soybean plant cell comprising the INHT31 transgenic locus of any one of claims 1 to 3, comprising the step of detecting a DNA molecule comprising SEQ ID NO: 14, 16, or 17 are provided.

Methods of excising the INHT31 transgenic locus from the genome of the aforementioned soybean plant cells comprising the steps of: (a) contacting the edited transgenic plant genome of the plant cell with: (i) an RNA dependent DNA endonuclease (RdDe); and (ii) a guide RNA (gRNA) capable of hybridizing to the guide RNA hybridization site of the OgRRS and the CgRRS; wherein the RdDe recognizes a OgRRS/gRNA and a CgRRS/gRNA hybridization complex; and, (b) selecting a transgenic plant cell, transgenic plant part, or transgenic plant wherein the INHT31 transgenic locus flanked by the OgRRS and the CgRRS has been excised.

BRIEF DESCRIPTION OF THE DRAWINGS/FIGURES

FIG. 1A-B shows a sequence (SEQ ID NO: 1) of the MON89788 event transgenic locus including the endogenous genomic DNA (uppercase), transgenic insert DNA (lowercase) and 5' and 3' junction sequences flanking the transgenic insert DNA. The OgRRS sequence comprising the Protospacer Adjacent Motif (PAM) site (TTTA) and gRNA hybridization site (i.e., protospacer sequence; SEQ ID NO: 19) in the genomic DNA of the 5' junction sequence is shown in bold and underlined. The PAM sites and DNA sequence encoding the 5'_Guide-5 (SEQ ID NO: 24) gRNA and DNA targeted by 5'_Guide-1 (SEQ ID NO: 20) gRNA which are located in genomic DNA of the 5' junction polynucleotide sequence is in italics and double underlined. The PAM sites and DNA sequences encoding the 3'_Guide-2 (SEQ ID NO: 5) and 3'_Guide-5 (SEQ ID NO: 8) gRNAs which are located in or span the 3' junction polynucleotide sequence are in italics and double underlined. The 3'_Guide-2 gRNA is directed to transgenic DNA located in the transgene/soybean genomic DNA junction. The PAM site and DNA encoding the 3'_Guide-5 gRNA is located in transgenic DNA just 5' of the 3' junction polynucleotide.

FIG. 2A-B shows a sequence (SEQ ID NO: 14) of the INHT31 transgenic locus including the endogenous genomic DNA (uppercase) and transgenic insert DNA (lowercase) as well as the 5' and 3' junction sequences flanking the inserted transgenic DNA. The OgRRS sequence comprising the PAM site (TTTA) and gRNA hybridization site (SEQ ID NO: 19) in the genomic DNA of the 5' junction sequence is shown in bold and underlined. A CgRRS comprising the PAM site (TTTA) and gRNA hybridization site (SEQ ID NO: 19) located in the endogenous genomic DNA of the 3' junction polynucleotide is also shown in bold and underlined. The CgRRS as depicted can be introduced into the 3' junction polynucleotide as shown by using the Guide-5 gRNA hybridization site of SEQ ID NO: 8, a suitable Cas RdDe (e.g., a Cas12a nuclease of SEQ ID NO: 15), and the donor DNA template of SEQ ID NO: 11. The INHT31 transgenic locus can be excised with a single guide RNA which hybridizes to the SEQ ID NO: 19 gRNA hybridization site and a suitable Cas RdDe (e.g., a Cas12a nuclease of SEQ ID NO: 15) which will cleave DNA in both the OgRRS which flanks the 5' end of the INHT31 transgenic locus and the OgRRS which flanks the 3' end of the INHT31 transgenic locus.

FIG. 3 shows a schematic diagram which compares current breeding strategies for introgression of transgenic events (i.e., transgenic loci) to alternative breeding strategies for introgression of transgenic events where the transgenic events (i.e., transgenic loci) can be removed following introgression to provide different combinations of transgenic traits. In FIG. 3, "GE" refers to genome editing (e.g., including introduction of targeted genetic changes with genome editing molecules) and "Event Removal" refers to excision of a transgenic locus (i.e., an "Event") with genome editing molecules.

Figure 4A:
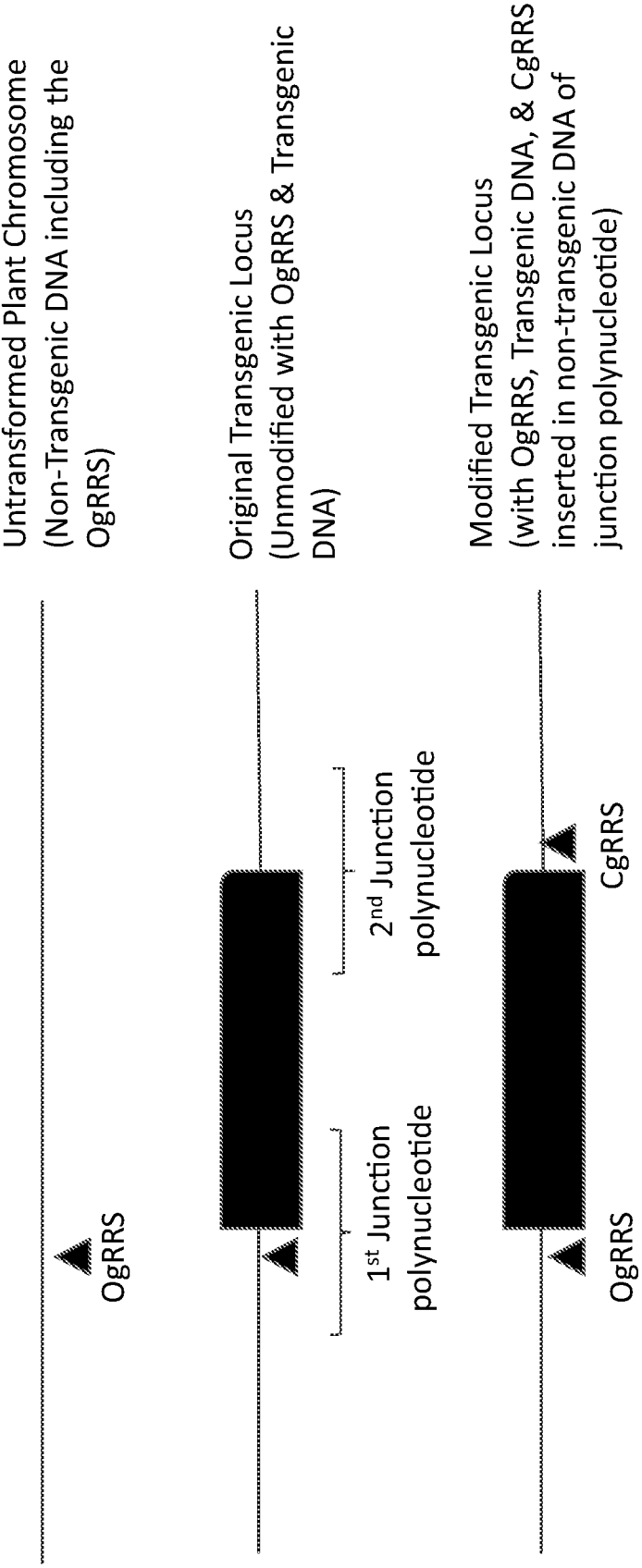
Figure 4C:
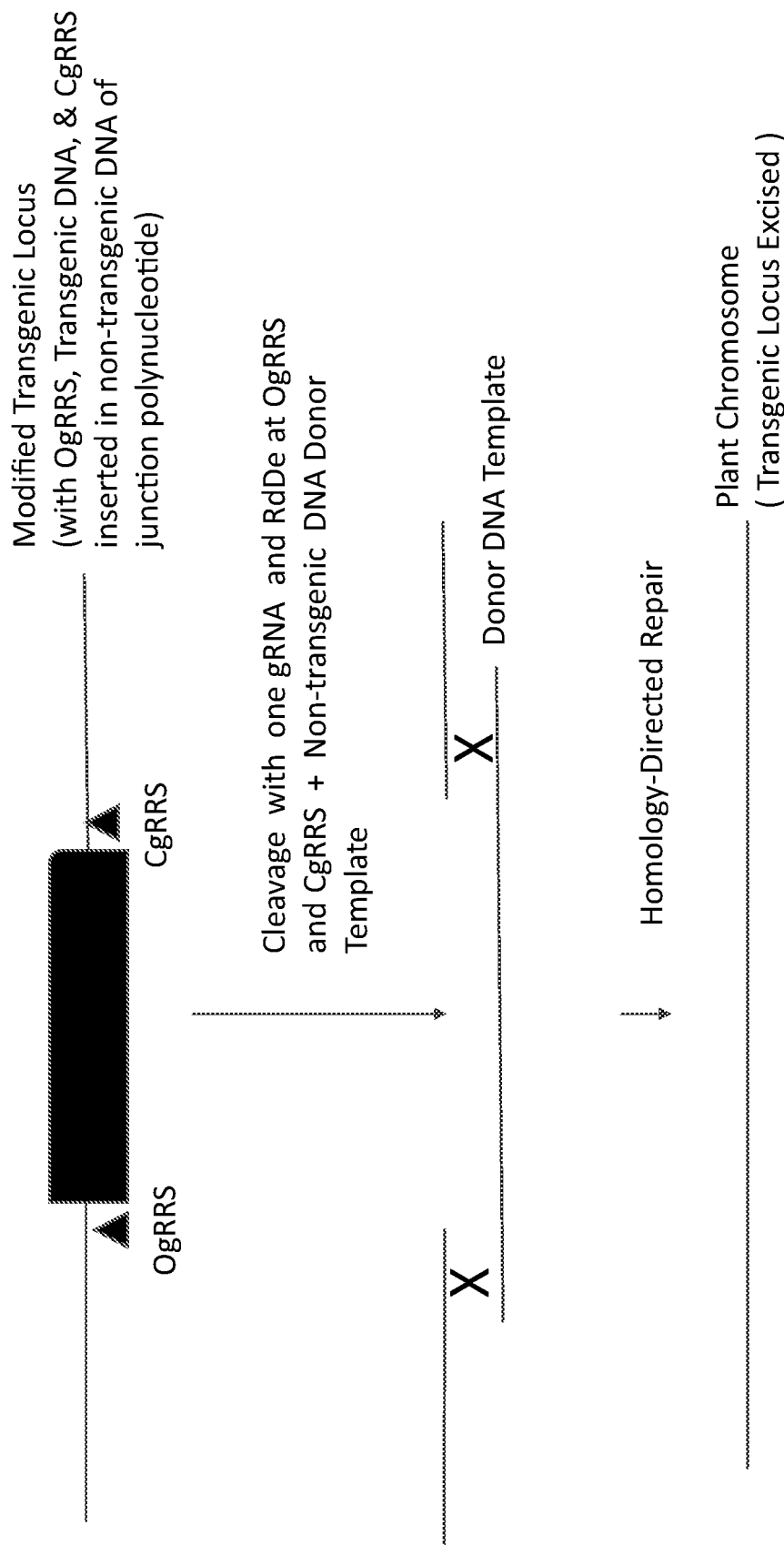

FIG. 4A, B, C. FIG. 4A shows a schematic diagram of a non-limiting example of: (i) an untransformed plant chromosome containing non-transgenic DNA which includes the originator guide RNA recognition site (OgRRS) (top); (ii) the original transgenic locus with the OgRRS in the non-transgenic DNA of the $1^{st}$ junction polynucleotide (middle); and (iii) the modified transgenic locus with a cognate guide RNA inserted into the non-transgenic DNA of the $2^{nd}$ junction polynucleotide (bottom). FIG. 4B shows a schematic diagram of a non-limiting example of a process where a modified transgenic locus with a cognate guide RNA inserted into the non-transgenic DNA of the $2^{nd}$ junction polynucleotide (top) is subjected to cleavage at the OgRRS and CgRRS with one guide RNA (gRNA) that hybridizes to gRNA hybridization site in both the OgRRS and the CgRRS and an RNA dependent DNA endonuclease (RdDe) that recognizes and cleaves the gRNA/OgRRS and the gRNA/CgRRS complex followed by non-homologous end joining processes to provide a plant chromosome where the transgenic locus is excised. FIG. 4C shows a schematic diagram of a non-limiting example of a process where a modified transgenic locus with a cognate guide RNA inserted into the non-transgenic DNA of the $2^{nd}$ junction polynucleotide (top) is subjected to cleavage at the OgRRS and CgRRS with one guide RNA (gRNA) that hybridizes to the gRNA hybridization site in both the OgRRS and the CgRRS and an RNA dependent DNA endonuclease (RdDe) that recognizes and cleaves the gRNA/OgRRS and the gRNA/CgRRS complex in the presence of a donor DNA template. In FIG. 4C, cleavage of the modified transgenic locus in the presence of the donor DNA template which has homology to non-transgenic DNA but lacks the OgRRS in the $1^{st}$ and $2^{nd}$ junction polynucleotides followed by homology-directed repair processes to provide a plant chromosome where the transgenic locus is excised and non-transgenic DNA present in the untransformed plant chromosome is at least partially restored.

DETAILED DESCRIPTION

Unless otherwise stated, nucleic acid sequences in the text of this specification are given, when read from left to right, in the 5' to 3' direction. Nucleic acid sequences may be provided as DNA or as RNA, as specified; disclosure of one necessarily defines the other, as well as necessarily defines the exact complements, as is known to one of ordinary skill in the art.

Where a term is provided in the singular, the inventors also contemplate embodiments described by the plural of that term.

The term "about" as used herein means a value or range of values which would be understood as an equivalent of a stated value and can be greater or lesser than the value or range of values stated by 10 percent. Each value or range of values preceded by the term "about" is also intended to encompass the embodiment of the stated absolute value or range of values.

The phrase "allelic variant" as used herein refers to a polynucleotide or polypeptide sequence variant that occurs in a different strain, variety, or isolate of a given organism.

The term "and/or" where used herein is to be taken as specific disclosure of each of the two specified features or components with or without the other. Thus, the term and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

As used herein, the phrase "approved transgenic locus" is a genetically modified plant event which has been authorized, approved, and/or de-regulated for any one of field testing, cultivation, human consumption, animal consumption, and/or import by a governmental body. Illustrative and non-limiting examples of governmental bodies which provide such approvals include the Ministry of Agriculture of Argentina, Food Standards Australia New Zealand, National Biosafety Technical Committee (CTNBio) of Brazil, Canadian Food Inspection Agency, China Ministry of Agriculture Biosafety Network, European Food Safety Authority, US Department of Agriculture, US Department of Environmental Protection, and US Food and Drug Administration.

The term "backcross", as used herein, refers to crossing an F1 plant or plants with one of the original parents. A backcross is used to maintain or establish the identity of one parent (species) and to incorporate a particular trait from a second parent (species). The term "backcross generation", as used herein, refers to the offspring of a backcross.

As used herein, the phrase "biological sample" refers to either intact or non-intact (e.g., milled seed or plant tissue, chopped plant tissue, lyophilized tissue) plant tissue. It may also be an extract comprising intact or non-intact seed or plant tissue. The biological sample can comprise flour, meal, syrup, oil, starch, and cereals manufactured in whole or in part to contain crop plant by-products. In certain embodiments, the biological sample is "non-regenerable" (i.e., incapable of being regenerated into a plant or plant part). In certain embodiments, the biological sample refers to a homogenate, an extract, or any fraction thereof containing genomic DNA of the organism from which the biological sample was obtained, wherein the biological sample does not comprise living cells.

As used herein, the terms "correspond," "corresponding," and the like, when used in the context of an nucleotide position, mutation, and/or substitution in any given polynucleotide (e.g., an allelic variant of SEQ ID NO: 1) with respect to the reference polynucleotide sequence (e.g., SEQ ID NO: 1) all refer to the position of the polynucleotide residue in the given sequence that has identity to the residue in the reference nucleotide sequence when the given polynucleotide is aligned to the reference polynucleotide sequence using a pairwise alignment algorithm (e.g., CLUSTAL O 1.2.4 with default parameters).

As used herein, the terms "Cpf1" and "Cas12a" are used interchangeably to refer to the same RNA dependent DNA endonuclease (RdDe). A Cas12a protein provided herein includes the protein of SEQ ID NO: 15.

The term "crossing" as used herein refers to the fertilization of female plants (or gametes) by male plants (or gametes). The term "gamete" refers to the haploid reproductive cell (egg or pollen) produced in plants by meiosis from a gametophyte and involved in sexual reproduction, during which two gametes of opposite sex fuse to form a diploid zygote. The term generally includes reference to a pollen (including the sperm cell) and an ovule (including the ovum). When referring to crossing in the context of achieving the introgression of a genomic region or segment, the skilled person will understand that in order to achieve the introgression of only a part of a chromosome of one plant into the chromosome of another plant, random portions of the genomes of both parental lines recombine during the cross due to the occurrence of crossing-over events in the production of the gametes in the parent lines. Therefore, the genomes of both parents must be combined in a single cell by a cross, where after the production of gametes from the cell and their fusion in fertilization will result in an introgression event.

As used herein, the phrases "DNA junction polynucleotide" and "junction polynucleotide" refers to a polynucleotide of about 18 to about 500 base pairs in length comprised of both endogenous chromosomal DNA of the plant genome and heterologous transgenic DNA which is inserted in the plant genome. A junction polynucleotide can thus comprise about 8, 10, 20, 50, 100, 200, 250, 500, or 1000 base pairs of endogenous chromosomal DNA of the plant genome and about 8, 10, 20, 50, 100, 200, 250, 500, or 1000 base pairs of heterologous transgenic DNA which span the one end of the transgene insertion site in the plant chromosomal DNA. Transgene insertion sites in chromosomes will typically contain both a 5' junction polynucleotide and a 3' junction polynucleotide. In embodiments set forth herein in SEQ ID NO: 1, the 5' junction polynucleotide is located at the 5' end of the sequence and the 3' junction polynucleotide is located at the 3' end of the sequence. In a non-limiting and illustrative example, a 5' junction polynucleotide of a transgenic locus is telomere proximal in a chromosome arm and the 3' junction polynucleotide of the transgenic locus is centromere proximal in the same chromosome arm. In another non-limiting and illustrative example, a 5' junction polynucleotide of a transgenic locus is centromere proximal in a chromosome arm and the 3' junction polynucleotide of the transgenic locus is telomere proximal in the same chromosome arm. The junction polynucleotide which is telomere proximal and the junction polynucleotide which is centromere proximal can be determined by comparing non-transgenic genomic sequence of a sequenced non-transgenic plant genome to the non-transgenic DNA in the junction polynucleotides.

The term "donor," as used herein in the context of a plant, refers to the plant or plant line from which the trait, transgenic event, or genomic segment originates, wherein the donor can have the trait, introgression, or genomic segment in either a heterozygous or homozygous state.

As used herein, the term "MON89788" is used to refer to any of a transgenic soybean locus, transgenic soybean plants and parts thereof including seed set forth in U.S. Pat. No. 9,944,945, which is incorporated herein by reference in its entirety. Representative MON89788 transgenic soybean seed have been deposited with American Type Culture Collection (ATCC, Manassas, Va. 20110-2209 USA) under Accession No. PTA-6708. MON89788 transgenic loci include loci having the sequence of SEQ ID NO:1, the sequence of the MON89788 locus in the deposited seed of Accession No. PTA-6708 and any progeny thereof, as well as allelic variants and other variants of SEQ ID NO:1.

As used herein, the terms "excise" and "delete," when used in the context of a DNA molecule, are used interchangeably to refer to the removal of a given DNA segment or element (e.g., transgene element or transgenic locus or portion thereof) of the DNA molecule.

As used herein, the phrase "elite crop plant" refers to a plant which has undergone breeding to provide one or more trait improvements. Elite crop plant lines include plants which are an essentially homozygous, e.g., inbred or doubled haploid. Elite crop plants can include inbred lines used as is or used as pollen donors or pollen recipients in hybrid seed production (e.g., used to produce F1 plants). Elite crop plants can include inbred lines which are selfed to produce non-hybrid cultivars or varieties or to produce (e.g., bulk up) pollen donor or recipient lines for hybrid seed production. Elite crop plants can include hybrid F1 progeny of a cross between two distinct elite inbred or doubled haploid plant lines.

As used herein, an "event," "a transgenic event," "a transgenic locus" and related phrases refer to an insertion of one or more transgenes at a unique site in the genome of a plant as well as to DNA fragments, plant cells, plants, and plant parts (e.g., seeds) comprising genomic DNA containing the transgene insertion. Such events typically comprise both a 5' and a 3' junction polynucleotide and confer one or more useful traits including herbicide tolerance, insect resistance, male sterility, and the like.

As used herein, the phrases "endogenous sequence," "endogenous gene," "endogenous DNA," "endogenous polynucleotide," and the like refer to the native form of a polynucleotide, gene or polypeptide in its natural location in the organism or in the genome of an organism.

The terms "exogenous" and "heterologous" as are used synonymously herein to refer to any polynucleotide (e.g., DNA molecule) that has been inserted into a new location in the genome of a plant. Non-limiting examples of an exogenous or heterologous DNA molecule include a synthetic DNA molecule, a non-naturally occurring DNA molecule, a DNA molecule found in another species, a DNA molecule found in a different location in the same species, and/or a DNA molecule found in the same strain or isolate of a species, where the DNA molecule has been inserted into a new location in the genome of a plant.

As used herein, the term "F1" refers to any offspring of a cross between two genetically unlike individuals.

The term "gene," as used herein, refers to a hereditary unit consisting of a sequence of DNA that occupies a specific location on a chromosome and that contains the genetic instruction for a particular characteristics or trait in an organism. The term "gene" thus includes a nucleic acid (for example, DNA or RNA) sequence that comprises coding sequences necessary for the production of an RNA, or a polypeptide or its precursor. A functional polypeptide can be encoded by a full length coding sequence or by any portion of the coding sequence as long as the desired activity or functional properties (e.g., enzymatic activity, pesticidal activity, ligand binding, and/or signal transduction) of the RNA or polypeptide are retained.

The term "identifying," as used herein with respect to a plant, refers to a process of establishing the identity or distinguishing character of a plant, including exhibiting a certain trait, containing one or more transgenes, and/or containing one or more molecular markers.

As used herein, the term "INHT31" is used to refer either individually collectively to items that include any or all of the MON89788 transgenic soybean loci which have been modified as disclosed herein, modified MON89788 transgenic soybean plants and parts thereof including seed, and DNA obtained therefrom.

The term "isolated" as used herein means having been removed from its natural environment.

As used herein, the terms "include," "includes," and "including" are to be construed as at least having the features to which they refer while not excluding any additional unspecified features.

As used herein, the phrase "introduced transgene" is a transgene not present in the original transgenic locus in the genome of an initial transgenic event or in the genome of a progeny line obtained from the initial transgenic event. Examples of introduced transgenes include exogenous transgenes which are inserted in a resident original transgenic locus.

As used herein, the terms "introgression", "introgressed" and "introgressing" refer to both a natural and artificial process, and the resulting plants, whereby traits, genes or DNA sequences of one species, variety or cultivar are moved into the genome of another species, variety or cultivar, by crossing those species. The process may optionally be completed by backcrossing to the recurrent parent. Examples of introgression include entry or introduction of a gene, a transgene, a regulatory element, a marker, a trait, a trait locus, or a chromosomal segment from the genome of one plant into the genome of another plant.

The phrase "marker-assisted selection", as used herein, refers to the diagnostic process of identifying, optionally followed by selecting a plant from a group of plants using the presence of a molecular marker as the diagnostic characteristic or selection criterion. The process usually involves detecting the presence of a certain nucleic acid sequence or polymorphism in the genome of a plant.

The phrase "molecular marker", as used herein, refers to an indicator that is used in methods for visualizing differences in characteristics of nucleic acid sequences. Examples of such indicators are restriction fragment length polymorphism (RFLP) markers, amplified fragment length polymorphism (AFLP) markers, single nucleotide polymorphisms (SNPs), microsatellite markers (e.g. SSRs), sequence-characterized amplified region (SCAR) markers, Next Generation Sequencing (NGS) of a molecular marker, cleaved amplified polymorphic sequence (CAPS) markers or isozyme markers or combinations of the markers described herein which defines a specific genetic and chromosomal location.

As used herein the terms "native" or "natural" define a condition found in nature. A "native DNA sequence" is a DNA sequence present in nature that was produced by natural means or traditional breeding techniques but not generated by genetic engineering (e.g., using molecular biology/transformation techniques).

The term "offspring", as used herein, refers to any progeny generation resulting from crossing, selfing, or other propagation technique.

The phrase "operably linked" refers to a juxtaposition wherein the components so described are in a relationship permitting them to function in their intended manner. For instance, a promoter is operably linked to a coding sequence if the promoter affects its transcription or expression. When the phrase "operably linked" is used in the context of a PAM site and a guide RNA hybridization site, it refers to a PAM site which permits cleavage of at least one strand of DNA in a polynucleotide with an RNA dependent DNA endonuclease or RNA dependent DNA nickase which recognize the PAM site when a guide RNA complementary to guide RNA hybridization site sequences adjacent to the PAM site is present. A OgRRS and its CgRRS are operably linked to junction polynucleotides when they can be recognized by a gRNA and an RdDe to provide for excision of the transgenic locus or portion thereof flanked by the junction polynucleotides.

As used herein, the term "plant" includes a whole plant and any descendant, cell, tissue, or part of a plant. The term "plant parts" include any part(s) of a plant, including, for example and without limitation: seed (including mature seed and immature seed); a plant cutting; a plant cell; a plant cell culture; or a plant organ (e.g., pollen, embryos, flowers, fruits, shoots, leaves, roots, stems, and explants). A plant tissue or plant organ may be a seed, protoplast, callus, or any other group of plant cells that is organized into a structural or functional unit. A plant cell or tissue culture may be capable of regenerating a plant having the physiological and morphological characteristics of the plant from which the cell or tissue was obtained, and of regenerating a plant having substantially the same genotype as the plant. Regenerable cells in a plant cell or tissue culture may be embryos, protoplasts, meristematic cells, callus, pollen, leaves, anthers, roots, root tips, silk, flowers, kernels, ears, cobs, husks, or stalks. In contrast, some plant cells are not capable of being regenerated to produce plants and are referred to herein as "non-regenerable" plant cells.

The term "purified," as used herein defines an isolation of a molecule or compound in a form that is substantially free of contaminants normally associated with the molecule or compound in a native or natural environment and means having been increased in purity as a result of being separated from other components of the original composition. The term "purified nucleic acid" is used herein to describe a nucleic acid sequence which has been separated from other compounds including, but not limited to polypeptides, lipids and carbohydrates.

The term "recipient", as used herein, refers to the plant or plant line receiving the trait, transgenic event or genomic segment from a donor, and which recipient may or may not have the have trait, transgenic event or genomic segment itself either in a heterozygous or homozygous state.

As used herein the term "recurrent parent" or "recurrent plant" describes an elite line that is the recipient plant line in a cross and which will be used as the parent line for successive backcrosses to produce the final desired line.

As used herein the term "recurrent parent percentage" relates to the percentage that a backcross progeny plant is identical to the recurrent parent plant used in the backcross. The percent identity to the recurrent parent can be determined experimentally by measuring genetic markers such as SNPs and/or RFLPs or can be calculated theoretically based on a mathematical formula.

The terms "selfed," "selfing," and "self," as used herein, refer to any process used to obtain progeny from the same plant or plant line as well as to plants resulting from the process. As used herein, the terms thus include any fertilization process wherein both the ovule and pollen are from the same plant or plant line and plants resulting therefrom. Typically, the terms refer to self-pollination processes and progeny plants resulting from self-pollination.

The term "selecting", as used herein, refers to a process of picking out a certain individual plant from a group of individuals, usually based on a certain identity, trait, characteristic, and/or molecular marker of that individual.

As used herein, the phrase "originator guide RNA recognition site" or the acronym "OgRRS" refers to an endogenous DNA polynucleotide comprising a protospacer adjacent motif (PAM) site operably linked to a guide RNA hybridization site (i.e., protospacer sequence). In certain embodiments, an OgRRS can be located in an untransformed plant chromosome or in non-transgenic DNA of a DNA junction polynucleotide of both an original transgenic locus and a modified transgenic locus. In certain embodiments, an OgRRS can be located in transgenic DNA of a DNA junction polynucleotide of both an original transgenic locus and a modified transgenic locus. In certain embodiments, an OgRRS can be located in both transgenic DNA and non-transgenic DNA of a DNA junction polynucleotide of both an original transgenic locus and a modified transgenic locus (i.e., can span transgenic and non-transgenic DNA in a DNA junction polynucleotide).

As used herein the phrase "cognate guide RNA recognition site" or the acronym "CgRRS" refer to a DNA polynucleotide comprising a PAM site operably linked to a guide RNA hybridization site (i.e., protospacer sequence), where the CgRRS is absent from transgenic plant genomes comprising a first original transgenic locus that is unmodified and where the CgRRS and its corresponding OgRRS can hybridize to a single gRNA. A CgRRS can be located in transgenic DNA of a DNA junction polynucleotide of a modified transgenic locus, in transgenic DNA of a DNA junction polynucleotide of a modified transgenic locus, or in both transgenic and non-transgenic DNA of a modified transgenic locus (i.e., can span transgenic and non-transgenic DNA in a DNA junction polynucleotide).

As used herein, the phrase "a transgenic locus excision site" refers to the DNA which remains in the genome of a plant or in a DNA molecule (e.g., an isolated or purified DNA molecule) wherein a segment comprising, consisting essentially of, or consisting of a transgenic locus has been deleted. In a non-limiting and illustrative example, a transgenic locus excision site can thus comprise a contiguous segment of DNA comprising at least 10 base pairs of DNA that is telomere proximal to the deleted transgenic locus or to the deleted segment of the transgenic locus and at least 10 base pairs of DNA that is centromere proximal to the deleted transgenic locus or to the deleted segment of the transgenic locus.

As used herein, the phrase "transgene element" refers to a segment of DNA comprising, consisting essentially of, or consisting of a promoter, a 5' UTR, an intron, a coding region, a 3'UTR, or a polyadenylation signal. Polyadenylation signals include transgene elements referred to as "terminators" (e.g., NOS, pinII, rbcs, Hsp17, TubA).

To the extent to which any of the preceding definitions is inconsistent with definitions provided in any patent or non-patent reference incorporated herein by reference, any patent or non-patent reference cited herein, or in any patent or non-patent reference found elsewhere, it is understood that the preceding definition will be used herein.

Genome editing molecules can permit introduction of targeted genetic change conferring desirable traits in a variety of crop plants (Zhang et al. Genome Biol. 2018; 19: 210; Schindele et al. FEBS Lett. 2018; 592(12):1954). Desirable traits introduced into crop plants such as soybean and soybean include herbicide tolerance, improved food and/or feed characteristics, male-sterility, and drought stress tolerance. Nonetheless, full realization of the potential of genome editing methods for crop improvement will entail efficient incorporation of the targeted genetic changes in germplasm of different elite crop plants adapted for distinct growing conditions. Such elite crop plants will also desirably comprise useful transgenic loci which confer various traits including herbicide tolerance, pest resistance (e.g.; insect, nematode, fungal disease, and bacterial disease resistance), conditional male sterility systems for hybrid seed production, abiotic stress tolerance (e.g., drought tolerance), improved food and/or feed quality, and improved industrial use (e.g., biofuel). Provided herein are methods whereby targeted genetic changes are efficiently combined with desired subsets of transgenic loci in elite progeny plant lines (e.g., elite inbreds used for hybrid seed production or for inbred varietal production). Also provided are plant genomes containing modified transgenic loci which can be selectively excised with a single gRNA molecule. Such modified transgenic loci comprise an originator guide RNA recognition site (OgRRS) which is identified in non-transgenic DNA of a first junction polynucleotide of the transgenic locus and cognate guide RNA recognition site (CgRRS) which is introduced (e.g., by genome editing methods) into a second junction polynucleotide of the transgenic locus and which can hybridize to the same gRNA as the OgRRS, thereby permitting excision of the modified transgenic locus with a single guide RNA. An originator guide RNA recognition site (OgRRS) comprises endogenous DNA found in untransformed plants and in endogenous non-transgenic DNA of junction polynucleotides of transgenic plants containing a modified or unmodified transgenic locus. The OgRRS located in non-transgenic DNA of a first DNA junction polynucleotide is used to design a related cognate guide RNA recognition site (CgRRS) which is introduced (e.g., by genome editing methods) into the second junction polynucleotide of the transgenic locus. A CgRRS is thus present in junction polynucleotides of modified transgenic loci provided herein and is absent from endogenous DNA found in untransformed plants and absent from endogenous non-transgenic DNA found in junction sequences of transgenic plants containing an unmodified transgenic locus. Also provided are unique transgenic locus excision sites created by excision of such modified transgenic loci, DNA molecules comprising the modified transgenic loci, unique transgenic locus excision sites and/or plants comprising the same, biological samples containing the DNA, nucleic acid markers adapted for detecting the DNA molecules, and related methods of identifying the elite crop plants comprising unique transgenic locus excision sites.

Also provided herein are methods whereby targeted genetic changes are efficiently combined with desired subsets of transgenic loci in elite progeny plant lines (e.g., elite inbreds used for hybrid seed production or for inbred varietal production). Examples of such methods include those illustrated in FIG. 3. In certain embodiments, INHT31 transgenic loci provided here are characterized by polynucleotide sequences that can facilitate as necessary the removal of the INHT31 transgenic loci from the genome. Useful applications of such INHT31 transgenic loci and related methods of making include targeted excision of a INHT31 transgenic locus or portion thereof in certain breeding lines to facilitate recovery of germplasm with subsets of transgenic traits tailored for specific geographic locations and/or grower preferences. Other useful applications of such INHT31 transgenic loci and related methods of making include removal of transgenic traits from certain breeding lines when it is desirable to replace the trait in the breeding line without disrupting other transgenic loci and/or non-transgenic loci. In certain embodiments, soybean genomes containing INHT31 transgenic loci or portions thereof which can be selectively excised with one or more gRNA molecules and RdDe (RNA dependent DNA endonucleases) which form gRNA/target DNA complexes. Such selectively excisable INHT31 transgenic loci can comprise an originator guide RNA recognition site (OgRRS) which is identified in non-transgenic DNA, transgenic DNA, or a combination thereof in of a first junction polynucleotide of the transgenic locus and cognate guide RNA recognition site (CgRRS) which is introduced (e.g., by genome editing methods) into a second junction polynucleotide of the transgenic locus and which can hybridize to the same gRNA as the OgRRS, thereby permitting excision of the modified transgenic locus or portions thereof with a single guide RNA (e.g., as shown in FIGS. 3A and B). In certain embodiments, an originator guide RNA recognition site (OgRRS) comprises endogenous DNA found in untransformed plants and in endogenous non-transgenic DNA of junction polynucleotides of transgenic plants containing a modified or unmodified transgenic locus. In certain embodiments, an originator guide RNA recognition site (OgRRS) comprises exogenous transgenic DNA of junction polynucleotides of transgenic plants containing a modified or unmodified transgenic locus. The OgRRS located in non-transgenic DNA transgenic DNA, or a combination thereof in of a first DNA junction polynucleotide is used to design a related cognate guide RNA recognition site (CgRRS) which is introduced (e.g., by genome editing methods) into the second junction polynucleotide of the transgenic locus. A CgRRS is thus present in junction polynucleotides of modified transgenic loci provided herein and is absent from endogenous DNA found in untransformed plants and absent from junction sequences of transgenic plants containing an unmodified transgenic locus. A CgRRS is also absent from a combination of non-transgenic and transgenic DNA found in junction sequences of transgenic plants containing an unmodified transgenic locus. An example of OgRRS polynucleotide sequences in or near a 5' junction polynucleotide in an MON89788 transgenic locus include SEQ ID NO: 18, which is shown in bold and underlined in FIG. 1. OgRRS polynucleotide sequences located in a first junction polynucleotide can be introduced into the second junction polynucleotide using donor DNA templates as illustrated in FIG. 4C and as elsewhere described herein. A donor DNA template for introducing the SEQ ID NO: 18 OgRRS into the 3' junction polynucleotide of an MON89788 locus includes the donor DNA template comprising SEQ ID NO: 11. Double stranded breaks in a 3' junction polynucleotide of SEQ ID NO: 1 can be introduced with the 3'_Guide-1, 3'_Guide-2, 3'_Guide-3, 3'_Guide-4, and/or 3'_Guide-5 gRNAs, each comprising RNAs which are respectively encoded by SEQ ID NO: 4, 5, 6, 7, and/or 8, and a Cas12a nuclease. In certain embodiments, double stranded breaks in a 3' junction polynucleotide of SEQ ID NO: 1 can be introduced with the 3'_Guide-1 or 2 gRNAs and the 3'_Guide-5 gRNAs and a Cas12a nuclease (e.g., a Cas12a nuclease of SEQ ID NO: 15). Integration of the SEQ ID NO: 11 donor DNA template comprising the CgRRS into the 3' junction polynucleotide of an MON89788 locus at the double stranded breaks introduced by the gRNAs comprising an RNA encoded by SEQ ID NO: 4, 5, 6, 7, and/or 8 and a Cas12a nuclease can provide an INHT31 locus comprising the CgRRS sequence set forth in SEQ ID NO: 16. A subsequence comprising the CgRRS which is located in the 3' junction polynucleotide of the INHT31 transgenic locus is set forth in SEQ ID NO: 17. Double stranded breaks in a 3' junction polynucleotide of SEQ ID NO: 1 can be introduced with gRNAs encoded by SEQ ID NO: 5 and a Cas12a nuclease. A donor DNA template of SEQ ID NO: 11 or the equivalent thereof having longer or shorter homology arms can be used to obtain the CgRRS insertion in the 3' junction polynucleotide that is set forth in SEQ ID NO: 16 and 17. An INHT31 transgenic locus containing this CgRRS insertion is set forth in SEQ ID NO: 14. In certain embodiments, such insertions of a CgRRS in a 3' junction polynucleotide of an INHT31 transgenic locus include those wherein one or more nucleotides in a segment corresponding to nucleotides 5397 to 5416 of SEQ ID NO: 1 are absent or independently selected from A, C, G, or T, with the proviso that the nucleotides present in the INHT31 locus are not identical to nucleotides 5397 to 5416 of SEQ ID NO: 1. In certain embodiments, other insertions of a CgRRS in a 5' junction polynucleotide of an INHT31 transgenic locus include those wherein one or more nucleotides in a segment corresponding to nucleotides 5397 to 5416 of SEQ ID NO: 1 are absent or independently selected from A, C, G, or T, with the proviso that the nucleotides present in the INHT31 locus are not identical to nucleotides 5397 to 5416 of SEQ ID NO: 1.

In certain embodiments, an INHT31 transgenic locus can further comprise modifications of a 5' junction polynucleotide of an MON89788 transgenic locus (e.g., as set forth in SEQ ID NO: 1, FIG. 1, and Example 1). Such modifications of the 5' junction polynucleotide of an MON89788 transgenic locus can be effected by introducing double stranded breaks in the locus with the 5'_Guide-1, 5'_Guide-2, 5'_Guide-3, 5'_Guide-4, and/or 3'_Guide-5 gRNAs, each comprising RNAs which are respectively encoded by SEQ ID NO: 20, 21, 22, 23, and/or 24, and a Cas12a nuclease. In certain embodiments, the modifications comprise introduction of the double stranded breaks followed by non-homologous end joining (NHEJ) either in the presence or absence of a donor DNA template that lacks homology to the site of the double stranded break. In certain embodiments, the modifications comprise introduction of the double stranded breaks followed by homology-directed repair (HDR) with a donor DNA template with homology to DNA flanking the site of the double stranded break. Such modifications of junction polynucleotides include deletions of DNA segments comprising non-essential transgenic DNA in the 5' junction polynucleotide (e.g., one or more residues corresponding to nucleotides 1 to 204 of SEQ ID NO: 2). In certain embodiments, such deletions of non-essential DNA of a 5' junction polynucleotide of an INHT31 transgenic locus include those wherein one or more nucleotides in a segment corresponding to nucleotides 1094 to 1113 of SEQ ID NO: 1 are absent or independently selected from A, C, G, or T, with the proviso that the nucleotides present in the INHT31 locus are not identical to 1094 nucleotides to 1113 of SEQ ID NO: 1. In certain embodiments, insertions of a CgRRS in a 5' junction polynucleotide of an INHT31 transgenic locus include those wherein one or more nucleotides in a 3' junction fragment segment corresponding to nucleotides 5397 to 5416 of SEQ ID NO: 1 are absent or independently selected from A, C, G, or T, with the proviso that the nucleotides present in the INHT31 locus are not identical to nucleotides 5397 to 5416 of SEQ ID NO: 1.

Also provided are unique transgenic locus excision sites created by excision of INHT31 transgenic loci or selectively excisable INHT31 transgenic loci, DNA molecules comprising the INHT31 transgenic loci or unique fragments thereof (i.e., fragments of an INHT31 locus which are not found in an MON89788 transgenic locus), INHT31 plants comprising the same, biological samples containing the DNA, nucleic acid markers adapted for detecting the DNA molecules, and related methods of identifying soybean plants comprising unique INHT31 transgenic locus excision sites and unique fragments of a INHT31 transgenic locus. An example of such an excision site would include an excision site created by excising the INHT31 transgenic locus with a guide RNA encoded by SEQ ID NO:19 and a suitable Cas RdDe (e.g., a Cas12a nuclease of SEQ ID NO: 15). DNA molecules comprising unique fragments of an INHT31 transgenic locus are diagnostic for the presence of an INHT31 transgenic locus or fragments thereof in a soybean plant, soybean cell, soybean seed, products obtained therefrom (e.g., seed meal or stover), and biological samples. DNA molecules comprising unique fragments of an INHT31 transgenic locus include DNA molecules comprising the CgRRS include SEQ ID NO: 17.

Methods provided herein can be used to excise any transgenic locus where the first and second junction sequences comprising the endogenous non-transgenic genomic DNA and the heterologous transgenic DNA which are joined at the site of transgene insertion in the plant genome are known or have been determined. In certain embodiments provided herein, transgenic loci can be removed from crop plant lines to obtain crop plant lines with tailored combinations of transgenic loci and optionally targeted genetic changes. Such first and second junction sequences are readily identified in new transgenic events by inverse PCR techniques using primers which are complementary the inserted transgenic sequences. In certain embodiments, the first and second junction sequences of transgenic loci are published. An example of a transgenic locus which can be improved and used in the methods provided herein is the soybean MON89788 transgenic locus. The soybean MON89788 transgenic locus and its transgenic junction sequences are also depicted in FIG. 1. Soybean plants comprising the MON89788 transgenic locus and seed thereof have been cultivated, been placed in commerce, and have been described in a variety of publications by various governmental bodies. Databases which have compiled descriptions of the MON89788 transgenic locus include the International Service for the Acquisition of Agri-biotech Applications (ISAAA) database (available on the world wide web internet site "isaaa.org/gmapprovaldatabase/event"), the GenBit LLC database (available on the world wide web internet site "genbitgroup.com/en/gmo/gmodatabase"), and the Biosafety Clearing-House (BCH) database (available on the http internet site "bch.cbd.int/database/organisms").

Sequences of the junction polynucleotides as well as the transgenic insert(s) of the MON89788 transgenic locus which can be improved by the methods provided herein are set forth or otherwise provided in SEQ ID NO: 1, U.S. Pat. No. 9,944,945, the sequence of the MON89788 locus in the deposited seed of ATCC accession No. PTA-6708, and elsewhere in this disclosure. In certain embodiments provided herein, the MON89788 transgenic locus set forth in SEQ ID NO: 1 or present in the deposited seed of ATCC accession No. PTA-6708 is referred to as an "original MON89788 transgenic locus." Allelic or other variants of the sequence set forth SEQ ID NO: 1, the patent references set forth therein and incorporated herein by reference in their entireties, and elsewhere in this disclosure which may be present in certain variant MON89788 transgenic plant loci (e.g., progeny of deposited seed of accession No. PTA-6708 which contain allelic variants of SEQ ID NO:1 or progeny originating from transgenic plant cells comprising the original MIR162 transgenic set forth in U.S. Pat. No. 9,944,945) can also be improved by identifying sequences in the variants that correspond to the SEQ ID NO: 1 by performing a pairwise alignment (e.g., using CLUSTAL O 1.2.4 with default parameters) and making corresponding changes in the allelic or other variant sequences. Such allelic or other variant sequences include sequences having at least 85%, 90%, 95%, 98%, or 99% sequence identity across the entire length or at least 20, 40, 100, 500, 1,000, 2,000, 4,000, 5,000, 6,000, or 6466 nucleotides of SEQ ID NO: 1. Also provided are plants, plant parts including seeds, genomic DNA, and/or DNA obtained from INHT31 plants which comprise one or more modifications (e.g., via insertion of a CgRRS in a junction polynucleotide sequence) which provide for selective excision of the INHT31 transgenic locus or a portion thereof. Also provided herein are methods of detecting plants, genomic DNA, and/or DNA obtained from plants comprising a INHT31 transgenic locus which contains one or more of a CgRRS, deletions of non-essential DNA, and/or a transgenic locus excision site. A first junction polynucleotide of a MON89788 transgenic locus can comprise either one of the junction polynucleotides found at the 5' end or the 3' end of any one of the sequences set forth in SEQ ID NO: 1, allelic variants thereof, or other variants thereof. An OgRRS can be found within non-transgenic DNA, transgenic DNA, or a combination thereof in either one of the junction polynucleotides of any one of SEQ ID NO: 1, allelic variants thereof, or other variants thereof. A second junction polynucleotide of a transgenic locus can comprise either one of the junction polynucleotides found at the 5' or 3' end of any one of the sequences set forth in SEQ ID NO: 1, allelic variants thereof, or other variants thereof. A CgRRS can be introduced within transgenic, non-transgenic DNA, or a combination thereof of either one of the junction polynucleotides of any one of SEQ ID NO: 1, allelic variants thereof, or other variants thereof to obtain an INHT31 transgenic locus. In certain embodiments, the OgRRS is found in non-transgenic DNA or transgenic DNA of the 5' junction polynucleotide of a transgenic locus of any one of SEQ ID NO: 1, allelic variants thereof, or other variants thereof and the corresponding CgRRS is introduced into the transgenic DNA, non-transgenic DNA, or a combination thereof in the 3' junction polynucleotide of the MON89788 transgenic locus of SEQ ID NO: 1, allelic variants thereof, or other variants thereof to obtain an INHT31 transgenic locus. In other embodiments, the OgRRS is found in non-transgenic DNA or transgenic DNA of the 3' junction polynucleotide of the MON89788 transgenic locus of any one of SEQ ID NO: 1, allelic variants thereof, or other variants thereof and the corresponding CgRRS is introduced into the transgenic DNA, non-transgenic DNA, or a combination thereof in the 5' junction polynucleotide of the transgenic locus of SEQ ID NO: 1, allelic variants thereof, or other variants thereof to obtain an INHT31 transgenic locus.

In certain embodiments, the CgRRS is comprised in whole or in part of an exogenous DNA molecule that is introduced into a DNA junction polynucleotide by genome editing. In certain embodiments, the guide RNA hybridization site of the CgRRS is operably linked to a pre-existing PAM site in the transgenic DNA or non-transgenic DNA of the transgenic plant genome. In other embodiments, the guide RNA hybridization site of the CgRRS is operably linked to a new PAM site that is introduced in the DNA junction polynucleotide by genome editing. A CgRRS can be located in non-transgenic plant genomic DNA of a DNA junction polynucleotide of an INHT31 transgenic locus, in transgenic DNA of a DNA junction polynucleotide of an INHT31 transgenic locus or can span the junction of the transgenic and non-transgenic DNA of a DNA junction polynucleotide of an INHT31 transgenic locus. An OgRRS can likewise be located in non-transgenic plant genomic DNA of a DNA junction polynucleotide of an INHT31 transgenic locus, in transgenic DNA of a DNA junction polynucleotide of an INHT31 transgenic locus, or can span the junction of the transgenic and non-transgenic DNA of a DNA junction polynucleotide of an INHT31 transgenic locus Methods provided herein can be used in a variety of breeding schemes to obtain elite crop plants comprising subsets of desired modified transgenic loci comprising an OgRRS and a CgRRS operably linked to junction polynucleotide sequences and transgenic loci excision sites where undesired transgenic loci or portions thereof have been removed (e.g., by use of the OgRRS and a CgRRS). Such methods are useful at least insofar as they allow for production of distinct useful donor plant lines each having unique sets of modified transgenic loci and, in some instances, targeted genetic changes that are tailored for distinct geographies and/or product offerings. In an illustrative and non-limiting example, a different product lines comprising transgenic loci conferring only two of three types of herbicide tolerance (e.g., glyphosate, glufosinate, and dicamba) can be obtained from a single donor line comprising three distinct transgenic loci conferring resistance to all three herbicides. In certain aspects, plants comprising the subsets of undesired transgenic loci and transgenic loci excision sites can further comprise targeted genetic changes. Such elite crop plants can be inbred plant lines or can be hybrid plant lines. In certain embodiments, at least two transgenic loci (e.g., transgenic loci including an INHT31 and another modified transgenic locus wherein an OgRRS and a CgRRS site is operably linked to a first and a second junction sequence and optionally non-essential DNA is deleted) are introgressed into a desired donor line comprising elite crop plant germplasm and then subjected to genome editing molecules to recover plants comprising one of the two introgressed transgenic loci as well as a transgenic loci excision site introduced by excision of the other transgenic locus or portion thereof by the genome editing molecules. In certain embodiments, the genome editing molecules can be used to remove a transgenic locus and introduce targeted genetic changes in the crop plant genome. Introgression can be achieved by backcrossing plants comprising the transgenic loci to a recurrent parent comprising the desired elite germplasm and selecting progeny with the transgenic loci and recurrent parent germplasm. Such backcrosses can be repeated and/or supplemented by molecular assisted breeding techniques using SNP or other nucleic acid markers to select for recurrent parent germplasm until a desired recurrent parent percentage is obtained (e.g., at least about 95%, 96%, 97%, 98%, or 99% recurrent parent percentage). A non-limiting, illustrative depiction of a scheme for obtaining plants with both subsets of transgenic loci and the targeted genetic changes is shown in the FIG. 3 (bottom "Alternative" panel), where two or more of the transgenic loci ("Event" in FIG. 3) are provided in Line A and then moved into elite crop plant germplasm by introgression. In the non-limiting FIG. 3 illustration, introgression can be achieved by crossing a "Line A" comprising two or more of the modified transgenic loci to the elite germplasm and then backcrossing progeny of the cross comprising the transgenic loci to the elite germplasm as the recurrent parent) to obtain a "Universal Donor" (e.g., Line A+ in FIG. 3) comprising two or more of the modified transgenic loci. This elite germplasm containing the modified transgenic loci (e.g., "Universal Donor" of FIG. 3) can then be subjected to genome editing molecules which can excise at least one of the transgenic loci ("Event Removal" in FIG. 3) and introduce other targeted genetic changes ("GE" in FIG. 3) in the genomes of the elite crop plants containing one of the transgenic loci and a transgenic locus excision site corresponding to the removal site of one of the transgenic loci. Such selective excision of transgenic loci or portion thereof can be effected by contacting the genome of the plant comprising two transgenic loci with gene editing molecules (e.g., RdDe and gRNAs, TALENS, and/or ZFN) which recognize one transgenic loci but not another transgenic loci. Genome editing molecules that provide for selective excision of a first modified transgenic locus comprising an OgRRS and a CgRRS include a gRNA that hybridizes to the OgRRS and CgRRS of the first modified transgenic locus and an RdDe that recognizes the gRNA/OgRRS and gRNA/CgRRS complexes. Distinct plant lines with different subsets of transgenic loci and desired targeted genetic changes are thus recovered (e.g., "Line B-1," "Line B-2," and "Line B-3" in FIG. 3). In certain embodiments, it is also desirable to bulk up populations of inbred elite crop plants or their seed comprising the subset of transgenic loci and a transgenic locus excision site by selfing. In certain embodiments, inbred progeny of the selfed soybean plants comprising the INHT31 transgenic loci can be used as a pollen donor or recipient for hybrid seed production. Such hybrid seed and the progeny grown therefrom can comprise a subset of desired transgenic loci and a transgenic loci excision site.

Hybrid plant lines comprising elite crop plant germplasm, at least one transgenic locus and at least one transgenic locus excision site, and in certain aspects, additional targeted genetic changes are also provided herein. Methods for production of such hybrid seed can comprise crossing elite crop plant lines where at least one of the pollen donor or recipient comprises at least the transgenic locus and a transgenic locus excision site and/or additional targeted genetic changes. In certain embodiments, the pollen donor and recipient will comprise germplasm of distinct heterotic groups and provide hybrid seed and plants exhibiting heterosis. In certain embodiments, the pollen donor and recipient can each comprise a distinct transgenic locus which confers either a distinct trait (e.g., herbicide tolerance or insect resistance), a different type of trait (e.g., tolerance to distinct herbicides or to distinct insects such as coleopteran or lepidopteran insects), or a different mode-of-action for the same trait (e.g., resistance to coleopteran insects by two distinct modes-of-action or resistance to lepidopteran insects by two distinct modes-of-action). In certain embodiments, the pollen recipient will be rendered male sterile or conditionally male sterile. Methods for inducing male sterility or conditional male sterility include emasculation (e.g., detasseling), cytoplasmic male sterility, chemical hybridizing agents or systems, a transgenes or transgene systems, and/or mutation(s) in one or more endogenous plant genes. Descriptions of various male sterility systems that can be adapted for use with the elite crop plants provided herein are described in Wan et al. Molecular Plant; 12, 3, (2019):321-342 as well as in U.S. Pat. No. 8,618,358; US 20130031674; and US 2003188347.

In certain embodiments, edited transgenic plant genomes, transgenic plant cells, parts, or plants containing those genomes, and DNA molecules obtained therefrom, can comprise a desired subset of transgenic loci and/or comprise at least one transgenic locus excision site. In certain embodiments, a segment comprising an INHT31 transgenic locus comprising an OgRRS in non-transgenic DNA of a 1st junction polynucleotide sequence and a CgRRS in a 2nd junction polynucleotide sequence is deleted with a gRNA and RdDe that recognize the OgRRS and the CgRRS to produce an INHT31 transgenic locus excision site. For example, an INHT31 transgenic locus set forth in SEQ ID NO: 14 can be deleted with a Cas12a RdDe (e.g. the Cas12a of SEQ ID NO: 15) and a gRNA comprising an RNA encoded by SEQ ID NO: 19. In certain embodiments, the transgenic locus excision site can comprise a contiguous segment of DNA comprising at least 10 base pairs of DNA that is telomere proximal to the deleted segment of the transgenic locus and at least 10 base pairs of DNA that is centromere proximal to the deleted segment of the transgenic locus wherein the transgenic DNA (i.e., the heterologous DNA) that has been inserted into the crop plant genome has been deleted. In certain embodiments where a segment comprising a transgenic locus has been deleted, the transgenic locus excision site can comprise a contiguous segment of DNA comprising at least 10 base pairs DNA that is telomere proximal to the deleted segment of the transgenic locus and at least 10 base pairs of DNA that is centromere proximal DNA to the deleted segment of the transgenic locus wherein the heterologous transgenic DNA and at least 1, 2, 5, 10, 20, 50, or more base pairs of endogenous DNA located in a 5' junction sequence and/or in a 3' junction sequence of the original transgenic locus that has been deleted. In such embodiments where DNA comprising the transgenic locus is deleted, a transgenic locus excision site can comprise at least 10 base pairs of DNA that is telomere proximal to the deleted segment of the transgenic locus and at least 10 base pairs of DNA that is centromere proximal to the deleted segment of the transgenic locus wherein all of the transgenic DNA is absent and either all or less than all of the endogenous DNA flanking the transgenic DNA sequences are present. In certain embodiments where a segment consisting essentially of an original transgenic locus has been deleted, the transgenic locus excision site can be a contiguous segment of at least 10 base pairs of DNA that is telomere proximal to the deleted segment of the transgenic locus and at least 10 base pairs of DNA that is centromere proximal to the deleted segment of the transgenic locus wherein less than all of the heterologous transgenic DNA that has been inserted into the crop plant genome is excised. In certain aforementioned embodiments where a segment consisting essentially of an original transgenic locus has been deleted, the transgenic locus excision site can thus contain at least 1 base pair of DNA or 1 to about 2 or 5, 8, 10, 20, or 50 base pairs of DNA comprising the telomere proximal and/or centromere proximal heterologous transgenic DNA that has been inserted into the crop plant genome. In certain embodiments where a segment consisting of an original transgenic locus has been deleted, the transgenic locus excision site can contain a contiguous segment of DNA comprising at least 10 base pairs of DNA that is telomere proximal to the deleted segment of the transgenic locus and at least 10 base pairs of DNA that is centromere proximal to the deleted segment of the transgenic locus wherein the heterologous transgenic DNA that has been inserted into the crop plant genome is deleted. In certain embodiments where DNA consisting of the transgenic locus is deleted, a transgenic locus excision site can comprise at least 10 base pairs of DNA that is telomere proximal to the deleted segment of the transgenic locus and at least 10 base pairs of DNA that is centromere proximal to the deleted segment of the transgenic locus wherein all of the heterologous transgenic DNA that has been inserted into the crop plant genome is deleted and all of the endogenous DNA flanking the heterologous sequences of the transgenic locus is present. In any of the aforementioned embodiments or in other embodiments, the continuous segment of DNA comprising the transgenic locus excision site can further comprise an insertion of 1 to about 2, 5, 10, 20, or more nucleotides between the DNA that is telomere proximal to the deleted segment of the transgenic locus and the DNA that is centromere proximal to the deleted segment of the transgenic locus. Such insertions can result either from endogenous DNA repair and/or recombination activities at the double stranded breaks introduced at the excision site and/or from deliberate insertion of an oligonucleotide. Plants, edited plant genomes, biological samples, and DNA molecules (e.g., including isolated or purified DNA molecules) comprising the INHT31 transgenic loci excision sites are provided herein.

In other embodiments, a segment comprising a INHT31 transgenic locus (e.g., a transgenic locus comprising an OgRRS in non-transgenic DNA of a $1^{st}$ junction sequence and a CgRRS in a $2^{nd}$ junction sequence) can be deleted with a gRNA and RdDe that recognize the OgRRS and the CgRRS (e.g., the Cas12a RdDe of SEQ ID NO: 15 and a gRNA comprising an RNA encoded by SEQ ID NO: 19) and replaced with DNA comprising the endogenous non-transgenic plant genomic DNA present in the genome prior to transgene insertion. A non-limiting example of such replacements can be visualized in FIG. 4C, where the donor DNA template can comprise the endogenous non-transgenic plant genomic DNA present in the genome prior to transgene insertion along with sufficient homology to non-transgenic DNA on each side of the excision site to permit homology-directed repair. In certain embodiments, the endogenous non-transgenic plant genomic DNA present in the genome prior to transgene insertion can be at least partially restored. In certain embodiments, the endogenous non-transgenic plant genomic DNA present in the genome prior to transgene insertion can be essentially restored such that no more than about 5, 10, or 20 to about 50, 80, or 100 nucleotides are changed relative to the endogenous DNA at the essentially restored excision site.

In certain embodiments, edited transgenic plant genomes and transgenic plant cells, plant parts, or plants containing those edited genomes, comprising a modification of an original transgenic locus, where the modification comprises an OgRRS and a CgRRS which are operably linked to a $1^{st}$ and a $2^{nd}$ junction sequence, respectively or irrespectively, and optionally further comprise a deletion of a segment of the original transgenic locus. In certain embodiments, the modification comprises two or more separate deletions and/or there is a modification in two or more original transgenic plant loci. In certain embodiments, the deleted segment comprises, consists essentially of, or consists of a segment of non-essential DNA in the transgenic locus. Illustrative examples of non-essential DNA include but are not limited to synthetic cloning site sequences, duplications of transgene sequences; fragments of transgene sequences, and Agrobacterium right and/or left border sequences. In certain embodiments, the non-essential DNA is a duplication and/or fragment of a promoter sequence and/or is not the promoter sequence operably linked in the cassette to drive expression of a transgene. In certain embodiments, excision of the non-essential DNA improves a characteristic, functionality, and/or expression of a transgene of the transgenic locus or otherwise confers a recognized improvement in a transgenic plant comprising the edited transgenic plant genome. In certain embodiments, the non-essential DNA does not comprise DNA encoding a selectable marker gene. In certain embodiments of an edited transgenic plant genome, the modification comprises a deletion of the non-essential DNA. In certain embodiments of an edited transgenic plant genome, prior to excision, the segment to be deleted is flanked by operably linked protospacer adjacent motif (PAM) sites in the original or unmodified transgenic locus and/or the segment to be deleted encompasses an operably linked PAM site in the original or unmodified transgenic locus. In certain embodiments, following excision of the segment, the resulting edited transgenic plant genome comprises PAM sites flanking the deletion site in the modified transgenic locus. In certain embodiments of an edited transgenic plant genome, the modification comprises a modification of a MON89788 transgenic locus. In certain embodiments, non-essential DNA located in a 5' junction polynucleotide (e.g., SEQ ID NO: 2) or a 3' junction polynucleotide of a MON89788 locus is excised in an INHT31 locus. Methods for excision of non-essential DNA in a 5' junction polynucleotide or a 3' junction polynucleotide of a MON89788 locus include those disclosed in Examples 1 and 2, respectively.

In certain embodiments, improvements in a transgenic plant locus are obtained by introducing a new cognate guide RNA recognition site (CgRRS) which is operably linked to a DNA junction polynucleotide of the transgenic locus in the transgenic plant genome. Such CgRRS sites can be recognized by RdDe and a single suitable guide RNA directed to the CgRRS and the originator gRNA Recognition Site (OgRRS) to provide for cleavage within the junction polynucleotides which flank an INHT31 transgenic locus. In certain embodiments, the CgRRS/gRNA and OgRRS/gRNA hybridization complexes are recognized by the same class of RdDe (e.g., Class 2 type II or Class 2 type V) or by the same RdDe (e.g., both the CgRRS/gRNA and OgRRS/gRNA hybridization complexes recognized by the same Cas9 or Cas 12 RdDe). Such CgRRS and OgRRS can be recognized by RdDe and suitable guide RNAs containing crRNA sufficiently complementary to the guide RNA hybridization site DNA sequences adjacent to the PAM site of the CgRRS and the OgRRS to provide for cleavage within or near the two junction polynucleotides. Suitable guide RNAs can be in the form of a single gRNA comprising a crRNA or in the form of a crRNA/tracrRNA complex. In the case of the OgRRS site, the PAM and guide RNA hybridization site are endogenous DNA polynucleotide molecules found in the plant genome. In certain embodiments where the CgRRS is introduced into the plant genome by genome editing, gRNA hybridization site polynucleotides introduced at the CgRRS are at least 17 or 18 nucleotides in length and are complementary to the crRNA of a guide RNA. In certain embodiments, the gRNA hybridization site sequence of the OgRRS and/or the CgRRS is about 17 or 18 to about 24 nucleotides in length. The gRNA hybridization site sequence of the OgRRS and the gRNA hybridization site of the CgRRS can be of different lengths or comprise different sequences so long as there is sufficient complementarity to permit hybridization by a single gRNA and recognition by a RdDe that recognizes and cleaves DNA at the gRNA/OgRRS and gRNA/CgRRS complex. In certain embodiments, the guide RNA hybridization site of the CgRRS comprise about a 17 or 18 to about 24 nucleotide sequence which is identical to the guide RNA hybridization site of the OgRRS. In other embodiments, the guide RNA hybridization site of the CgRRS comprise about a 17 or 18 to about 24 nucleotide sequence which has one, two, three, four, or five nucleotide insertions, deletions or substitutions when compared to the guide RNA hybridization site of the OgRRS. Certain CgRRS comprising a gRNA hybridization site containing has one, two, three, four, or five nucleotide insertions, deletions or substitutions when compared to the guide RNA hybridization site of the OgRRS can undergo hybridization with a gRNA which is complementary to the OgRRS gRNA hybridization site and be cleaved by certain RdDe. Examples of mismatches between gRNAs and guide RNA hybridization sites which allow for RdDe recognition and cleavage include mismatches resulting from both nucleotide insertions and deletions in the DNA which is hybridized to the gRNA (e.g., Lin et al., doi: 10.1093/nar/gku402). In certain embodiments, an operably linked PAM site is co-introduced with the gRNA hybridization site polynucleotide at the CgRRS. In certain embodiments, the gRNA hybridization site polynucleotides are introduced at a position adjacent to a resident endogenous PAM sequence in the junction polynucleotide sequence to form a CgRRS where the gRNA hybridization site polynucleotides are operably linked to the endogenous PAM site. In certain embodiments, non-limiting features of the OgRRS, CgRRS, and/or the gRNA hybridization site polynucleotides thereof include: (i) absence of significant homology or sequence identity (e.g., less than 50% sequence identity across the entire length of the OgRRS, CgRRS, and/or the gRNA hybridization site sequence) to any other endogenous or transgenic sequences present in the transgenic plant genome or in other transgenic genomes of the soybean plant being transformed and edited; (ii) absence of significant homology or sequence identity (e.g., less than 50% sequence identity across the entire length of the sequence) of a sequence of a first OgRRS and a first CgRRS to a second OgRRS and a second CgRRS which are operably linked to junction polynucleotides of a distinct transgenic locus; (iii) the presence of some sequence identity (e.g., about 25%, 40%, or 50% to about 60%, 70%, or 80%) between the OgRRS sequence and endogenous sequences present at the site where the CgRRS sequence is introduced; and/or (iv) optimization of the gRNA hybridization site polynucleotides for recognition by the RdDe and guide RNA when used in conjunction with a particular PAM sequence. In certain embodiments, the first and second OgRRS as well as the first and second CgRRS are recognized by the same class of RdDe (e.g., Class 2 type II or Class 2 type V) or by the same RdDe (e.g., Cas9 or Cas 12 RdDe). In certain embodiments, the first OgRRS site in a first junction polynucleotide and the CgRRS introduced in the second junction polynucleotide to permit excision of a first transgenic locus by a first single guide RNA and a single RdDe. Such nucleotide insertions or genome edits used to introduce CgRRS in a transgenic plant genome can be effected in the plant genome by using gene editing molecules (e.g., RdDe and guide RNAs, RNA dependent nickases and guide RNAs, Zinc Finger nucleases or nickases, or TALE nucleases or nickases) which introduce blunt double stranded breaks or staggered double stranded breaks in the DNA junction polynucleotides. In the case of DNA insertions, the genome editing molecules can also in certain embodiments further comprise a donor DNA template or other DNA template which comprises the heterologous nucleotides for insertion to form the CgRRS. Guide RNAs can be directed to the junction polynucleotides by using a pre-existing PAM site located within or adjacent to a junction polynucleotide of the transgenic locus. Non-limiting examples of such pre-existing PAM sites present in junction polynucleotides, which can be used either in conjunction with an inserted heterologous sequence to form a CgRRS or which can be used to create a double stranded break to insert or create a CgRRS, include PAM sites recognized by a Cas12a enzyme. Non-limiting examples where a CgRRS is created in a DNA sequence are illustrated in Example 2 and FIG. 2.

Transgenic loci comprising OgRRS and CgRRS in a first and a second junction polynucleotides can be excised from the genomes of transgenic plants by contacting the transgenic loci with RdDe or RNA directed nickases, and a suitable guide RNA directed to the OgRRS and CgRRS (e.g., the Cas12a RdDe of SEQ ID NO: 15 and a gRNA comprising an RNA encoded by SEQ ID NO: 19). A non-limiting example where a modified transgenic locus is excised from a plant genome by use of a gRNA and an RdDe that recognizes an OgRRS/gRNA and a CgRRS/gRNA complex and introduces dsDNA breaks in both junction polynucleotides and repaired by NHEJ is depicted in FIG. 4B. In the depicted example set forth in FIG. 4B, the OgRRS site and the CgRRS site are absent from the plant chromosome comprising the transgene excision site that results from the process. In other embodiments provided herein where a modified transgenic locus is excised from a plant genome by use of a gRNA and an RdDe that recognizes an OgRRS/gRNA and a CgRRS/gRNA complex and repaired by NHEJ or microhomology-mediated end joining (MMEJ), the OgRRS and/or other non-transgenic sequences that were originally present prior to transgene insertion are partially or essentially restored.

Original MON89788 transgenic loci (events), including those set forth in SEQ ID NO: 1), U.S. Pat. No. 9,944,945, the sequence of the MON89788 locus in the deposited seed of accession No. PTA-6708 and progeny thereof, contain a selectable marker gene encoding a CP4 EPSPS protein which confers tolerance to the herbicide glyphosate. This CP$ EPSPS selectable marker gene also confers useful tolerance to glyphosate.

In certain embodiments, edited transgenic plant genomes provided herein can comprise additional new introduced transgenes (e.g., expression cassettes) inserted into the transgenic locus of a given event. Introduced transgenes inserted at the transgenic locus of an event subsequent to the event's original isolation can be obtained by inducing a double stranded break at a site within an original transgenic locus (e.g., with genome editing molecules including an RdDe and suitable guide RNA(s); a suitable engineered zinc-finger nuclease; a TALEN protein and the like) and providing an exogenous transgene in a donor DNA template which can be integrated at the site of the double stranded break (e.g. by homology-directed repair (HDR) or by non-homologous end-joining (NHEJ)). In certain embodiments, an OgRRS and a CgRRS located in a 1$^{st}$ junction polynucleotide and a 2$^{nd}$ junction polynucleotide, respectively, can be used to delete the transgenic locus and replace it with one or more new expression cassettes. In certain embodiments, such deletions and replacements are effected by introducing dsDNA breaks in both junction polynucleotides and providing the new expression cassettes on a donor DNA template (e.g., in FIG. 4C, the donor DNA template can comprise an expression cassette flanked by DNA homologous to non-transgenic DNA located telomere proximal and centromere proximal to the excision site). Suitable expression cassettes for insertion include DNA molecules comprising promoters which are operably linked to DNA encoding proteins and/or RNA molecules which confer useful traits which are in turn operably linked to polyadenylation sites or terminator elements. In certain embodiments, such expression cassettes can also comprise 5' UTRs, 3' UTRs, and/or introns. Useful traits include biotic stress tolerance (e.g., insect resistance, nematode resistance, or disease resistance), abiotic stress tolerance (e.g., heat, cold, drought, and/or salt tolerance), herbicide tolerance, and quality traits (e.g., improved fatty acid compositions, protein content, starch content, and the like). Suitable expression cassettes for insertion include expression cassettes which confer insect resistance, herbicide tolerance, biofuel use, or male sterility traits contained in any of the transgenic events set forth in US Patent Application Public. Nos. 20090038026, 20130031674, 20150361446, 20170088904, 20150267221, 201662346688, and 20200190533 as well as in U.S. Pat. Nos. 6,342,660, 7,323,556, 6,040,497, 8,759,618, 7,157, 281, 6,852,915, 7,705,216, 10,316,330, 8,618,358, 8,450, 561, 8,212,113, 9,428,765, 7,897,748, 8,273,959, 8,093,453, 8,901,378, 9,994,863, 7,928,296, and 8,466,346, each of which are incorporated herein by reference in their entireties.

In certain embodiments, INHT31 plants provided herein, including plants with one or more transgenic loci, modified transgenic loci, and/or comprising transgenic loci excision sites can further comprise one or more targeted genetic changes introduced by one or more of gene editing molecules or systems. Also provided are methods where the targeted genetic changes are introduced and one or more transgenic loci are removed from plants either in series or in parallel (e.g., as set forth in the non-limiting illustration in FIG. 3, bottom "Alternative" panel, where "GE" can represent targeted genetic changes induced by gene editing molecules and "Event Removal" represents excision of one or more transgenic loci with gene editing molecules). Such targeted genetic changes include those conferring traits such as improved yield, improved food and/or feed characteristics (e.g., improved oil, starch, protein, or amino acid quality or quantity), improved nitrogen use efficiency, improved biofuel use characteristics (e.g., improved ethanol production), male sterility/conditional male sterility systems (e.g., by targeting endogenous MS26, MS45 and MSCA1 genes), herbicide tolerance (e.g., by targeting endogenous ALS, EPSPS, HPPD, or other herbicide target genes), delayed flowering, non-flowering, increased biotic stress resistance (e.g., resistance to insect, nematode, bacterial, or fungal damage), increased abiotic stress resistance (e.g., resistance to drought, cold, heat, metal, or salt), enhanced lodging resistance, enhanced growth rate, enhanced biomass, enhanced tillering, enhanced branching, delayed flowering time, delayed senescence, increased flower number, improved architecture for high density planting, improved photosynthesis, increased root mass, increased cell number, improved seedling vigor, improved seedling size, increased rate of cell division, improved metabolic efficiency, and increased meristem size in comparison to a control plant lacking the targeted genetic change. Types of targeted genetic changes that can be introduced include insertions, deletions, and substitutions of one or more nucleotides in the crop plant genome. Sites in endogenous plant genes for the targeted genetic changes include promoter, coding, and non-coding regions (e.g., 5' UTRs, introns, splice donor and acceptor sites and 3' UTRs). In certain embodiments, the targeted genetic change comprises an insertion of a regulatory or other DNA sequence in an endogenous plant gene. Non-limiting examples of regulatory sequences which can be inserted into endogenous plant genes with gene editing molecules to effect targeted genetic changes which confer useful phenotypes include those set forth in US Patent Application Publication 20190352655, which is incorporated herein by example, such as: (a) auxin response element (AuxRE) sequence; (b) at least one D1-4 sequence (Ulmasov et al. (1997) Plant Cell, 9:1963-1971), (c) at least one DR5 sequence (Ulmasov et al. (1997) Plant Cell, 9:1963-1971); (d) at least one m5-DR5 sequence (Ulmasov et al. (1997) Plant Cell, 9:1963-1971); (e) at least one P3 sequence; (f) a small RNA recognition site sequence bound by a corresponding small RNA (e.g., an siRNA, a microRNA (miRNA), a trans-acting siRNA as described in U.S. Pat. No. 8,030,473, or a phased sRNA as described in U.S. Pat. No. 8,404,928; both of these cited patents are incorporated by reference herein); (g) a microRNA (miRNA) recognition site sequence; (h) the sequence recognizable by a specific binding agent includes a microRNA (miRNA) recognition sequence for an engineered miRNA wherein the specific binding agent is the corresponding engineered mature miRNA; (i) a transposon recognition sequence; (j) a sequence recognized by an ethylene-responsive element binding-factor-associated amphiphilic repression (EAR) motif; (k) a splice site sequence (e.g., a donor site, a branching site, or an acceptor site; see, for example, the splice sites and splicing signals set forth in the internet site lemur[dot]amu[dot]edu[dot]pl/share/ERISdb/home.html); (l) a recombinase recognition site sequence that is recognized by a site-specific recombinase; (m) a sequence encoding an RNA or amino acid aptamer or an RNA riboswitch, the specific binding agent is the corresponding ligand, and the change in expression is upregulation or downregulation; (n) a hormone responsive element recognized by a nuclear receptor or a hormone-binding domain thereof; (o) a transcription factor binding sequence; and (p) a polycomb response element (see Xiao et al. (2017) Nature Genetics, 49:1546-1552, doi: 10.1038/ng.3937). Non limiting examples of target soybean genes that can be subjected to targeted gene edits to confer useful traits include: (a) ZmIPK1 (herbicide tolerant and phytate reduced soybean; Shukla et al., Nature. 2009; 459:437-41); (b) ZmGL2 (reduced epicuticular wax in leaves; Char et al. Plant Biotechnol J. 2015; 13:1002); (c) ZmMTL (induction of haploid plants; Kelliher et al. Nature. 2017; 542:105); (d) Wx1 (high amylopectin content; US 20190032070; incorporated herein by reference in its entirety); (e) TMS5 (thermosensitive male sterile; Li et al. J Genet Genomics. 2017; 44:465-8); (f) ALS (herbicide tolerance; Svitashev et al.; Plant Physiol. 2015; 169:931-45); and (g) ARGOS8 (drought stress tolerance; Shi et al., Plant Biotechnol J. 2017; 15:207-16). Non-limiting examples of target genes in crop plants including soybean which can be subjected to targeted genetic changes which confer useful phenotypes include those set forth in US Patent Application Nos. 20190352655, 20200199609, 20200157554, and 20200231982, which are each incorporated herein in their entireties; and Zhang et al. (Genome Biol. 2018; 19: 210).

Gene editing molecules of use in methods provided herein include molecules capable of introducing a double-strand break ("DSB") or single-strand break ("SSB") in double-stranded DNA, such as in genomic DNA or in a target gene located within the genomic DNA as well as accompanying guide RNA or donor DNA template polynucleotides. Examples of such gene editing molecules include: (a) a nuclease comprising an RNA-guided nuclease, an RNA-guided DNA endonuclease or RNA directed DNA endonuclease (RdDe), a class 1 CRISPR type nuclease system, a type II Cas nuclease, a Cas9, a nCas9 nickase, a type V Cas nuclease, a Cas12a nuclease, a nCas12a nickase, a Cas12d (CasY), a Cas12e (CasX), a Cas12b (C2c1), a Cas12c (C2c3), a Cas12i, a Cas12j, a Cas14, an engineered nuclease, a codon-optimized nuclease, a zinc-finger nuclease (ZFN) or nickase, a transcription activator-like effector nuclease (TAL-effector nuclease or TALEN) or nickase (TALE-nickase), an Argonaute, and a meganuclease or engineered meganuclease; (b) a polynucleotide encoding one or more nucleases capable of effectuating site-specific alteration (including introduction of a DSB or SSB) of a target nucleotide sequence; (c) a guide RNA (gRNA) for an RNA-guided nuclease, or a DNA encoding a gRNA for an RNA-guided nuclease; (d) donor DNA template polynucleotides; and (e) other DNA templates (dsDNA, ssDNA, or combinations thereof) suitable for insertion at a break in genomic DNA (e.g., by non-homologous end joining (NHEJ) or microhomology-mediated end joining (MMEJ).

CRISPR-type genome editing can be adapted for use in the plant cells and methods provided herein in several ways. CRISPR elements, e.g., gene editing molecules comprising CRISPR endonucleases and CRISPR guide RNAs including single guide RNAs or guide RNAs in combination with tracrRNAs or scoutRNA, or polynucleotides encoding the same, are useful in effectuating genome editing without remnants of the CRISPR elements or selective genetic markers occurring in progeny. In certain embodiments, the CRISPR elements are provided directly to the eukaryotic cell (e.g., plant cells), systems, methods, and compositions as isolated molecules, as isolated or semi-purified products of a cell free synthetic process (e.g., in vitro translation), or as isolated or semi-purified products of in a cell-based synthetic process (e.g., such as in a bacterial or other cell lysate). In certain embodiments, genome-inserted CRISPR elements are useful in plant lines adapted for use in the methods provide herein. In certain embodiments, plants or plant cells used in the systems, methods, and compositions provided herein can comprise a transgene that expresses a CRISPR endonuclease (e.g., a Cas9, a Cpf1-type or other CRISPR endonuclease). In certain embodiments, one or more CRISPR endonucleases with unique PAM recognition sites can be used. Guide RNAs (sgRNAs or crRNAs and a tracrRNA) used to form an RNA-guided endonuclease/guide RNA complex can specifically bind via hybridization to gRNA hybridization site sequences (i.e., protospacer sequences) in the gDNA target site that are adjacent to a protospacer adjacent motif (PAM) sequence. The type of RNA-guided endonuclease typically informs the location of suitable PAM sites and design of crRNAs or sgRNAs. G-rich PAM sites, e.g., 5'-NGG are typically targeted for design of crRNAs or sgRNAs used with Cas9 proteins. Examples of PAM sequences include 5'-NGG (*Streptococcus pyogenes*), 5'-NNAGAA (*Streptococcus thermophilus* CRISPR1), 5'-NGGNG (*Streptococcus thermophilus* CRISPR3), 5'-NNGRRT or 5'-NNGRR (*Staphylococcus aureus* Cas9, SaCas9), and 5'-NNNGATT (*Neisseria meningitidis*). T-rich PAM sites (e.g., 5'-TTN or 5'-TTTV, where "V" is A, C, or G) are typically targeted for design of crRNAs or sgRNAs used with Cas12a proteins (e.g., the Cas12a protein of SEQ ID NO: 15). In some instances, Cas12a can also recognize a 5'-CTA PAM motif. Other examples of potential Cas12a PAM sequences include TTN, CTN, TCN, CCN, TTTN, TCTN, TTCN, CTTN, ATTN, TCCN, TTGN, GTTN, CCCN, CCTN, TTAN, TCGN, CTCN, ACTN, GCTN, TCAN, GCCN, and CCGN (wherein N is defined as any nucleotide). Cpf1 (i.e., Cas12a) endonuclease and corresponding guide RNAs and PAM sites are disclosed in US Patent Application Publication 2016/0208243 A1, which is incorporated herein by reference for its disclosure of DNA encoding Cpf1 endonucleases and guide RNAs and PAM sites. Introduction of one or more of a wide variety of CRISPR guide RNAs that interact with CRISPR endonucleases integrated into a plant genome or otherwise provided to a plant is useful for genetic editing for providing desired phenotypes or traits, for trait screening, or for gene editing mediated trait introgression (e.g., for introducing a trait into a new genotype without backcrossing to a recurrent parent or with limited backcrossing to a recurrent parent). Multiple endonucleases can be provided in expression cassettes with the appropriate promoters to allow multiple genome site editing.

CRISPR technology for editing the genes of eukaryotes is disclosed in US Patent Application Publications 2016/0138008A1 and US2015/0344912A1, and in U.S. Pat. Nos. 8,697,359, 8,771,945, 8,945,839, 8,999,641, 8,993,233, 8,895,308, 8,865,406, 8,889,418, 8,871,445, 8,889,356, 8,932,814, 8,795,965, and 8,906,616. Cpf1 endonuclease and corresponding guide RNAs and PAM sites are disclosed in US Patent Application Publication 2016/0208243 A1. Other CRISPR nucleases useful for editing genomes include Cas12b and Cas12c (see Shmakov et al. (2015) Mol. Cell, 60:385-397; Harrington et al. (2020) Molecular Cell doi: 10.1016/j.molcel.2020.06.022) and CasX and CasY (see Burstein et al. (2016) Nature, doi:10.1038/nature21059; Harrington et al. (2020) Molecular Cell doi:10.1016/j.molcel.2020.06.022), or Cas12j (Pausch et al, (2020) Science 10.1126/science.abb1400). Plant RNA promoters for expressing CRISPR guide RNA and plant codon-optimized CRISPR Cas9 endonuclease are disclosed in International Patent Application PCT/US2015/018104 (published as WO 2015/131101 and claiming priority to U.S. Provisional Patent Application 61/945,700). Methods of using CRISPR technology for genome editing in plants are disclosed in US Patent Application Publications US 2015/0082478A1 and US 2015/0059010A1 and in International Patent Application PCT/US2015/038767 A1 (published as WO 2016/007347 and claiming priority to U.S. Provisional Patent Application 62/023,246). All of the patent publications referenced in this paragraph are incorporated herein by reference in their entirety. In certain embodiments, an RNA-guided endonuclease that leaves a blunt end following cleavage of the target site is used. Blunt-end cutting RNA-guided endonucleases include Cas9, Cas12c, and Cas 12h (Yan et al., 2019). In certain embodiments, an RNA-guided endonuclease that leaves a staggered single stranded DNA overhanging end following cleavage of the target site following cleavage of the target site is used. Staggered-end cutting RNA-guided endonucleases include Cas12a, Cas12b, and Cas12e.

The methods can also use sequence-specific endonucleases or sequence-specific endonucleases and guide RNAs that cleave a single DNA strand in a dsDNA target site. Such cleavage of a single DNA strand in a dsDNA target site is also referred to herein and elsewhere as "nicking" and can be effected by various "nickases" or systems that provide for nicking. Nickases that can be used include nCas9 (Cas9 comprising a D10A amino acid substitution), nCas12a (e.g., Cas12a comprising an R1226A amino acid substitution; Yamano et al., 2016), Cas12i (Yan et al. 2019), a zinc finger nickase e.g., as disclosed in Kim et al., 2012), a TALE nickase (e.g., as disclosed in Wu et al., 2014), or a combination thereof. In certain embodiments, systems that provide for nicking can comprise a Cas nuclease (e.g., Cas9 and/or Cas12a) and guide RNA molecules that have at least one base mismatch to DNA sequences in the target editing site (Fu et al., 2019). In certain embodiments, genome modifications can be introduced into the target editing site by creating single stranded breaks (i.e., "nicks") in genomic locations separated by no more than about 10, 20, 30, 40, 50, 60, 80, 100, 150, or 200 base pairs of DNA. In certain illustrative and non-limiting embodiments, two nickases (i.e., a CAS nuclease which introduces a single stranded DNA break including nCas9, nCas12a, Cas12i, zinc finger nickases, TALE nickases, combinations thereof, and the like) or nickase systems can directed to make cuts to nearby sites separated by no more than about 10, 20, 30, 40, 50, 60, 80 or 100 base pairs of DNA. In instances where an RNA guided nickase and an RNA guide are used, the RNA guides are adjacent to PAM sequences that are sufficiently close (i.e., separated by no more than about 10, 20, 30, 40, 50, 60, 80, 100, 150, or 200 base pairs of DNA). For the purposes of gene editing, CRISPR arrays can be designed to contain one or multiple guide RNA sequences corresponding to a desired target DNA sequence; see, for example, Cong et al. (2013) Science, 339:819-823; Ran et al. (2013) *Nature Protocols,* 8:2281-2308. At least 16 or 17 nucleotides of gRNA sequence are required by Cas9 for DNA cleavage to occur; for Cpf1 at least 16 nucleotides of gRNA sequence are needed to achieve detectable DNA cleavage and at least 18 nucleotides of gRNA sequence were reported necessary for efficient DNA cleavage in vitro; see Zetsche et al. (2015) *Cell,* 163:759-771. In practice, guide RNA sequences are generally designed to have a length of 17-24 nucleotides (frequently 19, 20, or 21 nucleotides) and exact complementarity (i.e., perfect base-pairing) to the targeted gene or nucleic acid sequence; guide RNAs having less than 100% complementarity to the target sequence can be used (e.g., a gRNA with a length of 20 nucleotides and 1-4 mismatches to the target sequence) but can increase the potential for off-target effects. The design of effective guide RNAs for use in plant genome editing is disclosed in US Patent Application Publication 2015/0082478 A1, the entire specification of which is incorporated herein by reference. More recently, efficient gene editing has been achieved using a chimeric "single guide RNA" ("sgRNA"), an engineered (synthetic) single RNA molecule that mimics a naturally occurring crRNA-tracrRNA complex and contains both a tracrRNA (for binding the nuclease) and at least one crRNA (to guide the nuclease to the sequence targeted for editing); see, for example, Cong et al. (2013) Science, 339:819-823; Xing et al. (2014) *BMC Plant Biol.,* 14:327-340. Chemically modified sgRNAs have been demonstrated to be effective in genome editing; see, for example, Hendel et al. (2015) *Nature Biotechnol.,* 985-991. The design of effective gRNAs for use in plant genome editing is disclosed in US Patent Application Publication 2015/0082478 A1, the entire specification of which is incorporated herein by reference.

Genomic DNA may also be modified via base editing. Both adenine base editors (ABE) which convert A/T base pairs to G/C base pairs in genomic DNA as well as cytosine base pair editors (CBE) which effect C to T substitutions can be used in certain embodiments of the methods provided herein. In certain embodiments, useful ABE and CBE can comprise genome site specific DNA binding elements (e.g., RNA-dependent DNA binding proteins including catalytically inactive Cas9 and Cas12 proteins or Cas9 and Cas12 nickases) operably linked to adenine or cytidine deaminases and used with guide RNAs which position the protein near the nucleotide targeted for substitution. Suitable ABE and CBE disclosed in the literature (Kim, Nat Plants, 2018 March; 4(3):148-151) can be adapted for use in the methods set forth herein. In certain embodiments, a CBE can comprise a fusion between a catalytically inactive Cas9 (dCas9) RNA dependent DNA binding protein fused to a cytidine deaminase which converts cytosine (C) to uridine (U) and selected guide RNAs, thereby effecting a C to T substitution; see Komor et al. (2016) Nature, 533:420-424. In other embodiments, C to T substitutions are effected with Cas9 nickase [Cas9n(D10A)] fused to an improved cytidine deaminase and optionally a bacteriophage Mu dsDNA (double-stranded DNA) end-binding protein Gam; see Komor et al., Sci Adv. 2017 August; 3(8):eaao4774. In other embodiments, adenine base editors (ABEs) comprising an adenine deaminase fused to catalytically inactive Cas9 (dCas9) or a Cas9 D10A nickase can be used to convert A/T base pairs to G/C base pairs in genomic DNA (Gaudelli et al., (2017) Nature 551(7681):464-471.

In certain embodiments, zinc finger nucleases or zinc finger nickases can also be used in the methods provided herein. Zinc-finger nucleases are site-specific endonucleases comprising two protein domains: a DNA-binding domain, comprising a plurality of individual zinc finger repeats that each recognize between 9 and 18 base pairs, and a DNA-cleavage domain that comprises a nuclease domain (typically FokI). The cleavage domain dimerizes in order to cleave DNA; therefore, a pair of ZFNs are required to target non-palindromic target polynucleotides. In certain embodiments, zinc finger nuclease and zinc finger nickase design methods which have been described (Urnov et al. (2010) Nature Rev. Genet., 11:636-646; Mohanta et al. (2017) Genes vol. 8, 12: 399; Ramirez et al. Nucleic Acids Res. (2012); 40(12): 5560-5568; Liu et al. (2013) Nature Communications, 4: 2565) can be adapted for use in the methods set forth herein. The zinc finger binding domains of the zinc finger nuclease or nickase provide specificity and can be engineered to specifically recognize any desired target DNA sequence. The zinc finger DNA binding domains are derived from the DNA-binding domain of a large class of eukaryotic transcription factors called zinc finger proteins (ZFPs). The DNA-binding domain of ZFPs typically contains a tandem array of at least three zinc "fingers" each recognizing a specific triplet of DNA. A number of strategies can be used to design the binding specificity of the zinc finger binding domain. One approach, termed "modular assembly", relies on the functional autonomy of individual zinc fingers with DNA. In this approach, a given sequence is targeted by identifying zinc fingers for each component triplet in the sequence and linking them into a multifinger peptide. Several alternative strategies for designing zinc finger DNA binding domains have also been developed. These methods are designed to accommodate the ability of zinc fingers to contact neighboring fingers as well as nucleotide bases outside their target triplet. Typically, the engineered zinc finger DNA binding domain has a novel binding specificity, compared to a naturally-occurring zinc finger protein. Engineering methods include, for example, rational design and various types of selection. Rational design includes, for example, the use of databases of triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, e.g., U.S. Pat. Nos. 6,453,242 and 6,534,261, both incorporated herein by reference in their entirety. Exemplary selection methods (e.g., phage display and yeast two-hybrid systems) can be adapted for use in the methods described herein. In addition, enhancement of binding specificity for zinc finger binding domains has been described in U.S. Pat. No. 6,794,136, incorporated herein by reference in its entirety. In addition, individual zinc finger domains may be linked together using any suitable linker sequences. Examples of linker sequences are publicly known, e.g., see U.S. Pat. Nos. 6,479,626; 6,903,185; and 7,153,949, incorporated herein by reference in their entirety. The nucleic acid cleavage domain is non-specific and is typically a restriction endonuclease, such as FokI. This endonuclease must dimerize to cleave DNA. Thus, cleavage by FokI as part of a ZFN requires two adjacent and independent binding events, which must occur in both the correct orientation and with appropriate spacing to permit dimer formation. The requirement for two DNA binding events enables more specific targeting of long and potentially unique recognition sites. FokI variants with enhanced activities have been described and can be adapted for use in the methods described herein; see, e.g., Guo et al. (2010) J. Mol. Biol., 400:96-107.

Transcription activator like effectors (TALEs) are proteins secreted by certain Xanthomonas species to modulate gene expression in host plants and to facilitate the colonization by and survival of the bacterium. TALEs act as transcription factors and modulate expression of resistance genes in the plants. Recent studies of TALEs have revealed the code linking the repetitive region of TALEs with their target DNA-binding sites. TALEs comprise a highly conserved and repetitive region consisting of tandem repeats of mostly 33 or 34 amino acid segments. The repeat monomers differ from each other mainly at amino acid positions 12 and 13. A strong correlation between unique pairs of amino acids at positions 12 and 13 and the corresponding nucleotide in the TALE-binding site has been found. The simple relationship between amino acid sequence and DNA recognition of the TALE binding domain allows for the design of DNA binding domains of any desired specificity. TALEs can be linked to a non-specific DNA cleavage domain to prepare genome editing proteins, referred to as TAL-effector nucleases or TALENs. As in the case of ZFNs, a restriction endonuclease, such as FokI, can be conveniently used. Methods for use of TALENs in plants have been described and can be adapted for use in the methods described herein, see Mahfouz et al. (2011) Proc. Natl. Acad. Sci. USA, 108:2623-2628; Mahfouz (2011) GM Crops, 2:99-103; and Mohanta et al. (2017) Genes vol. 8, 12: 399). TALE nickases have also been described and can be adapted for use in methods described herein (Wu et al.; Biochem Biophys Res Commun. (2014); 446(1):261-6; Luo et al; Scientific Reports 6, Article number: 20657 (2016)).

Embodiments of the donor DNA template molecule having a sequence that is integrated at the site of at least one double-strand break (DSB) in a genome include double-stranded DNA, a single-stranded DNA, a single-stranded DNA/RNA hybrid, and a double-stranded DNA/RNA hybrid. In embodiments, a donor DNA template molecule that is double-stranded (e.g., a dsDNA or dsDNA/RNA hybrid) molecule is provided directly to the plant protoplast or plant cell in the form of a double-stranded DNA or a double-stranded DNA/RNA hybrid, or as two single-stranded DNA (ssDNA) molecules that are capable of hybridizing to form dsDNA, or as a single-stranded DNA molecule and a single-stranded RNA (ssRNA) molecule that are capable of hybridizing to form a double-stranded DNA/RNA hybrid; that is to say, the double-stranded polynucleotide molecule is not provided indirectly, for example, by expression in the cell of a dsDNA encoded by a plasmid or other vector. In various non-limiting embodiments of the method, the donor DNA template molecule that is integrated (or that has a sequence that is integrated) at the site of at least one double-strand break (DSB) in a genome is double-stranded and blunt-ended; in other embodiments the donor DNA template molecule is double-stranded and has an overhang or "sticky end" consisting of unpaired nucleotides (e.g., 1, 2, 3, 4, 5, or 6 unpaired nucleotides) at one terminus or both termini. In an embodiment, the DSB in the genome has no unpaired nucleotides at the cleavage site, and the donor DNA template molecule that is integrated (or that has a sequence that is integrated) at the site of the DSB is a blunt-ended double-stranded DNA or blunt-ended double-stranded DNA/RNA hybrid molecule, or alternatively is a single-stranded DNA or a single-stranded DNA/RNA hybrid molecule. In another embodiment, the DSB in the genome has one or more unpaired nucleotides at one or both sides of the cleavage site, and the donor DNA template molecule that is integrated (or that has a sequence that is integrated) at the site of the DSB is a double-stranded DNA or double-stranded DNA/RNA hybrid molecule with an overhang or "sticky end" consisting of unpaired nucleotides at one or both termini, or alternatively is a single-stranded DNA or a single-stranded DNA/RNA hybrid molecule; in embodiments, the donor DNA template molecule DSB is a double-stranded DNA or double-stranded DNA/RNA hybrid molecule that includes an overhang at one or at both termini, wherein the overhang consists of the same number of unpaired nucleotides as the number of unpaired nucleotides created at the site of a DSB by a nuclease that cuts in an off-set fashion (e.g., where a Cas12 nuclease effects an off-set DSB with 5-nucleotide overhangs in the genomic sequence, the donor DNA template molecule that is to be integrated (or that has a sequence that is to be integrated) at the site of the DSB is double-stranded and has 5 unpaired nucleotides at one or both termini). In certain embodiments, one or both termini of the donor DNA template molecule contain no regions of sequence homology (identity or complementarity) to genomic regions flanking the DSB; that is to say, one or both termini of the donor DNA template molecule contain no regions of sequence that is sufficiently complementary to permit hybridization to genomic regions immediately adjacent to the location of the DSB. In embodiments, the donor DNA template molecule contains no homology to the locus of the DSB, that is to say, the donor DNA template molecule contains no nucleotide sequence that is sufficiently complementary to permit hybridization to genomic regions immediately adjacent to the location of the DSB. In embodiments, the donor DNA template molecule is at least partially double-stranded and includes 2-20 base-pairs, e. g., 2, 3, 4, 5, 6, 7, 8, 9, 10, 11, 12, 13, 14, 15, 16, 17, 18, 19, or 20 base-pairs; in embodiments, the donor DNA template molecule is double-stranded and blunt-ended and consists of 2-20 base-pairs, e.g., 2, 3, 4, 5, 6, 7, 8, 9, 10, 11, 12, 13, 14, 15, 16, 17, 18, 19, or 20 base-pairs; in other embodiments, the donor DNA template molecule is double-stranded and includes 2-20 base-pairs, e.g., 2, 3, 4, 5, 6, 7, 8, 9, 10, 11, 12, 13, 14, 15, 16, 17, 18, 19, or 20 base-pairs and in addition has at least one overhang or "sticky end" consisting of at least one additional, unpaired nucleotide at one or at both termini. In an embodiment, the donor DNA template molecule that is integrated (or that has a sequence that is integrated) at the site of at least one double-strand break (DSB) in a genome is a blunt-ended double-stranded DNA or a blunt-ended double-stranded DNA/RNA hybrid molecule of about 18 to about 300 base-pairs, or about 20 to about 200 base-pairs, or about 30 to about 100 base-pairs, and having at least one phosphorothioate bond between adjacent nucleotides at a 5' end, 3' end, or both 5' and 3' ends. In embodiments, the donor DNA template molecule includes single strands of at least 11, at least 18, at least 20, at least 30, at least 40, at least 60, at least 80, at least 100, at least 120, at least 140, at least 160, at least 180, at least 200, at least 240, at about 280, or at least 320 nucleotides. In embodiments, the donor DNA template molecule has a length of at least 2, at least 3, at least 4, at least 5, at least 6, at least 7, at least 8, at least 9, at least 10, or at least 11 base-pairs if double-stranded (or nucleotides if single-stranded), or between about 2 to about 320 base-pairs if double-stranded (or nucleotides if single-stranded), or between about 2 to about 500 base-pairs if double-stranded (or nucleotides if single-stranded), or between about 5 to about 500 base-pairs if double-stranded (or nucleotides if single-stranded), or between about 5 to about 300 base-pairs if double-stranded (or nucleotides if single-stranded), or between about 11 to about 300 base-pairs if double-stranded (or nucleotides if single-stranded), or about 18 to about 300 base-pairs if double-stranded (or nucleotides if single-stranded), or between about 30 to about 100 base-pairs if double-stranded (or nucleotides if single-stranded). In embodiments, the donor DNA template molecule includes chemically modified nucleotides (see, e.g., the various modifications of internucleotide linkages, bases, and sugars described in Verma and Eckstein (1998) Annu. Rev. Biochem., 67:99-134); in embodiments, the naturally occurring phosphodiester backbone of the donor DNA template molecule is partially or completely modified with phosphorothioate, phosphorodithioate, or methylphosphonate internucleotide linkage modifications, or the donor DNA template molecule includes modified nucleoside bases or modified sugars, or the donor DNA template molecule is labelled with a fluorescent moiety (e.g., fluorescein or rhodamine or a fluorescent nucleoside analogue) or other detectable label (e.g., biotin or an isotope). In another embodiment, the donor DNA template molecule contains secondary structure that provides stability or acts as an aptamer. Other related embodiments include double-stranded DNA/RNA hybrid molecules, single-stranded DNA/RNA hybrid donor molecules, and single-stranded donor DNA template molecules (including single-stranded, chemically modified donor DNA template molecules), which in analogous procedures are integrated (or have a sequence that is integrated) at the site of a double-strand break. Donor DNA templates provided herein include those comprising CgRRS sequences flanked by DNA with homology to a donor polynucleotide and include the donor DNA template set forth in SEQ ID NO: 11 and equivalents thereof with longer or shorter homology arms. In certain embodiments, a donor DNA template can comprise an adapter molecule (e.g., a donor DNA template formed by annealing single stranded DNAs which do not overlap at their 5' and 3' terminal ends) with cohesive ends which can anneal to an overhanging cleavage site (e.g., introduced by a Cas12a nuclease and suitable gRNAs). In certain embodiments, integration of the donor DNA templates can be facilitated by use of a bacteriophage lambda exonuclease, a bacteriophage lambda beta SSAP protein, and an *E. coli* SSB essentially as set forth in US Patent Application Publication 20200407754, which is incorporated herein by reference in its entirety.

Donor DNA template molecules used in the methods provided herein include DNA molecules comprising, from 5' to 3', a first homology arm, a replacement DNA, and a second homology arm, wherein the homology arms containing sequences that are partially or completely homologous to genomic DNA (gDNA) sequences flanking a target site-specific endonuclease cleavage site in the gDNA. In certain embodiments, the replacement DNA can comprise an insertion, deletion, or substitution of 1 or more DNA base pairs relative to the target gDNA. In an embodiment, the donor DNA template molecule is double-stranded and perfectly base-paired through all or most of its length, with the possible exception of any unpaired nucleotides at either terminus or both termini. In another embodiment, the donor DNA template molecule is double-stranded and includes one or more non-terminal mismatches or non-terminal unpaired nucleotides within the otherwise double-stranded duplex. In an embodiment, the donor DNA template molecule that is integrated at the site of at least one double-strand break (DSB) includes between 2-20 nucleotides in one (if single-stranded) or in both strands (if double-stranded), e. g., 2, 3, 4, 5, 6, 7, 8, 9, 10, 11, 12, 13, 14, 15, 16, 17, 18, 19, or 20 nucleotides on one or on both strands, each of which can be base-paired to a nucleotide on the opposite strand (in the case of a perfectly base-paired double-stranded polynucleotide molecule). Such donor DNA templates can be integrated in genomic DNA containing blunt and/or staggered double stranded DNA breaks by homology-directed repair (HDR). In certain embodiments, a donor DNA template homology arm can be about 20, 50, 100, 200, 400, or 600 to about 800, or 1000 base pairs in length. In certain embodiments, a donor DNA template molecule can be delivered to a plant cell) in a circular (e.g., a plasmid or a viral vector including a geminivirus vector) or a linear DNA molecule. In certain embodiments, a circular or linear DNA molecule that is used can comprise a modified donor DNA template molecule comprising, from 5' to 3', a first copy of the target sequence-specific endonuclease cleavage site sequence, the first homology arm, the replacement DNA, the second homology arm, and a second copy of the target sequence-specific endonuclease cleavage site sequence. Without seeking to be limited by theory, such modified donor DNA template molecules can be cleaved by the same sequence-specific endonuclease that is used to cleave the target site gDNA of the eukaryotic cell to release a donor DNA template molecule that can participate in HDR-mediated genome modification of the target editing site in the plant cell genome. In certain embodiments, the donor DNA template can comprise a linear DNA molecule comprising, from 5' to 3', a cleaved target sequence-specific endonuclease cleavage site sequence, the first homology arm, the replacement DNA, the second homology arm, and a cleaved target sequence-specific endonuclease cleavage site sequence. In certain embodiments, the cleaved target sequence-specific endonuclease sequence can comprise a blunt DNA end or a blunt DNA end that can optionally comprise a 5' phosphate group. In certain embodiments, the cleaved target sequence-specific endonuclease sequence comprises a DNA end having a single-stranded 5' or 3' DNA overhang. Such cleaved target sequence-specific endonuclease cleavage site sequences can be produced by either cleaving an intact target sequence-specific endonuclease cleavage site sequence or by synthesizing a copy of the cleaved target sequence-specific endonuclease cleavage site sequence. Donor DNA templates can be synthesized either chemically or enzymatically (e.g., in a polymerase chain reaction (PCR)). Donor DNA templates provided herein include those comprising CgRRS sequences flanked by DNA with homology to a donor polynucleotide. An example of a useful DNA donor template provided herein is a DNA molecule comprising SEQ ID NO: 11.

Various treatments are useful in delivery of gene editing molecules and/or other molecules to a MON89788 or INHT31 plant cell. In certain embodiments, one or more treatments is employed to deliver the gene editing or other molecules (e.g., comprising a polynucleotide, polypeptide or combination thereof) into a eukaryotic or plant cell, e.g., through barriers such as a cell wall, a plasma membrane, a nuclear envelope, and/or other lipid bilayer. In certain embodiments, a polynucleotide-, polypeptide-, or RNP-containing composition comprising the molecules are delivered directly, for example by direct contact of the composition with a plant cell. Aforementioned compositions can be provided in the form of a liquid, a solution, a suspension, an emulsion, a reverse emulsion, a colloid, a dispersion, a gel, liposomes, micelles, an injectable material, an aerosol, a solid, a powder, a particulate, a nanoparticle, or a combination thereof can be applied directly to a plant, plant part, plant cell, or plant explant (e.g., through abrasion or puncture or otherwise disruption of the cell wall or cell membrane, by spraying or dipping or soaking or otherwise directly contacting, by microinjection). For example, a plant cell or plant protoplast is soaked in a liquid genome editing molecule-containing composition, whereby the agent is delivered to the plant cell. In certain embodiments, the agent-containing composition is delivered using negative or positive pressure, for example, using vacuum infiltration or application of hydrodynamic or fluid pressure. In certain embodiments, the agent-containing composition is introduced into a plant cell or plant protoplast, e.g., by microinjection or by disruption or deformation of the cell wall or cell membrane, for example by physical treatments such as by application of negative or positive pressure, shear forces, or treatment with a chemical or physical delivery agent such as surfactants, liposomes, or nanoparticles; see, e.g., delivery of materials to cells employing microfluidic flow through a cell-deforming constriction as described in US Published Patent Application 2014/0287509, incorporated by reference in its entirety herein. Other techniques useful for delivering the agent-containing composition to a eukaryotic cell, plant cell or plant protoplast include: ultrasound or sonication; vibration, friction, shear stress, vortexing, cavitation; centrifugation or application of mechanical force; mechanical cell wall or cell membrane deformation or breakage; enzymatic cell wall or cell membrane breakage or permeabilization; abrasion or mechanical scarification (e.g., abrasion with carborundum or other particulate abrasive or scarification with a file or sandpaper) or chemical scarification (e.g., treatment with an acid or caustic agent); and electroporation. In certain embodiments, the agent-containing composition is provided by bacterially mediated (e.g., *Agrobacterium* sp., *Rhizobium* sp., *Sinorhizobium* sp., *Mesorhizobium* sp., *Bradyrhizobium* sp., *Azobacter* sp., *Phyllobacterium* sp.) transfection of the plant cell or plant protoplast with a polynucleotide encoding the genome editing molecules (e.g., RNA dependent DNA endonuclease, RNA dependent DNA binding protein, RNA dependent nickase, ABE, or CBE, and/or guide RNA); see, e.g., Broothaerts et al. (2005) *Nature*, 433:629-633). Any of these techniques or a combination thereof are alternatively employed on the plant explant, plant part or tissue or intact plant (or seed) from which a plant cell is optionally subsequently obtained or isolated; in certain embodiments, the agent-containing composition is delivered in a separate step after the plant cell has been isolated.

In some embodiments, one or more polynucleotides or vectors driving expression of one or more genome editing molecules or trait-conferring genes (e.g., herbicide tolerance, insect resistance, and/or male sterility) are introduced into a MON89788 or INHT31 plant cell. In certain embodiments, a polynucleotide vector comprises a regulatory element such as a promoter operably linked to one or more polynucleotides encoding genome editing molecules and/or trait-conferring genes. In such embodiments, expression of these polynucleotides can be controlled by selection of the appropriate promoter, particularly promoters functional in a eukaryotic cell (e.g., plant cell); useful promoters include constitutive, conditional, inducible, and temporally or spatially specific promoters (e.g., a tissue specific promoter, a developmentally regulated promoter, or a cell cycle regulated promoter). Developmentally regulated promoters that can be used in plant cells include Phospholipid Transfer Protein (PLTP), fructose-1,6-bisphosphatase protein, NAD(P)-binding Rossmann-Fold protein, adipocyte plasma membrane-associated protein-like protein, Rieske [2Fe-2S] iron-sulfur domain protein, chlororespiratory reduction 6 protein, D-glycerate 3-kinase, chloroplastic-like protein, chlorophyll a-b binding protein 7, chloroplastic-like protein, ultraviolet-B-repressible protein, Soul heme-binding family protein, Photosystem I reaction center subunit psi-N protein, and short-chain dehydrogenase/reductase protein that are disclosed in US Patent Application Publication No. 20170121722, which is incorporated herein by reference in its entirety and specifically with respect to such disclosure. In certain embodiments, the promoter is operably linked to nucleotide sequences encoding multiple guide RNAs, wherein the sequences encoding guide RNAs are separated by a cleavage site such as a nucleotide sequence encoding a microRNA recognition/cleavage site or a self-cleaving ribozyme (see, e.g., Ferré-D'Amaré and Scott (2014) Cold Spring Harbor Perspectives Biol., 2:a003574). In certain embodiments, the promoter is an RNA polymerase III promoter operably linked to a nucleotide sequence encoding one or more guide RNAs. In certain embodiments, the RNA polymerase III promoter is a plant U6 spliceosomal RNA promoter, which can be native to the genome of the plant cell or from a different species, e.g., a U6 promoter from soybean, tomato, or soybean such as those disclosed U.S. Patent Application Publication 2017/0166912, or a homologue thereof; in an example, such a promoter is operably linked to DNA sequence encoding a first RNA molecule including a Cas12a gRNA followed by an operably linked and suitable 3' element such as a U6 poly-T terminator. In another embodiment, the RNA polymerase III promoter is a plant U3, 7SL (signal recognition particle RNA), U2, or U5 promoter, or chimerics thereof, e.g., as described in U.S. Patent Application Publication 20170166912. In certain embodiments, the promoter operably linked to one or more polynucleotides is a constitutive promoter that drives gene expression in eukaryotic cells (e.g., plant cells). In certain embodiments, the promoter drives gene expression in the nucleus or in an organelle such as a chloroplast or mitochondrion. Examples of constitutive promoters for use in plants include a CaMV 35S promoter as disclosed in U.S. Pat. Nos. 5,858,742 and 5,322,938, a rice actin promoter as disclosed in U.S. Pat. No. 5,641,876, a soybean chloroplast aldolase promoter as disclosed in U.S. Pat. No. 7,151,204, and the nopaline synthase (NOS) and octopine synthase (OCS) promoters from *Agrobacterium tumefaciens*. In certain embodiments, the promoter operably linked to one or more polynucleotides encoding elements of a genome-editing system is a promoter from figwort mosaic virus (FMV), a RUBISCO promoter, or a pyruvate phosphate dikinase (PPDK) promoter, which is active in photosynthetic tissues. Other contemplated promoters include cell-specific or tissue-specific or developmentally regulated promoters, for example, a promoter that limits the expression of the nucleic acid targeting system to germline or reproductive cells (e.g., promoters of genes encoding DNA ligases, recombinases, replicases, or other genes specifically expressed in germline or reproductive cells). In certain embodiments, the genome alteration is limited only to those cells from which DNA is inherited in subsequent generations, which is advantageous where it is desirable that expression of the genome-editing system be limited in order to avoid genotoxicity or other unwanted effects. All of the patent publications referenced in this paragraph are incorporated herein by reference in their entirety.

Expression vectors or polynucleotides provided herein may contain a DNA segment near the 3' end of an expression cassette that acts as a signal to terminate transcription, directs polyadenylation of the resultant mRNA, and may also support promoter activity. Such a 3' element is commonly referred to as a "3'-untranslated region" or "3'-UTR" or a "polyadenylation signal." In some cases, plant gene-based 3' elements (or terminators) consist of both the 3'-UTR and downstream non-transcribed sequence (Nuccio et al., 2015). Useful 3' elements include: *Agrobacterium tumefaciens* nos 3', tml 3', tmr 3', tms 3', ocs 3', and tr7 3' elements disclosed in U.S. Pat. No. 6,090,627, incorporated herein by reference, and 3' elements from plant genes such as the heat shock protein 17, ubiquitin, and fructose-1,6-biphosphatase genes from wheat (*Triticum aestivum*), and the glutelin, lactate dehydrogenase, and beta-tubulin genes from rice (*Oryza sativa*), disclosed in US Patent Application Publication 2002/0192813 A1. All of the patent publications referenced in this paragraph are incorporated herein by reference in their entireties.

In certain embodiments, the MON89788 or INHT31 plant cells used herein can comprise haploid, diploid, or polyploid plant cells or plant protoplasts, for example, those obtained from a haploid, diploid, or polyploid plant, plant part or tissue, or callus. In certain embodiments, plant cells in culture (or the regenerated plant, progeny seed, and progeny plant) are haploid or can be induced to become haploid; techniques for making and using haploid plants and plant cells are known in the art, see, e.g., methods for generating haploids in *Arabidopsis thaliana* by crossing of a wild-type strain to a haploid-inducing strain that expresses altered forms of the centromere-specific histone CENH3, as described by Maruthachalam and Chan in "How to make haploid *Arabidopsis thaliana*", protocol available at www[dot]openwetware[dot]org/images/d/d3/Haploid_Arabidopsis_protocol[dot]pdf; (Ravi et al. (2014) *Nature Communications*, 5:5334, doi: 10.1038/ncomms6334). Haploids can also be obtained in a wide variety of monocot plants (e.g., soybean, wheat, rice, sorghum, barley) by crossing a plant comprising a mutated CENH3 gene with a wildtype diploid plant to generate haploid progeny as disclosed in U.S. Pat. No. 9,215,849, which is incorporated herein by reference in its entirety. Haploid-inducing soybean lines that can be used to obtain haploid soybean plants and/or cells include Stock 6, MHI (Moldovian Haploid Inducer), indeterminate gametophyte (ig) mutation, KEMS, RWK, ZEM, ZMS, KMS, and well as transgenic haploid inducer lines disclosed in U.S. Pat. No. 9,677,082, which is incorporated herein by reference in its entirety. Examples of haploid cells include but are not limited to plant cells obtained from haploid plants and plant cells obtained from reproductive tissues, e.g., from flowers, developing flowers or flower buds, ovaries, ovules, megaspores, anthers, pollen, megagametophyte, and microspores. In certain embodiments where the plant cell or plant protoplast is haploid, the genetic complement can be doubled by chromosome doubling (e.g., by spontaneous chromosomal doubling by meiotic non-reduction, or by using a chromosome doubling agent such as colchicine, oryzalin, trifluralin, pronamide, nitrous oxide gas, anti-microtubule herbicides, anti-microtubule agents, and mitotic inhibitors) in the plant cell or plant protoplast to produce a doubled haploid plant cell or plant protoplast wherein the complement of genes or alleles is homozygous; yet other embodiments include regeneration of a doubled haploid plant from the doubled haploid plant cell or plant protoplast. Another embodiment is related to a hybrid plant having at least one parent plant that is a doubled haploid plant provided by this approach. Production of doubled haploid plants provides homozygosity in one generation, instead of requiring several generations of self-crossing to obtain homozygous plants. The use of doubled haploids is advantageous in any situation where there is a desire to establish genetic purity (i.e., homozygosity) in the least possible time. Doubled haploid production can be particularly advantageous in slow-growing plants or for producing hybrid plants that are offspring of at least one doubled-haploid plant.

In certain embodiments, the MON89788 or INHT31 plant cells used in the methods provided herein can include non-dividing cells. Such non-dividing cells can include plant cell protoplasts, plant cells subjected to one or more of a genetic and/or pharmaceutically-induced cell-cycle blockage, and the like.

In certain embodiments, the MON89788 or INHT31 plant cells in used in the methods provided herein can include dividing cells. Dividing cells can include those cells found in various plant tissues including leaves, meristems, and embryos. These tissues include dividing cells from young soybean leaf, meristems and scutellar tissue from about 8 or 10 to about 12 or 14 days after pollination (DAP) embryos. The isolation of soybean embryos has been described in several publications (Brettschneider, Becker, and Lörz 1997; Leduc et al. 1996; Frame et al. 2011; K. Wang and Frame 2009). In certain embodiments, basal leaf tissues (e.g., leaf tissues located about 0 to 3 cm from the ligule of a soybean plant; Kirienko, Luo, and Sylvester 2012) are targeted for HDR-mediated gene editing. Methods for obtaining regenerable plant structures and regenerating plants from the NHEJ-, MMEJ-, or HDR-mediated gene editing of plant cells provided herein can be adapted from methods disclosed in US Patent Application Publication No. 20170121722, which is incorporated herein by reference in its entirety and specifically with respect to such disclosure. In certain embodiments, single plant cells subjected to the HDR-mediated gene editing will give rise to single regenerable plant structures. In certain embodiments, the single regenerable plant cell structure can form from a single cell on, or within, an explant that has been subjected to the NHEJ-, MMEJ-, or HDR-mediated gene editing.

In some embodiments, methods provided herein can include the additional step of growing or regenerating an INHT31 plant from a INHT31 plant cell that had been subjected to the gene editing or from a regenerable plant structure obtained from that INHT31 plant cell. In certain embodiments, the plant can further comprise an inserted transgene, a target gene edit, or genome edit as provided by the methods and compositions disclosed herein. In certain embodiments, callus is produced from the plant cell, and plantlets and plants produced from such callus. In other embodiments, whole seedlings or plants are grown directly from the plant cell without a callus stage. Thus, additional related aspects are directed to whole seedlings and plants grown or regenerated from the plant cell or plant protoplast having a target gene edit or genome edit, as well as the seeds of such plants. In certain embodiments wherein the plant cell or plant protoplast is subjected to genetic modification (for example, genome editing by means of, e.g., an RdDe), the grown or regenerated plant exhibits a phenotype associated with the genetic modification. In certain embodiments, the grown or regenerated plant includes in its genome two or more genetic or epigenetic modifications that in combination provide at least one phenotype of interest. In certain embodiments, a heterogeneous population of plant cells having a target gene edit or genome edit, at least some of which include at least one genetic or epigenetic modification, is provided by the method; related aspects include a plant having a phenotype of interest associated with the genetic or epigenetic modification, provided by either regeneration of a plant having the phenotype of interest from a plant cell or plant protoplast selected from the heterogeneous population of plant cells having a target gene or genome edit, or by selection of a plant having the phenotype of interest from a heterogeneous population of plants grown or regenerated from the population of plant cells having a targeted genetic edit or genome edit. Examples of phenotypes of interest include herbicide resistance, improved tolerance of abiotic stress (e.g., tolerance of temperature extremes, drought, or salt) or biotic stress (e.g., resistance to nematode, bacterial, or fungal pathogens), improved utilization of nutrients or water, modified lipid, carbohydrate, or protein composition, improved flavor or appearance, improved storage characteristics (e.g., resistance to bruising, browning, or softening), increased yield, altered morphology (e.g., floral architecture or color, plant height, branching, root structure). In an embodiment, a heterogeneous population of plant cells having a target gene edit or genome edit (or seedlings or plants grown or regenerated therefrom) is exposed to conditions permitting expression of the phenotype of interest; e.g., selection for herbicide resistance can include exposing the population of plant cells having a target gene edit or genome edit (or seedlings or plants grown or regenerated therefrom) to an amount of herbicide or other substance that inhibits growth or is toxic, allowing identification and selection of those resistant plant cells (or seedlings or plants) that survive treatment. Methods for obtaining regenerable plant structures and regenerating plants from plant cells or regenerable plant structures can be adapted from published procedures (Roest and Gilissen, Acta Bot. Neerl., 1989, 38(1), 1-23; Bhaskaran and Smith, Crop Sci. 30(6):1328-1337; Ikeuchi et al., Development, 2016, 143: 1442-1451). Methods for obtaining regenerable plant structures and regenerating plants from plant cells or regenerable plant structures can also be adapted from US Patent Application Publication No. 20170121722, which is incorporated herein by reference in its entirety and specifically with respect to such disclosure. Also provided are heterogeneous or homogeneous populations of such plants or parts thereof (e.g., seeds), succeeding generations or seeds of such plants grown or regenerated from the plant cells or plant protoplasts, having a target gene edit or genome edit. Additional related aspects include a hybrid plant provided by crossing a first plant grown or regenerated from a plant cell or plant protoplast having a target gene edit or genome edit and having at least one genetic or epigenetic modification, with a second plant, wherein the hybrid plant contains the genetic or epigenetic modification; also contemplated is seed produced by the hybrid plant. Also envisioned as related aspects are progeny seed and progeny plants, including hybrid seed and hybrid plants, having the regenerated plant as a parent or ancestor. The plant cells and derivative plants and seeds disclosed herein can be used for various purposes useful to the consumer or grower. In other embodiments, processed products are made from the INHT31 plant or its seeds, including: (a) soybean seed meal (defatted or non-defatted); (b) extracted proteins, oils, sugars, and starches; (c) fermentation products; (d) animal feed or human food products (e.g., feed and food comprising soybean seed meal (defatted or non-defatted) and other ingredients (e.g., other cereal grains, other seed meal, other protein meal, other oil, other starch, other sugar, a binder, a preservative, a humectant, a vitamin, and/or mineral; (e) a pharmaceutical; (f) raw or processed biomass (e.g., cellulosic and/or lignocellulosic material); and (g) various industrial products.

EMBODIMENTS

Various embodiments of the plants, genomes, methods, biological samples, and other compositions described herein are set forth in the following sets of numbered embodiments.

1a. A transgenic soybean plant cell comprising an INHT31 transgenic locus comprising an originator guide RNA recognition site (OgRRS) in a first DNA junction polynucleotide of a MON89788 transgenic locus and a cognate guide RNA recognition site (CgRRS) in a second DNA junction polynucleotide of the MON89788 transgenic locus.

1b. A transgenic soybean plant cell comprising an INHT31 transgenic locus comprising an insertion and/or substitution of DNA in a DNA junction polynucleotide of a MON89788 transgenic locus with DNA comprising a cognate guide RNA recognition site (CgRRS).

2. The transgenic soybean plant cell of embodiment 1a or 1b, wherein said CgRRS comprises the DNA molecule set forth in SEQ ID NO: 16 or 17; and/or wherein said MON89788 transgenic locus is set forth in SEQ ID NO:1, is present in seed deposited at the ATCC under accession No. PTA-6708, is present in progeny thereof, is present in allelic variants thereof, or is present in other variants thereof.

3. The transgenic soybean plant cell of embodiments 1a, 1b, or 2, wherein said INHT31 transgenic locus comprises the DNA molecule set forth in SEQ ID NO: 14.

4. A transgenic soybean plant part comprising the soybean plant cell of any one of embodiments 1a, 1b, 2, or 3, wherein said soybean plant part is optionally a seed.

5. A transgenic soybean plant comprising the soybean plant cell of any one of embodiments 1a, 1b, 2, or 3.

6. A method for obtaining a bulked population of inbred seed comprising selfing the transgenic soybean plant of embodiment 5 and harvesting seed comprising the INHT31 transgenic locus from the selfed soybean plant.

7. A method of obtaining hybrid soybean seed comprising crossing the transgenic soybean plant of embodiment 5 to a second soybean plant which is genetically distinct from the first soybean plant and harvesting seed comprising the INHT31 transgenic locus from the cross.

8. A DNA molecule comprising SEQ ID NO: 14, 16, or 17.

9. A processed transgenic soybean plant product comprising the DNA molecule of embodiment 8.

10. A biological sample containing the DNA molecule of embodiment 8.

11. A nucleic acid molecule adapted for detection of genomic DNA comprising the DNA molecule of embodiment 8, wherein said nucleic acid molecule optionally comprises a detectable label.

12. A method of detecting a soybean plant cell comprising the INHT31 transgenic locus of any one of embodiments 1a, 1b, 2, or 3, comprising the step of detecting DNA molecule comprising SEQ ID NO: 14, 16, or 17.

13. A method of excising the INHT31 transgenic locus from the genome of the soybean plant cell of any one of embodiments 1a, 1b, 2, or 3, comprising the steps of:
  (a) contacting the edited transgenic plant genome of the plant cell of embodiment 5 with: (i) an RNA dependent DNA endonuclease (RdDe); and (ii) a guide RNA (gRNA) capable of hybridizing to the guide RNA hybridization site of the OgRRS and the CgRRS; wherein the RdDe recognizes a OgRRS/gRNA and a CgRRS/gRNA hybridization complex; and,
  (b) selecting a transgenic plant cell, transgenic plant part, or transgenic plant wherein the INHT31 transgenic locus flanked by the OgRRS and the CgRRS has been excised.

EXAMPLES

Example 1. Application of a Cas12a RNA Guided Endonuclease and Guide RNAs to Change or Excise the 5'-T-DNA Junction Sequence in the MON89788 Event The MON89788 5' junction polynucleotide sequence set forth in SEQ ID NO:1, SEQ ID NO: 2, and FIG. 1 contains five Cas12a recognition sequences (5'_Guide-1, -2, -3, -4, and -5 in Table 1) located upstream (5') of the genomic DNA/transgenic DNA junction in the genomic DNA of the 5' junction polynucleotide. The gRNAs encoded by SEQ ID NO: 20, 21, 22, 23, and/or 24 can be used to modify some of the genome/insert junction sequence without disrupting the sequence that is recognized and amplified by a MON89788 event-specific assay (e.g. Example 1 of U.S. Pat. No. 9,944,945, incorporated herein by reference in its entirety). There are several iterations of this approach. Any of the aforementioned gRNAs can be used to create an indel in the MON89788 genome/insert junction sequence. Alternatively, a non-overlapping combination of two guides, like 5'_Guide-1 and 5'_Guide-5 could be used to disrupt the genomic DNA of the MON89788 5' junction polynucleotide.

TABLE 1

Description of 5' Junction Polynucleotide Guide RNAs and SEQ ID NO of DNA encoding RNA comprising the Guide RNA

| Guide RNA ID | SEQ ID NO | Start-End in SEQ ID NO: 1 | Strand of SEQ ID NO: 1 | PAM |
|---|---|---|---|---|
| 5'_Guide-1 | 20 | 1002-1028 | −1 | TTTC |
| 5'_Guide-2 | 21 | 991-1017 | −1 | TTTG |
| 5'_Guide-3 | 22 | 990-1016 | 1 | TTTG |
| 5'_Guide-4 | 23 | 982-1008 | 1 | TTTC |
| 5'_Guide-5 | 24 | 966-992 | 1 | TTTG |

The Cas12a nuclease and the single or combined guide RNAs are introduced into soybean plant cells containing the MON89788 event. In certain embodiments, the Cas12a nuclease and gRNA(s) are encoded and expressed from a T-DNA transformed into the MON89788 event via *Agrobacterium*-mediated transformation. Alternatively, the T-DNA can be transformed into any convenient soy line, and then crossed with the MON89788 event to combine the Cas12a ribonucleoprotein expressing T-DNA with the MON89788 event. The Cas12a nuclease and gRNAs can also be assembled in vitro then delivered to MON89788 explants as ribonucleoprotein complexes using a biolistic approach (Svitashev et al., Nat Commun. 2016; 7:13274; Zhang et al., 2021, Plant Commun. 2(2):100168). Also, a plasmid encoding a Cas12a nuclease and the gRNA(s) can be delivered to MON89788 explants using a biolistic approach. This will produce plant cells that have a high likelihood of incurring mutations that disrupt the MON89788 5' junction polynucleotide sequence.

In the *Agrobacterium* approach, a binary vector that contains a strong constitutive expression cassette like the AtUbi10 promoter::AtUbi10 terminator driving Cas12a, a PolII or PolII gene cassette driving the Cas12a gRNA(s) and a CaMV 35S:PAT:NOS or other suitable plant selectable marker is constructed. An expression cassette driving a fluorescent protein like mScarlet may also be useful to the plant transformation process.

The T-DNA-based expression cassettes are delivered from superbinary vectors in *Agrobacterium* strain LBA4404. Soy transformations are performed based on published methods (Zhang et al., 1999, Plant Cell, Tissue and Organ Culture 56(1), 37-46). Briefly, cotyledonary explants are prepared from the 5-day-old soybean seedlings by making a horizontal slice through the hypocotyl region, approximately 3-5 mm below the cotyledon. A subsequent vertical slice is made between the cotyledons, and the embryonic axis is removed. This generates 2 cotyledonary node explants. Approximately 7-12 vertical slices are made on the adaxial surface of the explant about the area encompassing 3 mm above the cotyledon/hypocotyl junction and 1 mm below the cotyledon/hypocotyl junction. Explant manipulations are done with a No. 15 scalpel blade.

Explants are immersed in the *Agrobacterium* inoculum for 30 min and then co-cultured on 100×15 mm Petri plates containing the *Agrobacterium* resuspension medium solidified with 0.5% purified agar (BBL Cat #11853). The co-cultivation plates are overlaid with a piece of Whatman #1 filter paper (Mullins et al., 1990; Janssen and Gardner, 1993; Zhang et al., 1997). The explants (5 per plate) are cultured adaxial side down on the co-cultivation plates, that are overlaid with filter paper, for 3 days at 24° C., under an 18/6 hour light regime with an approximate light intensity of 80 µmol s$^{-1}$ m$^{-2}$ (F17T8/750 cool white bulbs, Litetronics®). The co-cultivation plates were wrapped with Parafilm®.

Following the co-cultivation period explants are briefly washed in B5 medium supplemented with 1.67 mg 1-1 BAP, 3% sucrose, 500 mg l$^{-1}$ ticarcillin and 100 mg l$^{-1}$ cefotaxime. The medium is buffered with 3 mM MES, pH 5.6. Growth regulator, vitamins and antibiotics are filter sterilized post autoclaving. Following the washing step, explants are cultured (5 per plate) in 100×20 mm Petri plates, adaxial side up with the hypocotyl imbedded in the medium, containing the washing medium solidified with 0.8% purified agar (BBL Cat #11853) amended with either 3.3 or 5.0 mg l$^{-1}$ glufosinate (AgrEvo USA). This medium is referred to as shoot initiation medium (SI). Plates are wrapped with 3M pressure sensitive tape (Scotch™, 3M, USA) and cultured under the environmental conditions used during the seed germination step.

After 2 weeks of culture, the hypocotyl region is excised from each of the explants, and the remaining explant, cotyledon with differentiating node, is subsequently subcultured onto fresh SI medium. Following an additional 2 weeks of culture on SI medium, the cotyledons are removed from the differentiating node. The differentiating node is subcultured to shoot elongation medium (SE) composed of Murashige and Skoog (MS) (1962) basal salts, B5 vitamins, 1 mg l$^{-1}$ zeatin-riboside, 0.5 mg l$^{-1}$ GA3 and 0.1 mg l$^{-1}$ IAA, 50 mg l$^{-1}$ glutamine, 50 mg l$^{-1}$ asparagine, 3% sucrose and 3 mM IVIES, pH 5.6. The SE medium is amended with either 1.7 or 2.0 mg l$^{-1}$ glufosinate. The explants are subcultured biweekly to fresh SI medium until shoots reach a length greater than 3 cm. The elongated shoots are rooted on Murashige and Skoog salts with B5 vitamins, 1% sucrose, 0.5 mg l$^{-1}$ NAA without further selection in Magenta Boxes®.

When a sufficient amount of viable tissue is obtained, it can be screened for mutations at the MON89788 junction sequence, using a PCR-based approach. One way to screen is to design DNA oligonucleotide primers that flank and amplify the MON89788 junction plus surrounding sequence. For example, the primers (5'-CTTTTGCCTGTTCGTCTTCTAGCCT-3'; SEQ ID NO: 9) and (5'-TCAGATTGTCGTTTCCCGCCTTCAG-3'; SEQ ID NO: 10) will produce a ~363 bp product in a PCR reaction that can be analyzed for edits at the target site. The size of this product will vary based on the nature of the edit. Amplicons can be sequenced directly using an amplicon sequencing approach or ligated to a convenient plasmid vector for Sanger sequencing. Those plants in which the MON89788 3'-junction sequence is disrupted are selected and grown to maturity. The DNA encoding the Cas12a reagents can be segregated away from the modified junction sequence in a subsequent generation.

Example 2. Application of a Cas12a RNA Guided Endonuclease and Guide RNAs to Change or Excise the 3' DNA Junction Polynucleotide Sequence in the MON89788 Event The MON89788 3' DNA junction polynucleotide sequence set forth in SEQ ID NO: 1, SEQ ID NO: 3, and FIG. 1 straddles the 3' end of the MON89788 transgenic insert and soy genomic DNA. There are five Cas12a recognition sequences, 3'_Guides-1, -2, -3, -4, and -5, are close to or just upstream of the transgene/genomic DNA 3' junction sequence set forth below in Table 2. These gRNAs can be used to modify some of the 3' genome/insert junction sequence in conjunction with a Cas12 nuclease (e.g., the protein of SEQ IF NO: 15) without disrupting the sequence that is recognized and amplified by the MON87988 event-specific assay, which recognizes the 5'-T-DNA junction of this transgenic insertion. There are several iterations of this approach. Either 3'_Guide-1 or 3'_Guide 2 can be used to create an indel in the MON89788 3'-T-DNA junction polynucleotide sequence. Alternatively, can be used together with guide 3'_Guide-3, 3'_Guide-4 or 3'_Guide-5 to eliminate most of genomic DNA in the MON89788 3' DNA junction polynucleotide sequence.

TABLE 2

Description of Guide RNAs and SEQ ID NO of DNA encoding RNA comprising the Guide RNA

| Guide RNA ID | SEQ ID NO | Start-End in SEQ ID NO: 1 | Strand of SEQ ID NO: 1 | PAM |
|---|---|---|---|---|
| 3'_Guide-1 | 4 | 5397-5419 | 1 | TTTA |
| 3'_Guide-2 | 5 | 5391-5413 | 1 | TTTC |

TABLE 2-continued

Description of Guide RNAs and SEQ ID NO of DNA encoding RNA comprising the Guide RNA

| Guide RNA ID | SEQ ID NO | Start-End in SEQ ID NO: 1 | Strand of SEQ ID NO: 1 | PAM |
|---|---|---|---|---|
| 3'_Guide-3 | 6 | 5376-5398 | 1 | TTTA |
| 3'_Guide-4 | 7 | 5368-5390 | 1 | TTTG |
| 3'_Guide-5 | 8 | 5354-5376 | −1 | TTTG |

The Cas12a nuclease and the single or combined guide RNAs are introduced into soybean plant cells containing the MON89788 event. In certain embodiments, the Cas12a nuclease and gRNA(s) are encoded and expressed from a T-DNA transformed into the MON89788 event via *Agrobacterium*-mediated transformation. Alternatively, the T-DNA can be transformed into any convenient soy line, and then crossed with the MON89788 event to combine the Cas12a ribonucleoprotein expressing T-DNA with the MON89788 event. The Cas12a nuclease and gRNAs can also be assembled in vitro then delivered to MON89788 explants as ribonucleoprotein complexes using a biolistic approach (Svitashev et al., Nat Commun. 2016; 7:13274; Zhang et al., 2021, Plant Commun. 2(2):100168). Also, a plasmid encoding a Cas12a nuclease and the gRNA(s) can be delivered to MON89788 explants using a biolistic approach. This will produce plant cells that have a high likelihood of incurring mutations that disrupt the MON89788 3' junction polynucleotide sequence.

In the *Agrobacterium* approach, a binary vector that contains a strong constitutive expression cassette like the AtUbi10 promoter::AtUbi10 terminator driving Cas12a, a PolII or PolIII gene cassette driving the Cas12a gRNA(s) and a CaMV 35S:PAT:NOS or other suitable plant selectable marker is constructed. An expression cassette driving a fluorescent protein like mScarlet may also be useful to the plant transformation process.

Constructs are delivered from superbinary vectors in *Agrobacterium* strain LBA4404. Soy transformations are performed based on published methods (Zhang et al., 1999, Plant Cell, Tissue and Organ Culture 56(1), 37-46) as described in Example 1.

When a sufficient amount of viable tissue is obtained, it can be screened for mutations at the MON89788 junction sequence, using a PCR-based approach. One way to screen is to design DNA oligonucleotide primers that flank and amplify the MON89788 junction plus surrounding sequence. For example, the primers (5'-CTTGCCAATT-GATTGACAACATGCA-3'; SEQ ID NO: 12) and (5'-AA-GATAAAGAACTAAGGGGAAGT-3'; SEQ ID NO: 13) will produce a ~387 bp product that can be analyzed for edits at the target site. The size of this product will vary based on the nature of the edit. Amplicons can be sequenced directly using an amplicon sequencing approach or ligated to a convenient plasmid vector for Sanger sequencing. Those plants in which the MON89788 3' DNA junction polynucleotide sequence is disrupted are selected and grown to maturity. The DNA encoding the Cas12a reagents can be segregated away from the modified junction sequence in a subsequent generation.

Example 3. Insertion of a CgRRS Element in the 3'-Junction of the MON89788 Event Two plant gene expression vectors are prepared. Plant expression cassettes for expressing a bacteriophage lambda exonuclease, a bacteriophage lambda beta SSAP protein, and an *E. coli* SSB are constructed essentially as set forth in US Patent Application Publication 20200407754, which is incorporated herein by reference in its entirety. A DNA sequence encoding a tobacco c2 nuclear localization signal (NLS) is fused in-frame to the DNA sequences encoding the exonuclease, the bacteriophage lambda beta SSAP protein, and the *E. coli* SSB to provide a DNA sequence encoding the c2 NLS-Exo, c2 NLS lambda beta SSAP, and c2 NLS-SSB fusion proteins that are set forth in SEQ ID NO: 135, SEQ ID NO: 134, and SEQ ID NO: 133 of US Patent Application Publication 20200407754, respectively, and incorporated herein by reference in their entireties. DNA sequences encoding the c2 NLS-Exo, c2 NLS lambda beta SSAP, and c2NLS-SSB fusion proteins are operably linked to suitable promoter(s) (e.g., AtUbi10, CaMV19S, CaMV35S, and/or SlUbi10 promoter) and suitable polyadenylation site(s) (e.g., nos 3', PeaE9 3', tmr 3', tms 3', AtUbi10 3', and tr7 3' elements), to provide the exonuclease, SSAP, and SSB plant expression cassettes.

A DNA donor template sequence (SEQ ID NO: 11) that targets the 3' DNA junction polynucleotide sequence of the MON89788 event (SEQ ID NO:1; FIG. 1) for HDR-mediated insertion of a 27 base pair OgRRS sequence (SEQ ID NO: 18) that is identical to a Cas12a recognition site at the 5'-junction polynucleotide of the MON89788 T-DNA insert is constructed. The DNA donor sequence includes a replacement template with desired insertion region (27 base pairs long) flanked on both sides by homology arms ~525 bp in length. The homology arms match (i.e., are homologous to) gDNA (genomic DNA) regions flanking the target genomic DNA insertion site (SEQ ID NO: 3) in the MON89788 transgenic locus (SEQ ID NO: 1). The replacement template region comprising the donor DNA is flanked at each end by DNA sequences identical to the MON89788 3' junction polynucleotide sequence recognized by the same Cas12a RNA-guided nuclease and gRNA (e.g., comprising an RNA encoded by SEQ ID NO: 19) that recognize the OgRRS located in the 5' junction polynucleotide.

A plant expression cassette that provides for expression of the RNA-guided sequence-specific Cas12a endonuclease is constructed. A plant expression cassette that provides for expression of a guide RNA (e.g., comprising an RNA encoded by SEQ ID NO: 5) complementary to sequences adjacent to the insertion site is constructed. An *Agrobacterium* superbinary plasmid transformation vector containing a cassette that provides for the expression of the phosphinothricin N-acetyltransferasesynthase (PAT) protein is constructed. Once the cassettes, donor sequence and *Agrobacterium* superbinary plasmid transformation vector are constructed, they are combined to generate two soybean transformation plasmids. In other embodiments, other gRNAs (e.g., 3'_Guide 1 alone; or 3'_Guide-1 or 3'_Guide-2 with 3'_Guide-5) can be used to introduce double stranded breaks in the MON89788 3' junction polynucleotide for insertion of a CgRRS using similar donor DNA templates and the aforementioned Cas12a, SSAP, SSB, and EXO reagents.

A soybean transformation plasmid is constructed with the PAT cassette, the RNA-guided sequence-specific endonuclease cassette, the guide RNA cassette, and the MON89788 3'-T_DNA junction sequence DNA donor sequence into the *Agrobacterium* superbinary plasmid transformation vector (the control vector).

A soybean transformation plasmid is constructed with the PAT cassette, the RNA-guided sequence-specific endonuclease cassette, the guide RNA cassette, the SSB cassette, the lambda beta SSAP cassette, the Exo cassette, and the MON89788 3'-T_DNA junction sequence donor DNA template sequence (SEQ ID NO: 11) into the *Agrobacterium* superbinary plasmid transformation vector (the lambda red vector).

All constructs are transformed into *Agrobacterium* strain LBA4404.

Soybean transformations are performed based on published methods (Ishida et. al, Nature Protocols 2007; 2, 1614-1621) essentially as described in Example 1.

When a sufficient amount of viable tissue is obtained, it can be screened for insertion at the MON89788 junction sequence, using a PCR-based approach. The PCR primer on the 5'-end is 5'-ATTGCGCACACACCAGAATCCTACT-3' (SEQ ID NO: 25). The PCR primer on the 3'-end is 5'-TATCACCATAGCAAGGAAAGCCCGA-3' (SEQ ID NO: 26). The above primers that flank donor DNA homology arms are used to amplify the MON89788 3'-junction polynucleotide sequence. The correct donor sequence insertion will produce a 1471 bp product. Unique DNA fragments comprising the CgRRS in the MON89788 3' junction polynucleotide is set forth in SEQ ID NO: 16 and 17. Amplicons can be sequenced directly using an amplicon sequencing approach or ligated to a convenient plasmid vector for Sanger sequencing. Those plants in which the MON89788 junction sequence now contains the intended Cas12a recognition sequence are selected and grown to maturity. The T-DNA encoding the Cas12a reagents can be segregated away from the modified junction sequence in a subsequent generation. The resultant INHT31 transgenic locus (SEQ ID NO: 14) comprising the CgRRS and OgRRS (e.g., which each comprise SEQ ID NO: 18) can be excised using Cas12a and a suitable gRNA which hybridizes to DNA comprising SEQ ID NO: 19 at both the OgRRS and the CgRRS.

The breadth and scope of the present disclosure should not be limited by any of the above-described embodiments.

What is claimed is:

1. A method for obtaining a bulked population of inbred seed comprising selfing a transgenic soybean plant comprising a transgenic locus comprising the sequence of SEQ ID NO: 14 and harvesting seed comprising the transgenic locus from the selfed soybean plant.

2. A method of obtaining hybrid soybean seed comprising crossing a transgenic soybean plant comprising a transgenic locus comprising the sequence of SEQ ID NO: 14 to a second soybean plant which is genetically distinct from the first soybean plant and harvesting seed comprising the transgenic locus from the cross.

3. A DNA molecule comprising SEQ ID NO: 14, SEQ ID NO: 16, or SEQ ID NO: 17.

4. A processed transgenic soybean plant product comprising the DNA molecule of claim 3.

5. A biological sample containing the DNA molecule of claim 3.

6. A method of detecting a soybean plant cell comprising the DNA molecule of claim 3, comprising the step of detecting DNA molecule comprising SEQ ID NO: 14, SEQ ID NO 16, or SEQ ID NO 17 in a biological sample containing the soybean plant cell.

7. A method of excising a transgenic locus from the genome of the soybean plant cell comprising:
   (a) contacting the genome of a plant cell comprising a transgenic locus comprising the sequence of SEQ ID NO: 14 with: (i) an RNA dependent DNA endonuclease (RdDe); and (ii) a guide RNA (gRNA) capable of hybridizing to the guide RNA hybridization site of SEQ ID NO: 19, wherein the RdDe recognizes the gRNA/gRNA hybridization site complex; and,
   (b) selecting a transgenic plant cell, transgenic plant part, or transgenic plant wherein the transgenic locus has been excised.

* * * * *

SEQUENCE LISTING

<160> NUMBER OF SEQ ID NOS: 26

<210> SEQ ID NO 1
<211> LENGTH: 6466
<212> TYPE: DNA
<213> ORGANISM: Artificial
<220> FEATURE:
<223> OTHER INFORMATION: synthetic

<400> SEQUENCE: 1

```
tgggggctgc ctgtacttcc caaaacttcg cttccctgac ccatcatatc caggactgga      60
cgattggctt gattgatacc agatgggtga gtcgagtcca cctcggtagc ggcatttatg     120
gcaacgattg cagccacgtt gacctccatc attttttctc atgctcatca tggcctccat     180
catggtggtc atttggtctt tcatggcctc catgtcggcc ttcatctgct cttgaacttc     240
atctatctca ctcatgattc tagccttggc acgtgtttgg taagggtacc gtaaagcgcg     300
ttcgttcttt tttattacta tgattacatt ttgacgatga tgatgattgt aggaaagaat     360
gaaatgagta atgaaacaac taaataaacg tgaatgcatg acaatgataa gttgctgaag     420
tattataaat ttacatagga cattcagtgg aacgtagggt cgaatcaaat cctatttcat     480
taaaaacaat attgttcatc ttgacagagc caaagcataa ctagaaatac aacatggaca     540
catcagcgat tcctaattat gtgggtcatt agttcgacca tgtgttggca gtaacttgaa     600
agactatgaa cttcatcggg agcagagtat gtgtcagtca ccgccttggc tctggctaac     660
aaccttggga tctcttggct ctcatttaga gtaagagcaa atttgtccat ccatttcatg     720
gcttctttat gcaataactc tatcacccct tctcttgctt cccttcaac ctgcaaggtc      780 gacactttg cctgttcgtc ttctagcctt cgcccatgac tagcagctag gttcaccttc      840
tcttcatatt ggtcaatgat tatcaacata ttttcttttg ttttgctcaa ctgttctctc     900
aaacttctct tcgatctctg acaactcttt aacttatcct ctaacatcag gttttccata     960
cttgatttgt ccctcttggc ttttctaagt ttgagctcgt tactgctgcc ccacaaagcc    1020
cctcgaaact tgttcctgct ccactcttcc ttttgggctt ttttgtttcc cgctctagcg    1080
cttcaatcgt ggttatcaag ctccaaacac tgatagttta aactgaaggc gggaaacgac    1140
aatctgatcc ccatcaagct ctagctagag cggccgcgtt atcaagcttc tgcaggtcct    1200
gctcgagtgg aagctaattc tcagtccaaa gcctcaacaa ggtcagggta cagagtctcc    1260
aaaccattag ccaaaagcta caggagatca atgaagaatc ttcaatcaaa gtaaactact    1320
```

```
gttccagcac atgcatcatg gtcagtaagt ttcagaaaaa gacatccacc gaagacttaa    1380
agttagtggg catctttgaa agtaatcttg tcaacatcga gcagctggct tgtggggacc    1440
agacaaaaaa ggaatggtgc agaattgtta ggcgcaccta ccaaaagcat ctttgccttt    1500
attgcaaaga taaagcagat tcctctagta caagtgggga acaaaataac gtggaaaaga    1560
gctgtcctga cagcccactc actaatgcgt atgacgaacg cagtgacgac cacaaaagaa    1620
ttagcttgag ctcaggattt agcagcattc cagattgggt tcaatcaaca aggtacgagc    1680
catatcactt tattcaaatt ggtatcgcca aaaccaagaa ggaactccca tcctcaaagg    1740
tttgtaagga agaattcgat atcaagcttg atatcggaag tttctctctt gagggaggtt    1800
gctcgtggaa tgggacacat atggttgtta taataaacca tttccattgt catgagattt    1860
tgaggttaat atatacttta cttgttcatt attttatttg gtgtttgaat aaatgatata    1920
aatggctctt gataatctgc attcattgag atatcaaata tttactctag agaagagtgt    1980
catatagatt gatggtccac aatcaatgaa atttttggga gacgaacatg tataaccatt    2040
tgcttgaata accttaatta aaaggtgtga ttaaatgatg tttgtaacat gtagtactaa    2100
acattcataa aacacaacca acccaagagg tattgagtat tcacggctaa acaggggcat    2160
aatggtaatt taaagaatga tattatttta tgttaaaccc taacattggt ttcggattca    2220
acgctataaa taaaaccact ctcgttgctg attccattta tcgttcttat tgaccctagc    2280
cgctacacac ttttctgcga tatctctgag gtaagcgtta acgtacccct agatcgttct    2340
ttttcttttt cgtctgctga tcgttgctca tattatttcg atgattgttg gattcgatgc    2400
tctttgttga ttgatcgttc tgaaaattct gatctgttgt ttagattta tcgattgtta    2460 atatcaacgt ttcactgctt ctaaacgata atttattcat gaaactattt tcccattctg    2520
atcgatcttg ttttgagatt ttaatttgtt cgattgattg ttggttggtg gatctatata    2580
cgagtgaact tgttgatttg cgtatttaag atgtatgtcg atttgaattg tgattgggta    2640
attctggagt agcataacaa atccagtgtt cccttttct aagggtaatt ctcggattgt    2700
ttgctttata tctcttgaaa ttgccgattt gattgaattt agctcgctta gctcagatga    2760
tagagcacca caattttgt ggtagaaatc ggtttgactc cgatagcggc ttttactat    2820 gattgttttg tgttaaagat gattttcata atggttatat atgtctactg ttttattga    2880 ttcaatattt gattgttctt ttttttgcag atttgttgac cagagatcta ccatggcgca    2940
agttagcaga atctgcaatg gtgtgcagaa cccatctctt atctccaatc tctcgaaatc    3000
cagtcaacgc aaatctccct tatcggtttc tctgaagacg cagcagcatc cacgagctta    3060
tccgatttcg tcgtcgtggg gattgaagaa gagtgggatg acgttaattg gctctgagct    3120
tcgtcctctt aaggtcatgt cttctgtttc cacggcgtgc atgcttcacg gtgcaagcag    3180
ccgtccagca actgctcgta agtcctctgg tctttctgga accgtcgta ttccaggtga    3240 caagtctatc tcccacaggt ccttcatgtt tggaggtctc gctagcggtg aaactcgtat    3300
caccggtctt ttggaaggtg aagatgttat caacactggt aaggctatgc aagctatggg    3360
tgccagaatc cgtaaggaag gtgatacttg gatcattgat ggtgttggta acggtggact    3420
ccttgctcct gaggctcctc tcgatttcgg taacgctgca actggttgcc gtttgactat    3480
gggtcttgtt ggtgtttacg atttcgatag cactttcatt ggtgacgctt ctctcactaa    3540
gcgtccaatg ggtcgtgtgt tgaacccact tcgcgaaatg ggtgtgcagg tgaagtctga    3600
agacggtgat cgtcttccag ttaccttgcg tggaccaaag actccaacgc caatcaccta    3660
cagggtacct atggcttccg ctcaagtgaa gtccgctgtt ctgcttgctg gtctcaacac    3720
```

```
cccaggtatc accactgtta tcgagccaat catgactcgt gaccacactg aaaagatgct    3780
tcaaggtttt ggtgctaacc ttaccgttga gactgatgct gacggtgtgc gtaccatccg    3840
tcttgaaggt cgtggtaagc tcaccggtca agtgattgat gttccaggtg atccatcctc    3900
tactgctttc ccattggttg ctgccttgct tgttccaggt tccgacgtca ccatccttaa    3960
cgttttgatg aacccaaccc gtactggtct catcttgact ctgcaggaaa tgggtgccga    4020
catcgaagtg atcaacccac gtcttgctgg tggagaagac gtggctgact tgcgtgttcg    4080
ttcttctact ttgaagggtg ttactgttcc agaagaccgt gctccttcta tgatcgacga    4140
gtatccaatt ctcgctgttg cagctgcatt cgctgaaggt gctaccgtta tgaacggttt    4200
ggaagaactc cgtgttaagg aaagcgaccg tctttctgct gtcgcaaacg gtctcaagct    4260
caacggtgtt gattgcgatg aaggtgagac ttctctcgtc gtgcgtggtc gtcctgacgg    4320
taagggtctc ggtaacgctt ctggagcagc tgtcgctacc cacctcgatc accgtatcgc    4380
tatgagcttc ctcgttatgg gtctcgtttc tgaaaaccct gttactgttg atgatgctac    4440
tatgatcgct actagcttcc cagagttcat ggatttgatg gctggtcttg gagctaagat    4500
cgaactctcc gacactaagg ctgcttgatg agctcaagaa ttcgagctcg gtaccggatc    4560
ctctagctag agctttcgtt cgtatcatcg gtttcgacaa cgttcgtcaa gttcaatgca    4620
tcagtttcat tgcgcacaca ccagaatcct actgagtttg agtattatgg cattgggaaa    4680 actgttttc ttgtaccatt tgttgtgctt gtaatttact gtgttttta ttcggttttc     4740 gctatcgaac tgtgaaatgg aaatggatgg agaagagtta atgaatgata tggtcctttt    4800
gttcattctc aaattaatat tatttgtttt ttctcttatt tgttgtgtgt tgaatttgaa    4860
attataagag atatgcaaac attttgtttt gagtaaaaat gtgtcaaatc gtggcctcta    4920
atgaccgaag ttaatatgag gagtaaaaca cttgtagttg taccattatg cttattcact    4980
aggcaacaaa tatattttca gacctagaaa agctgcaaat gttactgaat acaagtatgt    5040
cctcttgtgt tttagacatt tatgaacttt cctttatgta attttccaga atccttgtca    5100
gattctaatc attgctttat aattatagtt atactcatgg atttgtagtt gagtatgaaa    5160
atatttttta atgcatttta tgacttgcca attgattgac aacatgcatc aatcgacctg    5220
cagccactcg aagcggccgc atcgatcgtg aagtttctca tctaagcccc catttggacg    5280
tgaatgtaga cacgtcgaaa taagatttc cgaattagaa taatttgttt attgctttcg    5340
cctataaata cgacggatcg taatttgtcg ttttatcaaa atgtactttc atttataat    5400 aacgctcaga ctctagtgac taccaccttc actctcctca agcatttcag cctcttcccc    5460
gctcagactc cttagctttg ggagccaaat tatcccttac gttctcgact tcaaccatat    5520
gtgatagctg cctatgatac catggctact tcccccttagt tctttatctt ccttttccgc    5580
tttattccat gccttaccga tcctctgaag tgtctttgca ttagcttcat tgaaacctca    5640
cgcgatgaaa ggtgtgatgg tctcctccga tggcgcactt tcataggggt aacctaattg    5700
tcttacgacc aacataggat tataattaat acaaccctc gtcctataa aagggacatt     5760 tggaaatcct tcacataagc ataacactcc taccctctt tctttccact gtgggaacca    5820
actaatggac gctcctatca tgcctgccaa gagttcttcc caatttgcct cgtcctttcc    5880
tgagcacatg cgatgacctt gtatgggta gacagatcta ctttcatgat tgaagacgtg     5940
ggataccaac cacacataaa gagcaggcgc acaacagaaa atcctcgtag tgctcttctt    6000
gcatcttaag tcaaatgtat catacactta tgctaaaaca acaatgatcg ggctttcctt    6060
```

```
gctatggtga taagcaagaa aagcatcgat tgctactaga tccaccaact cgtctacatt    6120
cgaaaatagt actatcccaa acactagcag tgctaatacg tcgatgaatg atgcccactc    6180
tccttggctg gccagagttt ccgccttctc ctccaatcac ttccttggta ttcccctac     6240 cctattccta ctttgcttca ctcagtctaa ttctcatttc gagatcttga caactcctgc    6300
tattctcgcc atagaaggat agtacccaga aaaaggtat ggcttccttc ctcctatcgg     6360
gcatcctaag atcccttcga actcctctat ggttggtgct aactgaaagt ccccaaaagt    6420
gaagcatctg agtgattggt catagtattg ggtgagagat gcgatg                   6466
```

```
<210> SEQ ID NO 2
<211> LENGTH: 204
<212> TYPE: DNA
<213> ORGANISM: Artificial
<220> FEATURE:
<223> OTHER INFORMATION: synthetic

<400> SEQUENCE: 2
tgacaactct ttaacttatc ctctaacatc aggttttcca tacttgattt gtccctcttg    60
gcttttctaa gtttgagctc gttactgctg ccccacaaag cccctcgaaa cttgttcctg   120
ctccactctt cctttttgggc ttttttgttt cccgctctag cgcttcaatc gtggttatca   180
agctccaaac actgatagtt taaa                                           204
```

```
<210> SEQ ID NO 3
<211> LENGTH: 178
<212> TYPE: DNA
<213> ORGANISM: Artificial
<220> FEATURE:
<223> OTHER INFORMATION: synthetic

<400> SEQUENCE: 3
agaataattt gtttattgct ttcgcctata aatacgacgg atcgtaattt gtcgttttat    60
caaaatgtac tttcattta taataacgct cagactctag tgactaccac cttcactctc   120
ctcaagcatt tcagcctctt ccccgctcag actccttagc tttgggagcc aaattatc    178
```

```
<210> SEQ ID NO 4
<211> LENGTH: 23
<212> TYPE: DNA
<213> ORGANISM: Artificial
<220> FEATURE:
<223> OTHER INFORMATION: synthetic

<400> SEQUENCE: 4
taataacgct cagactctag tga                                            23
```

```
<210> SEQ ID NO 5
<211> LENGTH: 23
<212> TYPE: DNA
<213> ORGANISM: Artificial
<220> FEATURE:
<223> OTHER INFORMATION: synthetic

<400> SEQUENCE: 5
attttataat aacgctcaga ctc                                            23
```

```
<210> SEQ ID NO 6
<211> LENGTH: 23
<212> TYPE: DNA
<213> ORGANISM: Artificial
<220> FEATURE:
<223> OTHER INFORMATION: synthetic
```

```
<400> SEQUENCE: 6
tcaaaatgta ctttcatttt ata                                            23

<210> SEQ ID NO 7
<211> LENGTH: 23
<212> TYPE: DNA
<213> ORGANISM: Artificial
<220> FEATURE:
<223> OTHER INFORMATION: synthetic

<400> SEQUENCE: 7
tcgttttatc aaaatgtact ttc                                            23

<210> SEQ ID NO 8
<211> LENGTH: 23
<212> TYPE: DNA
<213> ORGANISM: Artificial
<220> FEATURE:
<223> OTHER INFORMATION: synthetic

<400> SEQUENCE: 8
ataaaacgac aaattacgat ccg                                            23

<210> SEQ ID NO 9
<211> LENGTH: 25
<212> TYPE: DNA
<213> ORGANISM: Artificial
<220> FEATURE:
<223> OTHER INFORMATION: synthetic

<400> SEQUENCE: 9
cttttgcctg ttcgtcttct agcct                                          25

<210> SEQ ID NO 10
<211> LENGTH: 25
<212> TYPE: DNA
<213> ORGANISM: Artificial
<220> FEATURE:
<223> OTHER INFORMATION: synthetic

<400> SEQUENCE: 10
tcagattgtc gtttcccgcc ttcag                                          25

<210> SEQ ID NO 11
<211> LENGTH: 1104
<212> TYPE: DNA
<213> ORGANISM: Artificial
<220> FEATURE:
<223> OTHER INFORMATION: synthetic

<400> SEQUENCE: 11
gagatatgca aacattttgt tttgagtaaa aatgtgtcaa atcgtggcct ctaatgaccg     60
aagttaatat gaggagtaaa acacttgtag ttgtaccatt atgcttattc actaggcaac    120
aaatatattt tcagacctag aaaagctgca aatgttactg aatacaagta tgtcctcttg    180
tgttttagac atttatgaac tttcctttat gtaattttcc agaatccttg tcagattcta    240
atcattgctt tataattata gttatactca tggatttgta gttgagtatg aaaatatttt    300
ttaatgcatt ttatgacttg ccaattgatt gacaacatgc atcaatcgac ctgcagccac    360
tcgaagcggc cgcatcgatc gtgaagtttc tcatctaagc ccccatttgg acgtgaatgt    420
agacacgtcg aaataaagat ttccgaatta gaataatttg tttattgctt tcgcctataa    480
```

| | |
|---|---|
| atacgacgga tcgtaatttg tcgttttatc aaaatgtact ttcattttat aataacgctc | 540 |
| agactctatt taacttatcc tctaacatca ggtttgtgac taccaccttc actctcctca | 600 |
| agcatttcag cctcttcccc gctcagactc cttagctttg ggagccaaat tatcccttac | 660 |
| gttctcgact tcaaccatat gtgatagctg cctatgatac catggctact tccccttagt | 720 |
| tctttatctt tcctttccgc tttattccat gccttaccga tcctctgaag tgtctttgca | 780 |
| ttagcttcat tgaaacctca cgcgatgaaa ggtgtgatgg tctcctccga tggcgcactt | 840 |
| ctcatagggt aacctaattg tcttacgacc aacataggat tataattaat acaacccctc | 900 |
| gtccctataa aagggacatt tggaaatcct tcacataagc ataacactcc taccctctt | 960 |
| tctttccact gtgggaacca actaatggac gctcctatca tgcctgccaa gagttcttcc | 1020 |
| caatttgcct cgtcctttcc tgagcacatg cgatgacctt gtatgggta gacagatcta | 1080 |
| cttttcatgat tgaagacgtg ggat | 1104 |

<210> SEQ ID NO 12
<211> LENGTH: 25
<212> TYPE: DNA
<213> ORGANISM: Artificial
<220> FEATURE:
<223> OTHER INFORMATION: synthetic

<400> SEQUENCE: 12

| | |
|---|---|
| cttgccaatt gattgacaac atgca | 25 |

<210> SEQ ID NO 13
<211> LENGTH: 23
<212> TYPE: DNA
<213> ORGANISM: Artificial
<220> FEATURE:
<223> OTHER INFORMATION: synthetic

<400> SEQUENCE: 13

| | |
|---|---|
| aagataaaga actaagggga agt | 23 |

<210> SEQ ID NO 14
<211> LENGTH: 6493
<212> TYPE: DNA
<213> ORGANISM: Artificial
<220> FEATURE:
<223> OTHER INFORMATION: synthetic

<400> SEQUENCE: 14

| | |
|---|---|
| tgggggctgc ctgtacttcc caaaacttcg cttccctgac ccatcatatc caggactgga | 60 |
| cgattggctt gattgatacc agatgggtga gtcgagtcca cctcggtagc ggcatttatg | 120 |
| gcaacgattg cagccacgtt gacctccatc attttttctc atgctcatca tggcctccat | 180 |
| catggtggtc atttggtctt tcatggcctc catgtcggcc ttcatctgct cttgaacttc | 240 |
| atctatctca ctcatgattc tagccttggc acgtgtttgg taagggtacc gtaaagcgcg | 300 |
| ttcgttcttt tttattacta tgattacatt ttgacgatga tgatgattgt aggaaagaat | 360 |
| gaaatgagta atgaaacaac taaataaacg tgaatgcatg acaatgataa gttgctgaag | 420 |
| tattataaat ttcatagga cattcagtgg aacgtagggt cgaatcaaat cctatttcat | 480 |
| taaaaacaat attgttcatc ttgacagagc caaagcataa ctagaaatac aacatggaca | 540 |
| catcagcgat tcctaattat gtgggtcatt agttcgacca tgtgttggca gtaacttgaa | 600 |
| agactatgaa cttcatcggg agcagagtat gtgtcagtca ccgccttggc tctggctaac | 660 |
| aaccttggga tctcttggct ctcatttaga gtaagagcaa atttgtccat ccatttcatg | 720 |

```
gcttctttat gcaataactc tatcacccct tctcttgctt cccttccaac ctgcaaggtc      780
gacacttttg cctgttcgtc ttctagcctt cgcccatgac tagcagctag gttcaccttc      840
tcttcatatt ggtcaatgat tatcaacata ttttcttttg ttttgctcaa ctgttctctc      900
aaacttctct tcgatctctg acaactcttt aacttatcct ctaacatcag gttttccata      960
cttgatttgt ccctcttggc ttttctaagt ttgagctcgt tactgctgcc ccacaaagcc     1020
cctcgaaact tgttcctgct ccactcttcc ttttgggctt ttttgtttcc cgctctagcg     1080
cttcaatcgt ggttatcaag ctccaaacac tgatagttta aactgaaggc gggaaacgac     1140
aatctgatcc ccatcaagct ctagctagag cggccgcgtt atcaagcttc tgcaggtcct     1200
gctcgagtgg aagctaattc tcagtccaaa gcctcaacaa ggtcagggta cagagtctcc     1260
aaaccattag ccaaaagcta caggagatca atgaagaatc ttcaatcaaa gtaaactact     1320
gttccagcac atgcatcatg gtcagtaagt ttcagaaaaa gacatccacc gaagacttaa     1380
agttagtggg catctttgaa agtaatcttg tcaacatcga gcagctggct tgtggggacc     1440
agacaaaaaa ggaatggtgc agaattgtta ggcgcaccta ccaaaagcat ctttgccttt     1500
attgcaaaga taaagcagat tcctctagta caagtgggga acaaaataac gtggaaaaga     1560
gctgtcctga cagcccactc actaatgcgt atgacgaacg cagtgacgac cacaaaagaa     1620
ttagcttgag ctcaggattt agcagcattc cagattgggt tcaatcaaca aggtacgagc     1680
catatcactt tattcaaatt ggtatcgcca aaaccaagaa ggaactccca tcctcaaagg     1740
tttgtaagga agaattcgat atcaagcttg atatcggaag tttctctctt gagggaggtt     1800
gctcgtggaa tgggacacat atggttgtta taataaacca tttccattgt catgagattt     1860
tgaggttaat atatacttta cttgttcatt atttatttg gtgtttgaat aaatgatata     1920
aatggctctt gataatctgc attcattgag atatcaaata tttactctag agaagagtgt     1980
catatagatt gatggtccac aatcaatgaa atttttggga gacgaacatg tataaccatt     2040
tgcttgaata accttaatta aaaggtgtga ttaaatgatg tttgtaacat gtagtactaa     2100
acattcataa aacacaacca acccaagagg tattgagtat tcacggctaa acaggggcat     2160
aatggtaatt taaagaatga tattatttta tgttaaaccc taacattggt ttcggattca     2220
acgctataaa taaaaccact ctcgttgctg attccattta tcgttcttat tgaccctagc     2280
cgctacacac ttttctgcga tatctctgag gtaagcgtta acgtacccctt agatcgttct     2340 ttttctttt cgtctgctga tcgttgctca tattatttcg atgattgttg gattcgatgc     2400
tctttgttga ttgatcgttc tgaaaattct gatctgttgt ttagatttta tcgattgtta     2460
atatcaacgt ttcactgctt ctaaacgata atttattcat gaaactattt tcccattctg     2520
atcgatcttt ttttgagatt ttaatttgtt cgattgattg ttggttggtg gatctatata     2580
cgagtgaact tgttgatttg cgtatttaag atgtatgtcg atttgaattg tgattgggta     2640
attctggagt agcataacaa atccagtgtt ccctttttct aagggtaatt ctcggattgt     2700
ttgctttata tctcttgaaa ttgccgattt gattgaattt agctcgctta gctcagatga     2760
tagagcacca caattttgt ggtagaaatc ggtttgactc cgatagcggc ttttactat      2820 gattgttttg tgttaaagat gattttcata atggttatat atgtctactg ttttattga      2880 ttcaatattt gattgttctt ttttttgcag atttgttgac cagagatcta ccatggcgca     2940
agttagcaga atctgcaatg gtgtgcagaa cccatctctt atctccaatc tctcgaaatc     3000
cagtcaacgc aaatctccct tatcggtttc tctgaagacg cagcagcatc cacgagctta     3060
```

```
tccgatttcg tcgtcgtggg gattgaagaa gagtgggatg acgttaattg gctctgagct    3120
tcgtcctctt aaggtcatgt cttctgtttc cacggcgtgc atgcttcacg gtgcaagcag    3180
ccgtccagca actgctcgta agtcctctgg tctttctgga accgtccgta ttccaggtga    3240
caagtctatc tcccacaggt ccttcatgtt tggaggtctc gctagcggtg aaactcgtat    3300
caccggtctt ttggaaggtg aagatgttat caacactggt aaggctatgc aagctatggg    3360
tgccagaatc cgtaaggaag gtgatacttg gatcattgat ggtgttggta acggtggact    3420
ccttgctcct gaggctcctc tcgatttcgg taacgctgca actggttgcc gtttgactat    3480
gggtcttgtt ggtgtttacg atttcgatag cactttcatt ggtgacgctt ctctcactaa    3540
gcgtccaatg ggtcgtgtgt tgaacccact tcgcgaaatg ggtgtgcagg tgaagtctga    3600
agacggtgat cgtcttccag ttaccttgcg tggaccaaag actccaacgc caatcaccta    3660
cagggtacct atggcttccg ctcaagtgaa gtccgctgtt ctgcttgctg gtctcaacac    3720
cccaggtatc accactgtta tcgagccaat catgactcgt gaccacactg aaaagatgct    3780
tcaaggtttt ggtgctaacc ttaccgttga gactgatgct gacggtgtgc gtaccatccg    3840
tcttgaaggt cgtggtaagc tcaccggtca agtgattgat gttccaggtg atccatcctc    3900
tactgctttc ccattggttg ctgccttgct tgttccaggt tccgacgtca ccatccttaa    3960
cgttttgatg aacccaaccc gtactggtct catcttgact ctgcaggaaa tgggtgccga    4020
catcgaagtg atcaacccac gtcttgctgg tggagaagac gtggctgact tgcgtgttcg    4080
ttcttctact ttgaagggtg ttactgttcc agaagaccgt gctccttcta tgatcgacga    4140
gtatccaatt ctcgctgttg cagctgcatt cgctgaaggt gctaccgtta tgaacggttt    4200
ggaagaactc cgtgttaagg aaagcgaccg tctttctgct gtcgcaaacg gtctcaagct    4260
caacggtgtt gattgcgatg aaggtgagac ttctctcgtc gtgcgtggtc gtcctgacgg    4320
taagggtctc ggtaacgctt ctggagcagc tgtcgctacc cacctcgatc accgtatcgc    4380
tatgagcttc ctcgttatgg gtctcgtttc tgaaaaccct gttactgttg atgatgctac    4440
tatgatcgct actagcttcc cagagttcat ggatttgatg gctggtcttg gagctaagat    4500
cgaactctcc gacactaagg ctgcttgatg agctcaagaa ttcgagctcg gtaccggatc    4560
ctctagctag agctttcgtt cgtatcatcg gtttcgacaa cgttcgtcaa gttcaatgca    4620
tcagtttcat tgcgcacaca ccagaatcct actgagtttg agtattatgg cattgggaaa    4680
actgtttttc ttgtaccatt tgttgtgctt gtaatttact gtgtttttta ttcggttttc    4740
gctatcgaac tgtgaaatgg aaatggatgg agaagagtta atgaatgata tggtccttt    4800 gttcattctc aaattaatat tatttgtttt ttctcttatt tgttgtgtgt tgaatttgaa    4860
attataagag atatgcaaac attttgtttt gagtaaaaat gtgtcaaatc gtggcctcta    4920
atgaccgaag ttaatatgag gagtaaaaca cttgtagttg taccattatg cttattcact    4980
aggcaacaaa tatattttca gacctagaaa agctgcaaat gttactgaat acaagtatgt    5040
cctcttgtgt tttagacatt tatgaacttt cctttatgta attttccaga atccttgtca    5100
gattctaatc attgctttat aattatagtt atactcatgg atttgtagtt gagtatgaaa    5160
atatttttta atgcatttta tgacttgcca attgattgac aacatgcatc aatcgacctg    5220
cagccactcg aagcggccgc atcgatcgtg aagtttctca tctaagcccc catttggacg    5280
tgaatgtaga cacgtcgaaa taaagatttc cgaattagaa taatttgttt attgctttcg    5340
cctataaata cgacggatcg taatttgtcg ttttatcaaa atgtactttc attttataat    5400
aacgctcaga ctctatttaa cttatcctct aacatcaggt tgtgactac caccttcact    5460
```

-continued

```
ctcctcaagc atttcagcct cttccccgct cagactcctt agctttggga gccaaattat    5520
cccttacgtt ctcgacttca accatatgtg atagctgcct atgataccat ggctacttcc    5580
ccttagttct ttatctttcc tttccgcttt attccatgcc ttaccgatcc tctgaagtgt    5640
ctttgcatta gcttcattga aacctcacgc gatgaaaggt gtgatggtct cctccgatgg    5700
cgcacttctc atagggtaac ctaattgtct tacgaccaac ataggattat aattaataca    5760 accctcgtc cctataaaag ggacatttgg aaatccttca cataagcata acactcctac     5820 ccctcttct ttccactgtg ggaaccaact aatggacgct cctatcatgc ctgccaagag     5880
ttcttcccaa tttgcctcgt cctttcctga gcacatgcga tgaccttgta tggggtagac    5940
agatctactt tcatgattga agacgtggga taccaaccac acataaagag caggcgcaca    6000
acagaaaatc ctcgtagtgc tcttcttgca tcttaagtca aatgtatcat acacttatgc    6060
taaaacaaca atgatcgggc tttccttgct atggtgataa gcaagaaaag catcgattgc    6120
tactagatcc accaactcgt ctacattcga aaatagtact atcccaaaca ctagcagtgc    6180
taatacgtcg atgaatgatg cccactctcc ttggctggcc agagtttccg ccttctcctc    6240
caatcacttc cttggtattc cccctaccct attcctactt tgcttcactc agtctaattc    6300
tcatttcgag atcttgacaa ctcctgctat tctcgccata gaaggatagt acccagaaaa    6360
aaggtatggc ttccttcctc ctatcgggca tcctaagatc ccttcgaact cctctatggt    6420
tggtgctaac tgaaagtccc caaaagtgaa gcatctgagt gattggtcat agtattgggt    6480
gagagatgcg atg                                                      6493
```

<210> SEQ ID NO 15
<211> LENGTH: 801
<212> TYPE: PRT
<213> ORGANISM: Unknown
<220> FEATURE:
<223> OTHER INFORMATION: bacterial
<400> SEQUENCE: 15

```
Met Glu Pro Ser Leu Ser Phe Tyr Asn Lys Ala Arg Asn Tyr Ala Thr
1               5                   10                  15

Lys Lys Pro Tyr Ser Val Glu Lys Phe Lys Leu Asn Phe Gln Met Pro
            20                  25                  30

Thr Leu Ala Ser Gly Trp Asp Val Asn Lys Glu Lys Asn Asn Gly Ala
        35                  40                  45

Ile Leu Phe Val Lys Asn Gly Leu Tyr Tyr Leu Gly Ile Met Pro Lys
    50                  55                  60

Gln Lys Gly Arg Tyr Lys Ala Leu Ser Phe Glu Pro Thr Glu Lys Thr
65                  70                  75                  80

Ser Glu Gly Phe Asp Lys Met Tyr Tyr Asp Tyr Phe Pro Asp Ala Ala
                85                  90                  95

Lys Met Ile Pro Lys Cys Ser Thr Gln Leu Lys Ala Val Thr Ala His
            100                 105                 110

Phe Gln Thr His Thr Thr Pro Ile Leu Leu Ser Asn Asn Phe Ile Glu
        115                 120                 125

Pro Leu Glu Ile Thr Lys Glu Ile Tyr Asp Leu Asn Asn Pro Glu Lys
    130                 135                 140

Glu Pro Lys Lys Phe Gln Thr Ala Tyr Ala Lys Lys Thr Gly Asp Gln
145                 150                 155                 160

Lys Gly Tyr Arg Glu Ala Leu Cys Lys Trp Ile Asp Phe Thr Arg Asp
                165                 170                 175
```

```
Phe Leu Ser Lys Tyr Thr Lys Thr Thr Ser Ile Asp Leu Ser Ser Leu
            180                 185                 190

Arg Pro Ser Ser Gln Tyr Lys Asp Leu Gly Glu Tyr Tyr Ala Glu Leu
            195                 200                 205

Asn Pro Leu Leu Tyr His Ile Ser Phe Gln Arg Ile Ala Glu Lys Glu
210                 215                 220

Ile Met Asp Ala Val Glu Thr Gly Lys Leu Tyr Leu Phe Gln Ile Tyr
225                 230                 235                 240

Asn Lys Asp Phe Ala Lys Gly His His Gly Lys Pro Asn Leu His Thr
                245                 250                 255

Leu Tyr Trp Thr Gly Leu Phe Ser Pro Glu Asn Leu Ala Lys Thr Ser
            260                 265                 270

Ile Lys Leu Asn Gly Gln Ala Glu Leu Phe Tyr Arg Pro Lys Ser Arg
            275                 280                 285

Met Lys Arg Met Ala His Arg Leu Gly Glu Lys Met Leu Asn Lys Lys
            290                 295                 300

Leu Lys Asp Gln Lys Thr Pro Ile Pro Asp Thr Leu Tyr Gln Glu Leu
305                 310                 315                 320

Tyr Asp Tyr Val Asn His Arg Leu Ser His Asp Leu Ser Asp Glu Ala
                325                 330                 335

Arg Ala Leu Leu Pro Asn Val Ile Thr Lys Glu Val Ser His Glu Ile
            340                 345                 350

Ile Lys Asp Arg Arg Phe Thr Ser Asp Lys Phe Phe Phe His Val Pro
            355                 360                 365

Ile Thr Leu Asn Tyr Gln Ala Ala Asn Ser Pro Ser Lys Phe Asn Gln
            370                 375                 380

Arg Val Asn Ala Tyr Leu Lys Glu His Pro Glu Thr Pro Ile Ile Gly
385                 390                 395                 400

Ile Asp Arg Gly Glu Arg Asn Leu Ile Tyr Ile Thr Val Ile Asp Ser
                405                 410                 415

Thr Gly Lys Ile Leu Glu Gln Arg Ser Leu Asn Thr Ile Gln Gln Phe
            420                 425                 430

Asp Tyr Gln Lys Lys Leu Asp Asn Arg Glu Lys Glu Arg Val Ala Ala
            435                 440                 445

Arg Gln Ala Trp Ser Val Val Gly Thr Ile Lys Asp Leu Lys Gln Gly
450                 455                 460

Tyr Leu Ser Gln Val Ile His Glu Ile Val Asp Leu Met Ile His Tyr
465                 470                 475                 480

Gln Ala Val Val Val Leu Glu Asn Leu Asn Phe Gly Phe Lys Ser Lys
                485                 490                 495

Arg Thr Gly Ile Ala Glu Lys Ala Val Tyr Gln Gln Phe Glu Lys Met
            500                 505                 510

Leu Ile Asp Lys Leu Asn Cys Leu Val Leu Lys Asp Tyr Pro Ala Glu
            515                 520                 525

Lys Val Gly Gly Val Leu Asn Pro Tyr Gln Leu Thr Asp Gln Phe Thr
530                 535                 540

Ser Phe Ala Lys Met Gly Thr Gln Ser Gly Phe Leu Phe Tyr Val Pro
545                 550                 555                 560

Ala Pro Tyr Thr Ser Lys Ile Asp Pro Leu Thr Gly Phe Val Asp Pro
                565                 570                 575

Phe Val Trp Lys Thr Ile Lys Asn His Glu Ser Arg Lys His Phe Leu
            580                 585                 590
```

```
Glu Gly Phe Asp Phe Leu His Tyr Asp Val Lys Thr Gly Asp Phe Ile
            595                 600                 605

Leu His Phe Lys Met Asn Arg Asn Leu Ser Phe Gln Arg Gly Leu Pro
    610                 615                 620

Gly Phe Met Pro Ala Trp Asp Ile Val Phe Glu Lys Asn Glu Thr Gln
625                 630                 635                 640

Phe Asp Ala Lys Gly Thr Pro Phe Ile Ala Gly Lys Arg Ile Val Pro
                645                 650                 655

Val Ile Glu Asn His Arg Phe Thr Gly Arg Tyr Arg Asp Leu Tyr Pro
            660                 665                 670

Ala Asn Glu Leu Ile Ala Leu Leu Glu Glu Lys Gly Ile Val Phe Arg
        675                 680                 685

Asp Gly Ser Asn Ile Leu Pro Lys Leu Leu Glu Asn Asp Asp Ser His
    690                 695                 700

Ala Ile Asp Thr Met Val Ala Leu Ile Arg Ser Val Leu Gln Met Arg
705                 710                 715                 720

Asn Ser Asn Ala Ala Thr Gly Glu Asp Tyr Ile Asn Ser Pro Val Arg
                725                 730                 735

Asp Leu Asn Gly Val Cys Phe Asp Ser Arg Phe Gln Asn Pro Glu Trp
            740                 745                 750

Pro Met Asp Ala Asp Ala Asn Gly Ala Tyr His Ile Ala Leu Lys Gly
        755                 760                 765

Gln Leu Leu Asn His Leu Lys Glu Ser Lys Asp Leu Lys Leu Gln
    770                 775                 780

Asn Gly Ile Ser Asn Gln Asp Trp Leu Ala Tyr Ile Gln Glu Leu Arg
785                 790                 795                 800

Asn

<210> SEQ ID NO 16
<211> LENGTH: 205
<212> TYPE: DNA
<213> ORGANISM: Artificial
<220> FEATURE:
<223> OTHER INFORMATION: synthetic

<400> SEQUENCE: 16
agaataattt gtttattgct ttcgcctata aatacgacgg atcgtaattt gtcgttttat      60
caaaatgtac tttcatttta taataacgct cagactctat ttaacttatc ctctaacatc     120
aggtttgtga ctaccacctt cactctcctc aagcatttca gcctcttccc cgctcagact     180
ccttagcttt gggagccaaa ttatc                                           205

<210> SEQ ID NO 17
<211> LENGTH: 47
<212> TYPE: DNA
<213> ORGANISM: Artificial
<220> FEATURE:
<223> OTHER INFORMATION: synthetic

<400> SEQUENCE: 17
tcagactcta tttaacttat cctctaacat caggtttgtg actacca                    47

<210> SEQ ID NO 18
<211> LENGTH: 27
<212> TYPE: DNA
<213> ORGANISM: Artificial
<220> FEATURE:
<223> OTHER INFORMATION: synthetic
```

<400> SEQUENCE: 18
tttaacttat cctctaacat caggttt                                    27

<210> SEQ ID NO 19
<211> LENGTH: 23
<212> TYPE: DNA
<213> ORGANISM: Artificial
<220> FEATURE:
<223> OTHER INFORMATION: synthetic

<400> SEQUENCE: 19
acttatcctc taacatcagg ttt                                        23

<210> SEQ ID NO 20
<211> LENGTH: 23
<212> TYPE: DNA
<213> ORGANISM: Artificial
<220> FEATURE:
<223> OTHER INFORMATION: synthetic

<400> SEQUENCE: 20
gaggggcttt gtggggcagc agt                                        23

<210> SEQ ID NO 21
<211> LENGTH: 23
<212> TYPE: DNA
<213> ORGANISM: Artificial
<220> FEATURE:
<223> OTHER INFORMATION: synthetic

<400> SEQUENCE: 21
tggggcagca gtaacgagct caa                                        23

<210> SEQ ID NO 22
<211> LENGTH: 23
<212> TYPE: DNA
<213> ORGANISM: Artificial
<220> FEATURE:
<223> OTHER INFORMATION: synthetic

<400> SEQUENCE: 22
agctcgttac tgctgcccca caa                                        23

<210> SEQ ID NO 23
<211> LENGTH: 23
<212> TYPE: DNA
<213> ORGANISM: Artificial
<220> FEATURE:
<223> OTHER INFORMATION: synthetic

<400> SEQUENCE: 23
taagtttgag ctcgttactg ctg                                        23

<210> SEQ ID NO 24
<211> LENGTH: 23
<212> TYPE: DNA
<213> ORGANISM: Artificial
<220> FEATURE:
<223> OTHER INFORMATION: synthetic

<400> SEQUENCE: 24
tccctcttgg cttttctaag ttt                                        23

<210> SEQ ID NO 25
<211> LENGTH: 25

```
<212> TYPE: DNA
<213> ORGANISM: Artificial
<220> FEATURE:
<223> OTHER INFORMATION: synthetic

<400> SEQUENCE: 25
attgcgcaca caccagaatc ctact                                          25

<210> SEQ ID NO 26
<211> LENGTH: 25
<212> TYPE: DNA
<213> ORGANISM: Artificial
<220> FEATURE:
<223> OTHER INFORMATION: synthetic

<400> SEQUENCE: 26
tatcaccata gcaaggaaag cccga                                          25
```